(12) United States Patent
Bloxham et al.

(10) Patent No.: US 8,003,806 B2
(45) Date of Patent: Aug. 23, 2011

(54) INTEGRIN ANTAGONISTS USEFUL AS ANTICANCER AGENTS

(75) Inventors: Jason Bloxham, Oxford (GB); Gary V. Borzillo, Farmingdale, NY (US); Eric William Collington, Oxford (GB); Shazia Sadiq, Oxford (GB); Colin Peter Sambrook Smith, Oxford (GB); Chris L. Waller, Farmingdale, NY (US); Graham M. Wynne, Oxford (GB)

(73) Assignee: OSI Pharmaceuticals, LLC, Farmingdale, NY (US)

( * ) Notice: Subject to any disclaimer, the term of this patent is extended or adjusted under 35 U.S.C. 154(b) by 0 days.

(21) Appl. No.: 11/270,088

(22) Filed: Nov. 9, 2005

(65) Prior Publication Data

US 2006/0116383 A1 Jun. 1, 2006

Related U.S. Application Data

(60) Provisional application No. 60/627,775, filed on Nov. 12, 2004.

(51) Int. Cl.
*A61K 31/4184* (2006.01)
*C07D 235/04* (2006.01)
(52) U.S. Cl. ............... 548/310.1; 514/242; 514/258; 514/259; 514/307; 514/311; 514/322; 514/338; 514/365; 514/378; 514/252.01; 514/255.01; 514/361; 514/394; 544/182; 544/238; 544/262; 544/333; 544/370; 546/146; 546/169; 546/199; 546/273.4; 548/127; 548/181; 548/248
(58) Field of Classification Search ............... 548/310.1
See application file for complete search history.

(56) References Cited

U.S. PATENT DOCUMENTS

| 4,650,749 | A | 3/1987 | Sato |
| 5,294,631 | A | 3/1994 | Franz |
| 2003/0045728 | A1 | 3/2003 | Wiesner |

FOREIGN PATENT DOCUMENTS

| WO | WO-97/10219 A1 * | 3/1997 |
| WO | 00/51608 A | 9/2000 |
| WO | 00/68188 A | 11/2000 |
| WO | 01/94311 A | 12/2001 |
| WO | 02/18377 A | 3/2002 |
| WO | 03/041708 A | 5/2003 |
| WO | 2004/074284 A | 9/2004 |
| WO | 2004/099192 A | 11/2004 |
| WO | 2006/034418 A | 3/2006 |
| WO | 2006021418 A | 3/2006 |

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*
Vippagunta et al. (Advanced Drug Delivery Reviews, 48 (2001), pp. 3-26.*
Golub et al., Science, vol. 286, Oct. 15, 1999, pp. 531-537.*
CA Registry No. 189042-88-4, entry date in the Registry file on STN on May 15, 1997.*
CA Registry No. 189042-88-4, entry date in the Registry file on STN on May 15, 1997.
Database Caplus (Online) Chemical Abstracts Service, Columbus, Ohio, US; Tan, R. et al.: Study on synthesis, anti-inflammatory activity, and ulcerogenic effects of benzimidazole derivatives XP002382547 retreived from STN Database accession No. 2001:844552 compounds with RN 40332-16-9, 14840-18-7 abstract & Zhongguo Yaowu Huaxue Zazhi, 11 (5), 259-262 Coden: Zyhzef; ISSN: 1005-0108, 2001.
Golub, T.R. et al. (1999) Science 286, Oct. 15, 1999, pp. 531-537.
Souillac, P. et al. (1999) Characterization of Delivery Systems, Differential Scanning Calorimetry in Encyclopedia of Controlled Drug Delivery, John Wiley & Sons, pp. 212-227.
Vippagunta, S.R. et al. (2001) Advanced Drug Delivery Reviews 48:3-26.
Yadav-Bhatnagar, N. et al. (2002) Journal of Combinatorial Chemistry 4(1):49-55.
International Preliminary Report on Patentability in PCT/US2005/042048, May 15, 2007.
International Search Report in PCT/US2005/042048, Jun. 19, 2006.
Tan, R. et al. (2001) Zhongguo Yaowu Huaxue Zazhi, 11 (5), 259-262 *Non english—includes English abstract, Chinese Journal of Medicinal Chemistry.
Written Opinion of the International Search Authority in PCT/US2005/042048, Jun. 15, 2006.

* cited by examiner

*Primary Examiner* — Laura L. Stockton
(74) *Attorney, Agent, or Firm* — Michael J. Rafa; OSI Pharmaceuticals, LLC

(57) ABSTRACT

The invention relates to compounds of the Formula 1

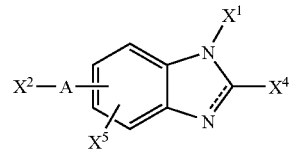

and to pharmaceutically acceptable salts and solvates thereof, wherein A, $X^2$, $X^4$, $X^5$ and $X^1$ are as defined herein. The invention also relates to methods of treating abnormal cell growth in mammals by administering the compounds of Formula 1 and to pharmaceutical compositions for treating such disorders which contain the compounds of Formula 1.

8 Claims, No Drawings

INTEGRIN ANTAGONISTS USEFUL AS ANTICANCER AGENTS

This application claims the benefit of U.S. Provisional App. No. 60/627,775, filed Nov. 12, 2004, which is herein incorporated by reference in its entirety.

BACKGROUND OF THE INVENTION

The present invention is directed to novel compounds that are useful in the treatment of abnormal cell growth, such as cancer, in mammals. This invention is also directed to a method of using such compounds in the treatment of abnormal cell growth in mammals, especially humans, and to pharmaceutical compositions containing such compounds.

The integrins comprise a family of cell surface receptors are expressed in many tissues. A major function of this class of receptors is to promote adhesion events between cells and other cells, or between cells and proteins of the extracellular matrix (ECM). On the cell surface, integrins can form complexes with other receptors, proteases, and integrin-associated proteins (IAPs). Within the cytoplasm, integrins interact with cytoskeletal proteins, adaptor proteins, and signaling molecules. The adhesion events that result in integrin ligation generate intracellular signals that ultimately regulate diverse cell fates such as adhesion, survival, migration, invasion and differentiation. Some integrins have been implicated in human pathology, particularly diseases associated with undesirable forms of angiogenesis, scar formation, inflammation and cell growth or survival.

The structure of integrin molecules has been reviewed periodically over the last decade [eg. Seftor, *Am. J. Path.*, 153, (1998), 1347-1351]. Integrins are heterodimeric glycoproteins composed of an α subunit non-covalently associated with a β subunit. To date, at least 14α subunits and 8β subunits have been described, which can associate in various combinations to form the approximately 20 different integrins currently known. Diversity may be limited by differences in affinity between subunits; for example, the human $\alpha_v$ subunit can associate with a number of β partners to form multiple integrins ($\alpha_v\beta_1$, $\alpha_v\beta_3$, $\alpha_v\beta_5$, $\alpha_v\beta_6$, $\alpha_v\beta_8$) whereas the $\alpha_{IIb}$ subunit is identified only in $\alpha_{IIb}\beta_3$ integrins. An important feature of integrin biology is that many integrins recognize short (3 to 6 amino acid) sequences within their corresponding ligands. In particular, the tripeptide RGD (Arg-Gly-Asp) was the first defined integrin recognition site, although others have since been identified by different experimental approaches [Healy et al., *Biochemistry*, 34, (1995), 3948-3955]. The RGD site is found in a variety of adhesive proteins, including vitronectin, fibronectin, fibrinogen, von Willebrand factor, osteopontin and other adhesive proteins. Integrin $\alpha_v\beta_3$ is promiscuous in its ability to recognize the RGD sequence in different proteins that serve as its ligands (examples include vitronectin, fibrinogen, denatured collagen and osteopontin), whereas other integrins recognize RGD sequences in more restricted contexts. The affinity by which certain integrins bind ligands can be regulated by intracellular signals that are transduced to the extracellular ligand-binding domain. Such "inside-out" signaling serves to modulate integrin adhesion events in response to environmental cues, such as those that induce platelet activation or inflammation.

Integrin $\alpha_v\beta_3$, also known as the classical vitronectin receptor, is relatively restricted in its expression in adult tissues, being found on a subset of inflammatory cells, osteoclasts, smooth muscle cells and fibroblasts. This integrin is not expressed appreciably in the mature epithelium or endothelium, but becomes highly expressed on proliferating endothelial cells in wounds, in inflammatory states such as endometriosis, and in the vasculature of solid tumors [Clark et al., *Am. J. Path.*, 148, (1996), 1407-1421; Hii et al., *Human Reproduction*, 13, (1998), 1030-1035; Brooks et al., *Science*, 264, (1994), 569-571]. Expression of $\alpha_v\beta_3$ is considered a marker for ongoing angiogenesis, and in adults, radiolabeled antibodies to $\alpha_v\beta_3$ have been used to detect the vascular beds of solid tumors [Sipkins et al., *Nat. Med.*, 4, (1998), 623-626].

Functional roles for $\alpha_v\beta_3$ have been examined by inhibiting $\alpha_v\beta_3$/ligand interactions by pharmacological or genetic manipulation. For example, the interactions between $\alpha_v\beta_3$ and its ligands can be antagonized by peptides spanning the RGD sequence, by peptidomimetic compounds, and by dis-integrins, a class of integrin-binding proteins derived mainly from snake venoms. Several antibodies can bind $\alpha_v\beta_3$ in a manner that blocks ligand accessibility, and are particularly useful as selective $\alpha_v\beta_3$ antagonists. Such studies have defined a role for $\alpha_v\beta_3$ during tissue remodeling events, such as those associated with angiogenesis and embryonic neovascularization [Brooks et al., *Cell*, 79, (1994), 1157-1164; Drake et al., *J. Cell Sci.*, 108, (1995), 2655-2661]. Selective disruption of $\alpha_v\beta_3$ by a neutralizing monoclonal antibody, LM609, disrupts angiogenesis in the chicken chorioallantoic membrane (CAM), and in the mouse retina and rabbit cornea. LM609 also inhibits neovascularization in the quail embryo. Inhibition of angiogenesis is associated with endothelial cell apoptosis, and the ability of $\alpha_v\beta_3$ to promote cell survival has been confirmed in vitro [Petitclerc et al., *Cancer Research*, 59, (1999), 2724-2730]. Importantly, selective $\alpha_v\beta_3$ antagonists do not appear to harm the mature vasculature, and are tolerated in adult animals [Brooks et al., *J. Clin. Invest.*, 96, (1995), 1815-1822; reviewed by Elicieri and Cheresh, *J. Clin. Invest.*, 103, (1999), 1227-1230].

The ability of $\alpha_v\beta_3$ to transduce survival signals for vascular endothelial cells suggests that antagonists of this integrin would be useful agents for inhibiting angiogenesis in tumors, and ultimately, for inhibiting tumor growth. Antibody LM609 has been shown to block angiogenesis in the chicken chorio-allantoic membrane (CAM) induced by cytokines (bFGF, TNF-α) and melanoma implants. LM609 also impeded the growth of four distinct tumors inoculated onto the CAM [Brooks et al., *Science*, 264, (1994), 569-57; Brooks et al., *Cell*, 79, (1994), 1157-1164]. The inhibition of the development of human blood vessels and tumor growth in a SCID mouse/human skin chimeric model has also been reported [Brooks et al., *J. Clin. Invest.*, 96, (1995), 1815-1822].

Multiple cytokines and secreted factors can induce angiogenesis. In the rabbit cornea, angiogenesis induced by bFGF or TNF-α was inhibited by LM609, but was not inhibited appreciably by a neutralizing antibody (P1F6) that binds a second vitronectin receptor, $\alpha_v\beta_5$ [Friedlander et al., *Science*, 270, (1995), 1500-1502]. In contrast, P1F6 was more effective than LM609 when angiogenesis was induced by VEGF. The same tendencies were noted when angiogenesis was induced in the chick CAM, although LM609 retained a partial ability to inhibit VEGF-induced angiogenesis in this system. Neither antibody was as effective as an RGD peptide that blocked both $\alpha_v\beta_3$ and $\alpha_v\beta_5$. For some tumors, it may thus be preferable to utilize a drug that blocks both $\alpha_v\beta_3$ and $\alpha_v\beta_5$ in others it may be more preferable to inhibit $\alpha_v\beta_3$ selectively whilst some other tumors or ocular disorders (see below) may respond best to selective inhibitors of $\alpha_v\beta_5$.

Integrin $\alpha_v\beta_3$ can transduce survival signals in proliferating vascular endothelial cells. Ectopic integrin expression on a subset of tumors might also promote inappropriate survival of transformed cells in cancer patients. Human cutaneous melanoma cells express multiple integrin types, but $\alpha_v\beta_3$ is restricted to cells within the vertical growth phase, as compared to radial growth phase cells found in nevi [Albelda et al., *Cancer Research,* 50, (1990), 6757-6764]. Subsequent studies have demonstrated that forced expression of the $\beta_3$ subunit alone results in association with pre-existing $\alpha_v$ subunits, expression of $\alpha_v\beta_3$ and a concomitant transition to a more malignant phenotype [Hsu et al., *Am. J. Path.,* 153, (1998), 1435-1442]. Ultimately, expression of $\alpha_v\beta_3$ on tumor cells may transduce survival signals, as well as recruit matrix metalloproteinases (eg. MMP-2) and other integrin-binding proteins that facilitate invasion [Brooks et al., *Cell,* 92, (1998), 391-400]. Specific inhibitors of $\alpha_v\beta_3$ may be used to directly inhibit certain tumors, particularly melanomas, where $\alpha_v\beta_3$ expression has been particularly well documented.

Antagonists of $\alpha_v$ integrins inhibit vascular endothelial cell survival, implying that such antagonists might also be used for the treatment of indications such as ocular disorders associated with angiogenesis [age-related macular degeneration (ARMD), presumed ocular histoplasmosis syndrome (POHS), and retinal neovascularization from proliferative diabetic retinopathy (PDR)]. Friedlander et al., [*Proc. Natl. Acad. Sci. USA,* 93, (1996), 9764-9769] reported that $\alpha_v\beta_3$ was selectively found on blood vessels from patients with ARMD and POHS, whereas $\alpha_v\beta_3$ and $\alpha_v\beta_5$ were co-expressed on blood vessels from patients with PDR. Normal ocular vessels were largely negative for both integrins, suggesting that chemical inhibition of $\alpha_v\beta_3$ and/or $\alpha_v\beta_5$ may be useful for the treatment of these blinding disorders.

Rheumatoid arthritis (RA) is an inflammatory disease that ultimately causes joint destruction. The RA joint is characterized by excessive cell proliferation and vascularization, and synovial blood vessels from patients with this disease show increased levels of $\alpha_v\beta_3$ [Johnson et al., *Arthritis Rheum.,* 36, (1993), 137-146]. In a rabbit model of antigen-induced arthritis (AIA) augmented by bFGF, injection of a cyclic peptide with selectivity for $\alpha_v\beta_3$ reduced angiogenesis, pannus formation and cartilage erosion (Strogard et al., *J. Clin. Invest.,* 103, (1999), 47-54). The peptide inhibitor, c[RGDfV], was approximately 100-fold more potent for $\alpha_v\beta_3$ inhibition relative to $\alpha_v\beta_5$ inhibition in vitro ($IC_{50}$: 4.8 vs 450 nM, respectively). A second peptide, c[RGDf(N-Me)V], exhibited a similar in vitro potency towards $\alpha_v\beta_3$ and improved potency to $\alpha_v\beta_5$ (2.3 vs 37 nM, respectively), but was a slightly inferior antagonist of RA. Inhibitors of $\alpha_v\beta_3$ may therefore have utility in the treatment of patients with RA.

Integrin $\alpha_v\beta_3$ contributes to the process of bone resorption, by facilitating the adhesion of osteoclasts to ligands such as bone sialoprotein and osteopontin [Ross et al., *J. Biol. Chem.,* 268, (1993), 9901-9907]. When bone resorption by osteoclasts exceeds bone-forming activity, osteoporosis (loss of bone) results. Osteoporosis is a major health problem that is associated with an increased risk of bone fractures, incapacitation, pain and mortality. Neutralizing antibodies to $\alpha_v\beta_3$ as well as RGD peptides, and peptidomimetic compounds have been shown to inhibit the resorption of bone and dentine by osteoclasts (Engleman et al., *J. Clin. Invest.,* 99, (1997), 2284-2292; Horton et al., *Exp. Cell Res.,* 195, (1991), 368-375; Sato et al., *J. Cell Biol.,* 111, (1990), 1713-1723; Fisher et al., *Endocrinology,* 132, (1993), 1411-1413]. Antagonism of osteoclasts by $\alpha_v\beta_3$ selective antagonists appears to be a promising approach towards restoring an equilibrium to bone remodeling in osteoporosis.

Other diseases characterized by excessive bone loss include Paget's disease, humoral hypercalcemia of malignancy (HHM), hypercalcemia from tumors metastatic to bone, and osteoporosis induced by glucocorticoid treatment. Caron et al. [*Cancer Research,* 58, (1998), 1930-1935] have recently reported that a peptidomimetic antagonist of $\alpha_v\beta_3$, SC-68448, could inhibit tumor growth and the resulting HHM in a SCID mouse/rat Leydig cell tumor model. Patients with any of the above disorders might benefit from treatment with selective inhibitors of $\alpha_v\beta_3$.

Integrin $\alpha_v\beta_3$ is expressed on vascular smooth muscle cells (VSMC), and antagonists of this integrin have therefore been evaluated for inhibition of coronary restenosis. RGD containing peptides inhibit neointimal hyperplasia in various small animal models, such as rat, rabbit, hamster and guinea pig [Choi et al., *J. Vasc. Surgery,* 19, (1994), 125-134]. Another $\alpha_v\beta_3$ antagonist, XJ 735, was shown to be selective for $\alpha_v\beta_3$ relative to other integrins ($\alpha_v\beta_5$, $\alpha_{IIb}\beta_3$, $\alpha_4\beta_1$, $\alpha_5\beta_1$), and to inhibit coronary restenosis in a porcine coronary injury model [Srivasta et al., *Cardiovascular Research,* 36, (1997), 408-428]. This study confirms the idea that selective $\alpha_v\beta_3$ antagonism can impede neointimal cell proliferation and stenosis following vessel injury. The study also supports the possibility that the positive long-term effects of Abciximab (ReoPro, chimeric 7E3 Fab) in the EPIC trial may have been partly due to the inhibition of $\alpha_v\beta_3$.

A number of microbial pathogens, including adenovirus, hantaviruses, *Borrelia burgdorferi, Yersinia* spp., *Bordetella pertussis*, and group A *Streptococcus*, bind integrins, usually through an RGD motif on a cell surface protein. Some of these proteins serve as virulence factors [Stockbauer et al., *Proc. Natl. Acad. Sci. USA,* 96, (1999), 242-247]. Integrin antagonists may therefore be useful in inhibiting certain forms of microbial infections.

DD 123466 shows processes for making substituted benzimidazoles.

SUMMARY OF THE INVENTION

The present invention relates to compounds of the Formula 1

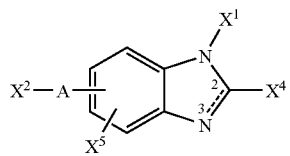

or a pharmaceutically acceptable salt or solvate thereof, wherein:

the dashed line designates that a double bond or a single bond connects the nitrogen at the three position with the carbon at the two position;

each A and A' is independently a direct bond, —C(O)N(R⁴)—, —N(R⁴)C(O)—, —N(R⁴)SO₂—, —SO₂N(R⁴)—, —N(R⁴)C(O)(CR⁴R⁵)ₚNHC(O)—, —N(R⁴)C(O)(CR⁴R⁵)ₚN(R⁴)—, —N(R⁴)C(S)(CR⁴R⁵)ₚN(R⁴)—, —N(R⁴)C(O)(CR⁴R⁵)ₚC(O)—, —N(R⁴)C(O)O—, —N(R⁴)C(O)S—, —C(O)—, —N(R³)—, —S— or —O—, wherein p is an integer from 0 to 5 and the left dash of the foregoing groups is attached to the benzimidazole ring of the compound of Formula 1;

X¹ is —(CR⁴R⁵)ₘ—C(A'-R¹ᵃ)(A-R¹)—(CR⁴R⁵)ₙCO₂H or —(CR⁴R⁵)ₘ—C(A-R¹)=C(R⁴)—(CR⁴R⁵)ₙ—CO₂H, wherein m and n are each independently an integer from 0 to 4 and the $(CR^4R^5)_m$ and $(CR^4R^5)_t$ moieties of the foregoing $X^1$ groups optionally include one or two carbon-carbon double or triple bonds;

$X^2$ is H, $C_1$-$C_{20}$ alkyl, $C_2$-$C_{20}$ alkenyl, $C_2$-$C_{20}$ alkynyl, —$(CR^4R^5)_t(C_3$-$C_{20}$ cycloalkyl), —$(CR^4R^5)_t(C_6$-$C_{10}$ aryl), or —$(CR^4R^5)_t$(4 to 12 membered heterocyclic), wherein each $X^2$ group, except H, is substituted by $X^3$, each t is independently an integer from 0 to 5, said alkyl, alkenyl and alkynyl groups optionally contain 1 or 2 hetero moieties selected from O, —S(O)$_j$— wherein j is an integer from 0 to 2, and —N(R$^4$)— with the proviso that two O atoms, two S atoms, or an O and S atom are not attached directly to each other, and the proviso that an O atom, a S atom or a N atom are not attached directly to a triple bond or non-aromatic double bond;

said cycloalkyl, aryl and heterocyclic $X^2$ groups are optionally fused to one or two ring systems independently selected from a benzene ring, a $C_5$-$C_8$ cycloalkyl group, and a 4 to 10 membered heterocyclic group;

—$(CR^4R^5)_t$— optionally includes a carbon-carbon double or triple bond where t is an integer from 2 to 5, or where t is 1 the —$(CR^4R^5)_t$— moiety of —$(CR^4R^5)_t$(4 to 12 membered heterocyclic and —$(CR^4R^5)_t(C_3$-$C_{20}$ cycloalkyl) optionally is attached by a carbon-carbon double bond to a carbon of the cycloalkyl group or a non-aromatic carbon of the 4 to 12 membered heterocyclic group;

said cycloalkyl optionally includes one or two carbon-carbon double or triple bonds;

and $X^2$, except when H, optionally is substituted by 1 to 5 $R^2$ groups;

$X^3$ is H or a functional group which forms biological interactions similar to those of the guanadinyl group (—NH(=NH)NH$_2$) present in the amino acid arginine such as 2-aminoimidazoyl, 2-aminobenzimidazoyl, 2-aminopyridyl, 2-aminopyrimidyl, 2-aminopyrazinyl and others disclosed in Keenan et al, *Bioorg. Med. Chem. Lett.*, 9(1999), 1801, incorporated herein by reference, wherein each of the foregoing $X^3$ groups, other than H, is optionally substituted by 1 or 2 $R^2$ groups;

$X^4$ is H, $C_1$-$C_{10}$ alkyl, —NR$^3$R$^4$, —SR$^3$, or —OR$^3$;

each $X^5$ and $R^2$ is independently selected from $C_1$-$C_{10}$ alkyl, $C_2$-$C_{10}$ alkenyl, $C_2$-$C_{10}$ alkynyl, oxo (=O), thioxo (=S), halo, cyano, nitro, trifluoromethyl, difluoromethoxy, trifluoromethoxy, azido, —OR$^3$, —C(O)R$^3$, —C(O)OR$^3$, —NR$^4$C(O)OR$^6$, —NR$^4$C(O)R$^3$, —OC(O)R$^3$, —NR$^4$SO$_2$R$^6$, —SO$_2$NR$^3$R$^4$, —NR$^4$C(O)R$^3$, —C(O)NR$^3$R$^4$, —O—N=CR$^3$R$^4$, —NR$^4$C(O)NR$^3$R$^4$, —NR$^4$C(S)NR$^3$R$^4$, —NR$^3$R$^4$, —S(O)$_j$(CR$^4$R$^5$)$_t$(C$_6$-C$_{10}$ aryl), —S(O)$_j$(CR$^4$R$^5$)$_t$(4 to 12 membered heterocyclic), —S(O)$_j$(C$_1$-C$_6$ alkyl), —(CR$^4$R$^5$)$_t$(C$_6$-C$_{10}$ aryl), —(CR$^4$R$^5$)$_p$C(O)(CR$^4$R$^5$)$_t$(C$_6$-C$_{10}$ aryl), —(R$^4$R$^5$)$_p$O(CR$^4$R$^5$)$_t$(C$_6$-C$_{10}$ aryl), —NR$^4$(CR$^4$R$^5$)$_t$(C$_6$-C$_{10}$ aryl), —(CR$^4$R$^5$)$_t$(4 to 12 membered heterocyclic), and —(CR$^4$R$^5$)$_p$C(O)(CR$^4$R$^5$)$_t$(4 to 12 membered heterocyclic), wherein each t is independently an integer from 0 to 5, each p is independently an integer from 0 to 5, and each j is an integer from 0 to 2; said alkyl, alkenyl and alkynyl groups optionally contain 1 or 2 hetero moieties selected from O, —S(O)$_j$— wherein j is an integer from 0 to 2, and —N(R$^3$)— with the proviso that two O atoms, two S atoms, or an O and S atom are not attached directly to each other, and the proviso that an O atom, a S atom or a N atom are not attached directly to a triple bond or a non-aromatic double bond; said cycloalkyl, aryl and heterocyclic R$^2$ groups are optionally fused to a C$_6$-C$_{10}$ aryl group, a C$_5$-C$_8$ cycloalkyl group, or a 4 to 12 membered heterocyclic group; and said alkyl, alkenyl, alkynyl, aryl and heterocyclic moieties of the foregoing R$^2$ groups are optionally substituted by 1 to 5 substituents independently selected from oxo (=O), thioxo (=S), halo, cyano, nitro, trifluoromethyl, difluoromethoxy, trifluoromethoxy, azido, —NR$^4$SO$_2$R$^6$, —SO$_2$NR$^3$R$^4$, —C(O)R$^3$, —C(O)OR$^3$, —OC(O)R$^3$, —NR$^4$C(O)OR$^6$, —NR$^4$C(O)R$^3$, —C(O)NR$^3$R$^4$, —NR$^3$R$^4$, —OR$^3$, C$_1$-C$_{10}$ alkyl, —S(O)$_j$(C$_1$-C$_6$ alkyl), —(CR$^4$R$^5$)$_t$(C$_6$-C$_{10}$ aryl), and —(CR$^4$R$^5$)$_t$(4 to 12 membered heterocyclic), wherein each t is independently an integer from 0 to 5 and each j is independently an integer from 0 to 2;

each $R^1$ and $R^{1a}$ is independently selected from H, $C_1$-$C_{10}$ alkyl, $C_2$-$C_{10}$ alkenyl, $C_2$-$C_{10}$ alkynyl, —(CR$^4$R$^5$)$_t$(C$_6$-C$_{10}$ aryl) and —(CR$^4$R$^5$)$_t$(4 to 12 membered heterocyclic); wherein t is an integer from 0 to 5; and $R^1$, except when H, is optionally substituted with 1 to 5 $R^2$ groups;

each $R^3$ is independently selected from H, $C_1$-$C_{10}$ alkyl, —(CR$^4$R$^5$)$_t$(C$_6$-C$_{10}$ aryl), and —(CR$^4$R$^5$)$_t$(4 to 12 membered heterocyclic), wherein each t is independently an integer from 0 to 5; said alkyl group optionally includes 1 or 2 hetero moieties selected from O, —S(O)$_j$— wherein j is an integer ranging from 0 to 2, and —N(R$^4$)— with the proviso that two O atoms, two S atoms, or an O and S atom are not attached directly to each other; said cycloalkyl, aryl and heterocyclic R$^3$ groups are optionally fused to a C$_6$-C$_{10}$ aryl group, a C$_5$-C$_8$ cycloalkyl group, or a 4 to 12 membered heterocyclic group; and R$^3$, except when H, is optionally substituted by 1 to 5 substituents independently selected from oxo, halo, cyano, nitro, trifluoromethyl, difluoromethoxy, trifluoromethoxy, azido, —C(O)R$^4$, —C(O)OR$^4$, —OC(O)R$^4$, —NR$^4$C(O)R$^5$, —C(O)NR$^4$R$^5$, —NR$^4$R$^5$, hydroxy, C$_1$-C$_6$ alkyl, trifluoromethyl, trifluoromethoxy, and C$_1$-C$_6$ alkoxy, and with the proviso that R$^3$ must be attached through a carbon atom unless R$^3$ is H;

each $R^4$ and $R^5$ is independently H or C$_1$-C$_6$ alkyl; or where R$^4$ and R$^5$ are attached to the same carbon atom, R$^4$ and R$^5$ may be taken together to form a C$_3$-C$_{10}$ cycloalkyl group;

each $R^6$ is independently selected from C$_1$-C$_{10}$ alkyl, —(CR$^4$R$^5$)$_t$(C$_6$-C$_{10}$ aryl), and —(CR$^4$R$^5$)$_t$(4 to 12 membered heterocyclic), wherein each t is independently an integer from 0 to 5; said alkyl group optionally includes 1 or 2 hetero moieties selected from O, —S(O)$_j$— wherein j is an integer ranging from 0 to 2, and —N(R$^4$)— with the proviso that two O atoms, two S atoms, or an O and S atom are not attached directly to each other; said cycloalkyl, aryl and heterocyclic R$^6$ groups are optionally fused to a C$_6$-C$_{10}$ aryl group, a C$_5$-C$_8$ cycloalkyl group, or a 4 to 12 membered heterocyclic group; and R$^6$ is optionally substituted by 1 to 5 substituents independently selected from oxo, halo, cyano, nitro, trifluoromethyl, difluoromethoxy, trifluoromethoxy, azido, —C(O)R$^4$, —C(O)OR$^4$, —OC(O)R$^4$, —NR$^4$C(O)R$^5$, —C(O)NR$^4$R$^5$, —NR$^4$R$^5$, hydroxy, C$_1$-C$_6$ alkyl, trifluoromethyl, trifluoromethoxy, and C$_1$-C$_6$ alkoxy.

In a specific embodiment of the present invention, the A moiety in -A-X$^2$ is selected from a direct bond, —C(O)NH—, —NHC(O)—, —SO$_2$NH—, —NHSO$_2$—, —NHC(O)NH—, and —NHC(S)NH—.

In another specific embodiment of the present invention, X$^1$ is selected from —CH$_2$—CH(AR$^1$)—CO$_2$H, —CH(AR$^1$)—CH$_2$—CO$_2$H, —CH(AR$^1$)—CO$_2$H, —C(AR$^1$)(A'R$^{1a}$)—CH$_2$—CO$_2$H, —CH$_2$—C(AR$^1$)(A'R$^{1a}$)—CO$_2$H, —C(AR$^1$)(A'R$^{1a}$)—CO$_2$H and —C(AR$^1$)=CHCO$_2$H.

In another specific embodiment of the present invention, -A-X$^2$ and X$^5$ are both H, the dashed line in Formula 1 between the nitrogen at the three position and carbon at the two position designates a double bond, X$^4$ is H, and X$^1$ is —C(AR$^1$)(A'R$^{1a}$)—CH$_2$—CO$_2$H. More specifically, such compounds include those wherein X$^1$ is —CH(AR$^1$)—CH$_2$—CO$_2$H. More specifically, such compounds also include those wherein $X^1$ is —CH(AR$^1$)—CH$_2$—CO$_2$H, A is a direct bond or —CH$_2$—, and R$^1$ is phenyl optionally substituted by 1 or 2 R$^2$ groups.

In another specific embodiment of the present invention, -A-X$^2$ is —NHC(O)X$^2$, X$^5$ is H, the dashed line in Formula 1 between the nitrogen at the three position and carbon at the two position designates a double bond, X$^4$ is H, and X$^1$ is —CH(AR$^1$)—CH$_2$—CO$_2$H in which A is a direct bond or —CH$_2$—, and R$^1$ is phenyl optionally substituted by 1 or 2 R$^2$ groups. More specifically, X$^2$ is phenyl optionally substituted by 1 to 4 R$^2$ groups. More specifically, X$^2$ is pyridyl optionally substituted by 1 to 3 R$^2$ groups.

In another specific embodiment of the present invention, the dashed line in Formula 1 between the nitrogen at the three position and carbon at the two position designates a double bond, X$^4$ is H, and X$^1$ is —CH(AR$^1$)—CH$_2$—CO$_2$H in which A is a direct bond or —CH$_2$—, and R$^1$ is pyridyl, naphthyl, or phenyl optionally substituted by 1 or 2 R$^2$ groups, and X$^5$ is selected from nitro, —NR$^3$R$^4$, and —NR$^4$SO$_2$R$^6$. More specifically X$^5$ is selected from nitro, amino and phenylsulfonylamino.

In another specific embodiment of the present invention, X$^3$ is selected from H, C$_1$-C$_6$ alkyl, C$_3$-C$_{12}$ cycloalkyl, 5 to 12 membered heterocyclic, and guanidine group mimetics, and said groups, other than H, are optionally substituted by R$^2$;

Preferred compounds include those selected from the group consisting of:
3-(1H-Benzimidazol-1-yl)-3-(4-ethylphenyl)propanoic acid;
3-Phenyl-3-[6-(trifluoromethyl)-1H-benzimidazol-1-yl]propanoic acid;
(3R)-3-(1H-Benzimidazol-1-yl)-3-phenylpropanoic acid;
(3S)-3-(1H-Benzimidazol-1-yl)-4-phenylbutanoic acid;
3-(1H-Benzimidazol-1-yl)-3-(4-chlorophenyl)propanoic acid;
3-Phenyl-3-(4-{4-[(1,4,5,6-tetrahydro-2-pyrimidinylamino)carbonyl]-1-piperidinyl}-1H-benzimidazol-1-yl)propanoic acid;
3-{5-[(3-Nitrobenzoyl)amino]-1H-benzimidazol-1-yl}-3-phenylpropanoic acid;
3-{5-[(3-Aminobenzoyl)amino]-1H-benzimidazol-1-yl}-3-phenylpropanoic acid;
3-{5-[(3-{[Amino(imino)methyl]amino}benzoyl)amino]-1H-benzimidazol-1-yl}-3-phenylpropanoic acid;
3-{5-[(4-{[Amino(imino)methyl]amino}benzoyl)amino]-1H-benzimidazol-1-yl}-3-phenylpropanoic acid;
3-{5-[(Anilinocarbonyl)amino]-1H-benzimidazol-1-yl}-3-phenylpropanoic acid;
3-{5-[(2-Phenoxybenzoyl)amino]-1H-benzimidazol-1-yl}-3-phenylpropanoic acid;
3-{5-[(2,6-Dimethoxybenzoyl)amino]-1H-benzimidazol-1-yl}-3-phenylpropanoic acid;
3-Phenyl-3-[5-({[2-(phenylsulfanyl)-3-pyridinyl]carbonyl}amino)-1H-benzimidazol-1-yl]propanoic acid;
3-(5-{[(2-Phenoxy-3-pyridinyl)carbonyl]amino}-1H-benzimidazol-1-yl)-3-phenylpropanoic acid;
3-{5-[(2-Hydroxy-5-nitrobenzoyl)amino]-1H-benzimidazol-1-yl}-3-phenylpropanoic acid;
3-{6-[(2-aminobenzoyl)amino]-1H-benzimidazol-1-yl}-3-phenylpropanoic acid;
3-(6-{[3-(1H-Indol-3-yl)propanoyl]amino}-1H-benzimidazol-1-yl)-3-phenylpropanoic acid;
3-Phenyl-3-[6-({[2-(phenylsulfanyl)-3-pyridinyl]carbonyl}amino)-1H-benzimidazol-1-yl]propanoic acid;
3-{6-[(2-Bromo-5-methoxybenzoyl)amino]-1H-benzimidazol-1-yl}-3-phenylpropanoic acid;
3-Phenyl-3-(6-{[(4-phenyl-1,2,3-thiadiazol-5-yl)carbonyl]amino}-1H-benzimidazol-1-yl)propanoic acid;
3-{6-[(3-Bromo-2,6-dimethoxybenzoyl)amino]-1H-benzimidazol-1-yl}-3-phenylpropanoic acid
3-Phenyl-3-{6-[(2,3,5-trichloro-6-hydroxybenzoyl)amino]-1H-benzimidazol-1-yl}propanoic acid;
3-(5-Nitro-1H-benzimidazol-1-yl)-3-(3-pyridinyl)propanoic acid;
3-(5-Amino-1H-benzimidazol-1-yl)-3-(3-pyridinyl)propanoic acid;
3-{5-[(Phenylsulfonyl)amino]-1H-benzimidazol-1-yl}-3-(3-pyridinyl)propanoic acid;
3-(2-Naphthyl)-3-(5-nitro-1H-benzimidazol-1-yl)propanoic acid;
3-(5-Amino-1H-benzimidazol-1-yl)-3-(2-naphthyl)propanoic acid;
3-(2-Naphthyl)-3-{5-[(phenylsulfonyl)amino]-1H-benzimidazol-1-yl}propanoic acid
3-(5-Amino-1H-benzimidazol-1-yl)-3-(4-methoxyphenyl)propanoic acid;
3-(4-Methoxyphenyl)-3-{5-[(phenylsulfonyl)amino]-1H-benzimidazol-1-yl}propanoic acid;
1-(2-Carboxy-1-phenylethyl)-1H-benzimidazole-5-carboxylic acid;
3-[5-(Anilinocarbonyl)-1H-benzimidazol-1-yl]-3-phenylpropanoic acid;
3-Phenyl-3-(5-{[4-(2-pyrazinyl)-1-piperazinyl]carbonyl}-1H-benzimidazol-1-yl) propanoic acid;
and the pharmaceutically acceptable salts or solvates of the foregoing compounds.

This invention also relates to a method for the treatment of abnormal cell growth in a mammal, including a human, comprising administering to said mammal an amount of a compound of the Formula 1, as defined above, or a pharmaceutically acceptable salt or solvate thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a compound of Formula 1, or a pharmaceutically acceptable salt or solvate thereof, that is effective in treating abnormal cell growth in combination with an anti-tumor agent selected from the group consisting of mitotic inhibitors, alkylating agents, antimetabolites, intercalating antibiotics, growth factor inhibitors, cell cycle inhibitors, enzymes, topoisomerase inhibitors, biological response modifiers, antibodies, cytotoxics, anti-hormones, and anti-androgens.

The invention also encompasses a pharmaceutical composition that is comprised of a compound of Formula 1 in combination with a pharmaceutically acceptable carrier.

Preferably the composition is comprised of a pharmaceutically acceptable carrier and a non-toxic therapeutically effective amount of a compound of Formula 1 as described above (or a pharmaceutically acceptable salt thereof).

This invention also relates to a pharmaceutical composition for the treatment of abnormal cell growth in a mammal, including a human, comprising a non-toxic therapeutically effective amount of a compound of the Formula 1, as described above, or a pharmaceutically acceptable salt or solvate thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

The invention also relates to a pharmaceutical composition for the treatment of abnormal cell growth in a mammal, including a human, which comprises an amount of a compound of Formula 1, as defined above, or a pharmaceutically acceptable salt or solvate thereof, that is effective in treating abnormal cell growth in combination with a pharmaceutically acceptable carrier and an anti-tumor agent selected from the group consisting of mitotic inhibitors, alkylating agents, antimetabolites, intercalating antibiotics, growth factor inhibitors, cell cycle inhibitors, enzymes, topoisomerase inhibitors, biological response modifiers, anti-hormones, and anti-androgens.

This invention also relates to a method for the treatment of a disorder associated with angiogenesis in a mammal, including a human, comprising administering to said mammal an amount of a compound of the Formula 1, as defined above, or a pharmaceutically acceptable salt or solvate thereof, that is effective in treating said disorder. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi, Yersinia* spp., *Bordetella pertussis*, and group A *Streptococcus*.

This invention also relates to a method of (and to a pharmaceutical composition for) treating abnormal cell growth in a mammal which comprise an amount of a compound of Formula 1, or a pharmaceutically acceptable salt or solvate thereof, and an amount of one or more substances selected from anti-angiogenesis agents, signal transduction inhibitors, and antiproliferative agents, which amounts are together effective in treating said abnormal cell growth.

This invention includes a composition comprising a compound according to Formula 1, or a pharmaceutically acceptable salt or N-oxide thereof; and a pharmaceutically acceptable carrier.

This invention includes a composition comprising a compound according to Formula 1, or a pharmaceutically acceptable salt or N-oxide thereof; and an anti-neoplastic, anti-tumor, anti-angiogenic, or chemotherapeutic agent.

This invention includes a composition comprising a compound according to Formula 1, or a pharmaceutically acceptable salt or N-oxide thereof; and a cytotoxic cancer therapeutic agent.

This invention includes a composition comprising a compound according to Formula 1, or a pharmaceutically acceptable salt or N-oxide thereof; and an angiogenesis inhibiting cancer therapeutic agent.

This invention includes a method of treatment of hyperproliferative disorder comprising a step of administering an effective amount of the compound according to Formula 1.

This invention includes a method treatment of hyperproliferative disorder comprising a step of administering an effective amount of the compound according to Formula 1, further comprising the step of administering an anti-neoplastic, anti-tumor, anti-angiogenic, or chemotherapeutic agent.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of Formula 1 in the methods and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in combination with the compounds of the present invention are AG-3340, RO 32-3555, RS 13-0830, and the compounds recited in the following list:
3-[[4-(4-fluoro-phenoxy)-benzenesulfonyl]-(1-hydroxycarbamoyl-cyclopentyl)-amino]-propionic acid;
3-exo-3-[4-(4-fluoro-phenoxy)-benzenesulfonylamino]-8-oxa-bicyclo[3.2.1]octane-3-carboxylic acid hydroxyamide;
(2R,3R) 1-[4-(2-chloro-4-fluoro-benzyloxy)-benzenesulfonyl]-3-hydroxy-3-methyl-piperidine-2-carboxylic acid hydroxyamide;
4-[4-(4-fluoro-phenoxy)-benzenesulfonylamino]-tetrahydro-pyran-4-carboxylic acid hydroxyamide;
3-[[4-(4-fluoro-phenoxy)-benzenesulfonyl]-(1-hydroxycarbamoyl-cyclobutyl)-amino]-propionic acid;
4-[4-(4-chloro-phenoxy)-benzenesulfonylamino]-tetrahydro-pyran-4-carboxylic acid hydroxyamide;
3-[4-(4-chloro-phenoxy)-benzenesulfonylamino]-tetrahydro-pyran-3-carboxylic acid hydroxyamide;
(2R,3R) 1-[4-(4-fluoro-2-methyl-benzyloxy)-benzenesulfonyl]-3-hydroxy-3-methyl-piperidine-2-carboxylic acid hydroxyamide;
3-[[4-(4-fluoro-phenoxy)-benzenesulfonyl]-(1-hydroxycarbamoyl-1-methyl-ethyl)-amino]-propionic acid;
3-[[4-(4-fluoro-phenoxy)-benzenesulfonyl]-(4-hydroxycarbamoyl-tetrahydro-pyran-4-yl)-amino]-propionic acid;
3-exo-3-[4-(4-chloro-phenoxy)-benzenesulfonylamino]-8-oxa-bicyclo[3.2.1]octane-3-carboxylic acid hydroxyamide;
3-endo-3-[4-(4-fluoro-phenoxy)-benzenesulfonylamino]-8-oxa-bicyclo[3.2.1]octane-3-carboxylic acid hydroxyamide; and
3-[4-(4-fluoro-phenoxy)-benzenesulfonylamino]-tetrahydro-furan-3-carboxylic acid hydroxyamide;
and pharmaceutically acceptable salts or solvates of said compounds.

The compounds of Formula 1, and the pharmaceutically acceptable salts or solvates thereof, can also be used in combination with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents include, but are not limited to, the monoclonal antibodies C225 and anti-EGFR 22 Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

VEGF inhibitors, for example SU-5416 and SU-6668 (Sugen Inc. of South San Francisco, Calif., USA), can also be combined with a compound of Formula 1. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with a compound of Formula 1. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety.

A compound of Formula 1 may also be used with other agents useful in treating abnormal cell growth or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present invention include those described in U.S. Provisional Application 60/113,647 (filed Dec. 23, 1998) which is herein incorporated by reference in its entirety.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The term "halo", as used herein, unless otherwise indicated, includes fluoro, chloro, bromo or iodo. Preferred halo groups are fluoro and chloro.

The term "alkyl", as used herein, unless otherwise indicated, includes saturated monovalent hydrocarbon radicals having straight, cyclic (including mono- or multi-cyclic moieties) or branched moieties. It is understood that for said alkyl group to include cyclic moieties it must contain at least three carbon atoms.

The term "cycloalkyl", as used herein, unless otherwise indicated, includes saturated monovalent hydrocarbon radicals having cyclic (including mono- or multi-cyclic) moieties.

The term "alkenyl", as used herein, unless otherwise indicated, includes alkyl groups, as defined above, having at least one carbon-carbon double bond.

The term "alkynyl", as used herein, unless otherwise indicated, includes alkyl groups, as defined above, having at least one carbon-carbon triple bond.

The term "aryl", as used herein, unless otherwise indicated, includes an organic radical derived from an aromatic hydrocarbon by removal of one hydrogen, such as phenyl or naphthyl.

The term "alkoxy", as used herein, unless otherwise indicated, includes —O-alkyl groups wherein alkyl is as defined above.

The term "4 to 12 membered heterocyclic", as used herein, unless otherwise indicated, includes aromatic and non-aromatic heterocyclic groups containing one or more heteroatoms each selected from O, S and N, wherein each heterocyclic group has from 4 to 12 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached). The terms "5 to 12 membered heterocyclic", "5 to 6 membered heterocyclic", and other uses of "heterocyclic", correspond to the above definition with an appropriate number of ring members.

The term "Me" means methyl, "Et" means ethyl, and "Ac" means acetyl.

In the definition of $X^1$ above, the $(CR^4R^5)_m$ and $(CR^4R^5)_n$ moieties of the foregoing $X^1$ groups optionally include one or two carbon-carbon double or triple bonds where m or n are an integer from 2 to 4. This means that these moieties may be, for instance, —C($R^4$)=C($R^5$)— where n or m is 2, —C($R^4$)=C($R^5$)C$R^4R^5$— or —C$R^4R^5$C($R^4$)=C($R^5$)— where m or n is 3, —C≡C— when m or n is 2, and so on.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium slats. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylameine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

Certain functional groups contained within the compounds of the present invention can be substituted for bioisosteric groups, that is, groups which have similar spatial or electronic requirements to the parent group, but exhibit differing or improved physicochemical or other properties. Suitable examples are well known to those of skill in the art, and include, but are not limited to moieties described in Patini et al., Chem. Rev, 1996, 96, 3147-3176 and references cited therein.

Compounds described herein contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all optical isomers and stereoisomers of Formula I, and mixtures thereof and pharmaceutically acceptable salts thereof, and to all pharmaceutical compositions and methods of treatment that may employ or contain them. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers. The compounds of Formula 1 may also exist as tautomers. This invention relates to the use of all such tautomers and mixtures thereof.

The subject invention also includes isotopically-labelled compounds, and the pharmaceutically acceptable salts or solvates thereof, which are identical to those recited in Formula 1 but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$ $^{35}S$, $^{18}F$, and $^{36}Cl$, respectively. Compounds of the present invention and pharmaceutically acceptable salts of said compounds which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$; can afford certain therapeutic advantages resulting from greater metabolic stability, for example increased in vivo half-life or reduced dosage requirements and, hence, may be preferred in some circumstances. Isotopically labelled compounds of Formula 1 of this invention can generally be prepared by carrying out the procedures disclosed in the Schemes and/or in the Examples and Preparations below, by substituting a readily available isotopically labelled reagent for a non-isotopically labelled reagent.

DETAILED DESCRIPTION OF THE INVENTION

The following general reaction schemes outline the synthetic routes which may be used to prepare the compounds of the present invention. In the Schemes below, substituents that correspond to those used above with respect to the compound of Formula 1 are defined as provided above unless otherwise indicated. The "Y" substituents are used below where specific moieties are described that do not correspond exactly to the defined variables used for Formula 1 above but fall within the scope of the invention described above.

1. Simple Benzimidazoles

Two preferred routes to these compounds are described below.

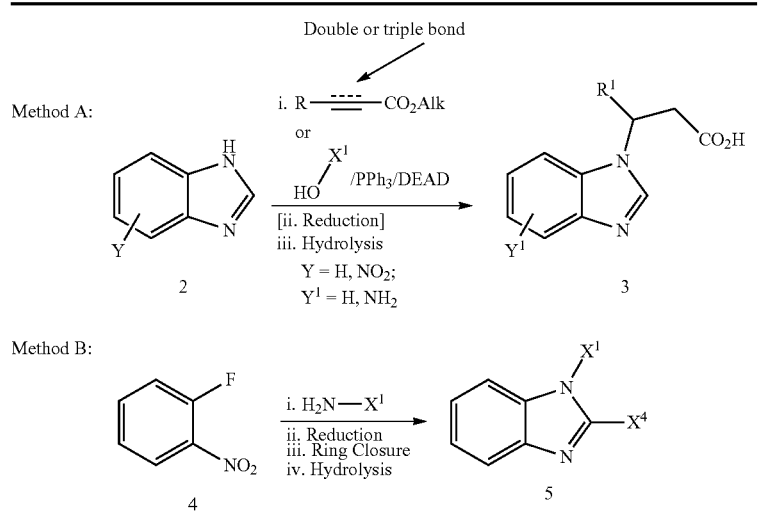

In the above illustrated method A, reaction of the benzimidazole core with a variety of electrophilic reagents can be carried out. Examples of suitable electrophiles include acrylates and propiolates (in conjunction with a suitable base, such as sodium methoxide or potassium carbonate), or activated alcohol derivatives, for example in a Mitsunobu type reaction. Amine nucleophiles suitable for use in method B, step i include, but are not limited to, α- or β-amino acid derivatives in the presence of an appropriate base, such as triethylamine, or potassium carbonate. Suitable reducing conditions, such as those employed in method A, step ii, or method B step ii are a reactive metal catalyst, for example, palladium on carbon, Raney-nickel etc., and a source of hydrogen (for example, the gaseous element, or using transfer from materials such as hydrazine, ammonium formate or cyclohexene). Other suitable reduction methods would be readily apparent to those of skill in the art. In the above illustrated method B, step iii, ring closure may be effected using a variety of protocols, for example, where $X^4$=H, an orthoester such as triethylorthoformate may be used, or formamidine acetate. Where $X^4$ is alkyl, for example a methyl group, a reagent such as acetic anhydride, or an acetamidine salt would be suitable.

In the above illustrated methods A and B, hydrolysis of a carboxylic acid ester may be accomplished using acidic (for example, dilute hydrochloric acid) or basic (for example, dilute sodium hydroxide) reaction conditions. In method A, regarding the $X^1$ moiety illustrated, $R^1$ has been incorporated at C-1' (i.e. m=0, n=1 in $X^1$; —CHR$^1$—CH$_2$—CO$_2$H). Other compounds include those where m or n have other values including analogues substituted at C-2' (i.e. m=1, n=0; CH$_2$—CHR$^1$—CO$_2$H).

2. 4-Substituted Benzimidazoles

A preferred route for preparing these analogues is shown below.

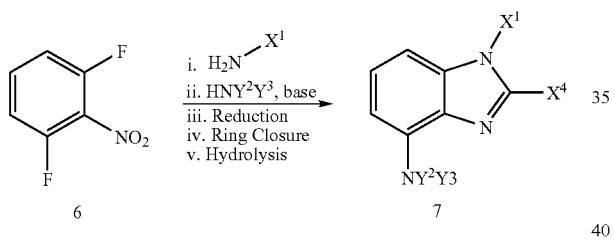

Notes: HNY$^2$Y$^3$ is typically a cycloamine, e.g. piperidine; $X^1$ is as defined above.

The above illustrated reaction scheme utilises reaction conditions that have been described previously, for example, nucleophilic addition of a suitable amine, reduction, ring closure etc. Other techniques familiar to those skilled in the art are referred to in WO 97/10219.

3. Other Substituted Benzimidazoles

The following generic procedures are illustrative examples of synthetic routes which are suitable for preparing the compounds described in the current invention. Appropriate solvents, temperatures and other experimental conditions are not specifically stated, but would be readily apparent. While being representative, the following procedures are not intended to be comprehensive, and alternatives would be readily apparent to those of skill in the art. For example, in Method C, the carboxylic acid group of compound 14 could be replaced by a sulfonic acid, or suitable derivative. Likewise, more heavily substituted benzimidazoles could be prepared by utilisation of a more densely functionalised starting material.

Starting chemicals, if not available from a commercial supplier can be readily prepared according to procedures well known to those skilled in the art.

Method D:

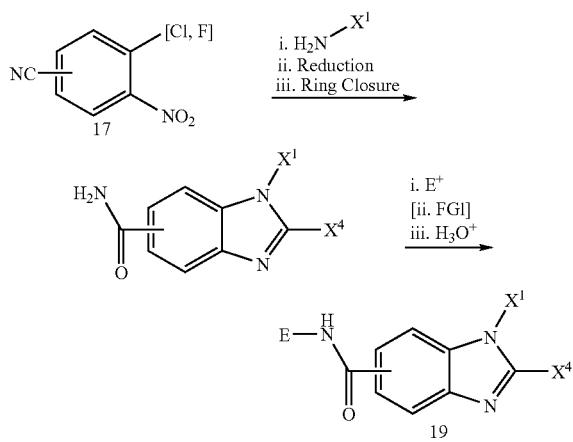

Method E:

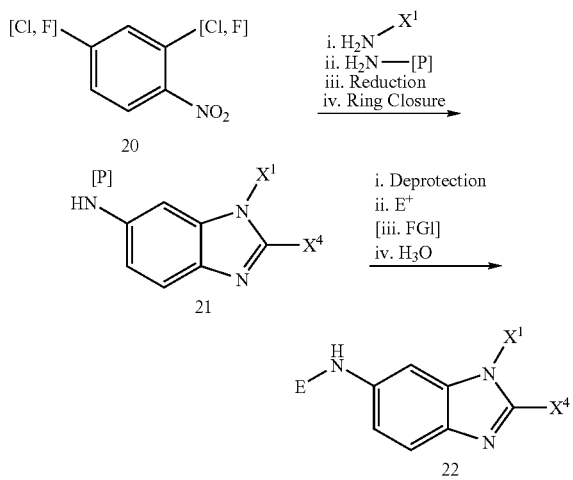

Method F:

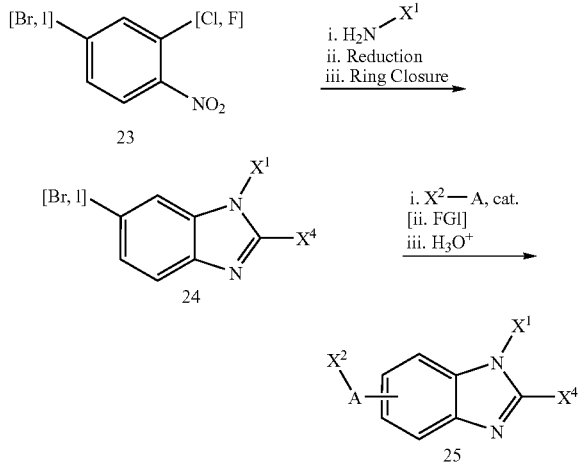

In the above illustrated method A, reduction of the adduct derived from compound 8 and the propiolate ester can be accomplished using similar conditions to those already described. In the transformation of compound 9 to 10, 12 to 13, 18 to 19 and 21 to 22 examples of suitable electrophiles ($E^+$) could include (but are not limited to) reagents such as phenyl isocyanate (to form the corresponding urea), phenyl thioisocyanate (thiourea), an activated carboxylic acid derivative (activated using a reagent such as DCC, or HATU, to form the corresponding amide), a sulfonyl chloride (to form the corresponding sulfonamide), or using an in situ procedure such as reductive amination (using an carbonyl species in conjunction with a suitable reducing agent such as sodium cyanoborohydride, to generate a homologated amine). FGI refers to Functional Group Interconversions. Thus, a nitro-group within group E in compounds 10 and 13 (for example) may be subsequently reduced to an amino-group using conditions similar to those already described. Further transformations can be carried out on the thus generated amine, if so desired. Other suitable examples would be readily apparent.

For the transformation of compounds 11 to 12, 14 to 15, 17 to 18, 20 to 21 and 23 to 24 suitable conditions have already been outlined for the nucleophilic addition of an amine, reduction, and ring closure steps.

In compound 15, AG refers to an activating group for a carboxylic acid, such that it may undergo a ready displacement reaction with a suitable nucleophile ($Nu^-$). Examples of activating protocols are numerous, and include (but are not limited to), conversion to the corresponding carboxylic acid chloride (or other halide), reaction with reagents such as DCC, HATU etc. Suitable nucleophiles include (but are not limited to) primary and secondary amines, thiols, alcohols, phenols, thiophenols etc. Other examples would be readily apparent. A reference that relates to compounds of the structure 15 or 16 is German patent DD 123,466 (Dec. 20, 1976).

In the above illustrated method F, the conversion of compound 24 to 25 is representative of classes of reactions that are well known to occur with suitable aryl halides and suitable coupling partners, including (but not limited to) boronic acids, trialkylstannanes, and amines (aliphatic and aromatic), under catalysis by an appropriate transition metal catalyst, such as tetrakistriphenylphosphine palladium (0). Other reactions of this type, coupling partners and catalysts would be readily apparent.

In principle, Method C could be used to prepare the analogous 6-carboxylic acid isomers, and the corresponding 5- and 6-sulfonamido-substituted compounds, by judicious choice of starting material.

The compounds of the present invention may have asymmetric carbon atoms. Diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

The compounds of Formula 1 that are basic in nature are capable of forming a wide variety of different salts with various inorganic and organic acids. Although such salts must be pharmaceutically acceptable for administration to animals, it is often desirable in practice to initially isolate the compound of Formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of Formula 1 that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of Formula 1. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product. Since a single compound of the present invention may include more than one acidic or basic moieties, the compounds of the present invention may include mono, di or tri-salts in a single compound.

The compounds of the present invention are potent inhibitors of the integrin family of transmembrane receptors involved in cell adhesion, and thus are all adapted to therapeutic use as anti-angiogenic agents (e.g., disorders characterised by inappropriate vascularisation, for example tumour associated angiogenesis which is a pre-requisite for tumour cell growth, proliferation and metastasis) in mammals, particularly in humans. In particular, the compounds of the present invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the skin (e.g., psoriasis) and benign hyperplasia of the prostate (e.g., BPH). It is, in addition, expected that a compound of the present invention may possess activity against a range of leukemias and lymphoid malignancies.

The activity of the compounds of Formula 1 may be determined by the following procedures.

Assays to Measure Integrin/Ligand Interactions $\alpha_v\beta_3$, $\alpha_v\beta_5$/Vitronectin Binding Assays Human $\alpha_v\beta_3$ was purified from extracts of placenta tissue based on affinity chromatography techniques employing monoclonal antibody LM609 [Pytela et al., *Methods Enzymol.* (1987), 144, 475-489; Smith and Cheresh, *J. Biol. Chem.*, (1988), 263, 18726-18731]. The purified integrin was aliquoted and stored at −70° C. in PBS containing 0.1% NP-40 and 2 mM $CaCl_2$. Twelve to twenty-four hours prior to compound testing, an aliquot was thawed and diluted to 0.3 µg/mL protein in "binding buffer," a buffer composed of 50 mM Tris-HCl, pH 7.4, containing 100 mM NaCl, 1 mM $CaCl_2$, 1 mM $MgCl_2$ and 1 mM $MnCl_2$. Alternatively, a "low $Mn^{2+}$" binding buffer containing 0.002 mM $MnCl_2$ was used, in order to assess vitronectin binding to $\alpha_v\beta_3$ in an altered conformation state [e.g. Smith et al., *J. Biol. Chem.*, (1994), 269, 960-967; Kirchhofer et al., *J. Biol. Chem.*, (1990), 265, 18525-18530]. 100 µL Of the diluted $\alpha_v\beta_3$ protein was added to wells of the assay plates (Falcon™ Pro-Bind 96-well polystyrene plates; Becton Dickinson, Inc., Franklin Lakes, N.J.). Wells D1 to D6 received binding buffer only, and served as control wells for the assessment of nonspecific binding of the vitronectin and/or reporter antibody. Plates were incubated at 4° C. for 12 to 24 hours, at which time wells were aspirated completely. The wells were washed once with 250 µL of binding buffer containing 0.04% Tween-20 (binding buffer/Tween-20; ICN Biomedicals, Inc., Aurora, Ohio), followed by the addition of 250 µL per well of a blocking solution composed of binding buffer/Tween-20 containing 1% casein (Sigma Chemical Co., St. Louis, Mo.). The blocking solution is prepared at least 12 hours prior to use, to allow for complete dissolution of the casein. After incubation of the plates at room temperature for 1 hour, wells were aspirated and washed twice with 250 µL binding buffer/Tween-20. The wells were then aspirated completely and 40 µL of binding buffer/Tween-20 was added prior to compound addition.

Compounds were resuspended in 100% DMSO to yield stock concentrations of 1 to 10 mM. A compound plate was prepared by adding 10 µL of the stock compounds to 190 µL of deionized water, in duplicate wells of a 96-well U-bottom plate (Falcon™ 3910). One row was reserved for each compound (six concentrations in duplicates), except for row D, which contained 5% DMSO/95% water only. One-to-four-fold serial dilutions were prepared by transferring 50 µL of the first well concentration to 150 µL of 5% DMSO/95% water in the adjacent two wells. After completion of the various dilutions of the compounds in the compound plates, 10 µL of each compound solution was transferred to the corresponding wells in the assay plates containing 40 µL binding buffer/Tween-20.

Human vitronectin from plasma (Collaborative Biomedical Products, Bedford, Mass.) was resuspended at 0.5 mg/ml in binding buffer/Tween-20, for 12 to 18 hours at room temperature without stirring. Aliquots were prepared and frozen at −70° C. Aliquots were thawed as needed and the vitronectin was diluted to 50 ng/mL in binding buffer/Tween-20. 50 µL of this solution was then transferred to assay plates containing integrin and the various dilutions of compounds. Assay plates were incubated at room temperature for 15 minutes to allow vitronectin binding in the presence or absence of compounds. Wells were washed extensively (6 times) with 250 µL binding buffer/Tween-20 and aspirated. To detect the bound vitronectin, a horseradish peroxidase (HRP)-conjugated, sheep anti-vitronectin antibody (K90111B, Biodesign International, Kennebunk, Me.) was diluted 1:2000 in binding buffer/Tween-20 containing 2% BSA (Sigma, St. Louis, Mo.). 100 µL Of antibody solution was transferred to each well in the assay plates, followed by incubation at room temperature for 90 minutes and 6× washing with 250 µL binding buffer/Tween-20. After the final wash, wells were aspirated completely. The bound anti-vitronectin conjugate was detected by adding 100 µL of TMB peroxidase substrate solution (Kirkegaard and Perry Laboratories, Gaithersburg, Md.). Color development was stopped after 20 minutes by the addition of 100 µL of 0.18 M $H_2SO_4$. The colorimetric signal was quantitated at a wavelength of 450 nm using an EL340 Bio Kinetics Reader (Bio-Tek Instruments, Inc). The $IC_{50}$ (concentration of the compound to inhibit 50% of the specific binding of vitronectin to integrin) and standard errors were determined by a nonlinear, least squares curve fitting routine.

Interactions between a second vitronectin receptor, integrin $\alpha_v\beta_5$ [Smith et al., *J. Bio. Chem.*, (1990), 265, 11008-11013] and vitronectin were measured using the same assay format utilized for $\alpha_v\beta_3$. Purified human $\alpha_v\beta_5$ (octyl-β-D-glucopyranoside formulation) was obtained from Chemicon International, Inc. (Temecula, Calif.) and diluted in binding buffer. Most experiments utilized integrin $\alpha_v\beta_5$ at a concentration of 0.6 µg/mL, which produced a vitronectin-binding signal roughly equivalent to $\alpha_v\beta_3$ at 0.3 µg/mL.

Purification of Human $\alpha_{IIb}\beta_3$ (GPIIb-IIIa).

Ten units of outdated platelets were purchased from Long Island Blood Services (Melville, N.Y.). The platelets were pelleted and washed three times in 20 mM Tris-HCl, pH 7.2, containing 150 mM NaCl and 1 mM EDTA. Pelleted platelets could be frozen at −70° C. until needed. The equivalent of 5 units was thawed and suspended in a lysis buffer composed of 20 mM Tris-HCl, pH 7.4, containing 140 mM NaCl, 2 mM $CaCl_2$ and 3% octylglucoside. The platelet lysate was gently stirred for 2 hours at 4° C. followed by centrifugation at 100,000×g for one hour at 4° C. in a Beckman SW28 rotor. A lectin gel (5 mL) composed of purified *Lens culinaris* lectin covalently linked to agarose beads (E-Y Laboratories, Inc., San Mateo, Calif.) was equilibrated with equilibration buffer (composed of 20 mM Tris-HCl, pH 7.4, containing 100 mM NaCl, 2 mM $CaCl_2$ and 1% octylglucoside). The platelet lysate was gently stirred with the lectin gel for 2 hours at 4° C. The mixture was poured into a column, which was washed with 100 mL of the equilibration buffer. The bound $\alpha_{IIb}\beta_3$ was eluted, first with equilibration buffer containing 10% dextrose, followed by equilibration buffer containing 0.1M D-mannose. Fractions that were >75% pure, as estimated on silver stained gels, were pooled and dialyzed versus phosphate buffered saline (PBS) containing 1 mM $CaCl_2$, 1 mM $MnCl_2$ and 0.1% NP-40. Aliquots were stored at −70° C. until needed.

$\alpha_{IIb}\beta_3$/Fibrinogen Binding Assay.

An ELISA to measure interactions between integrin $\alpha_{IIb}\beta_3$ and fibrinogen was established by coating 96-well, flat-bottom EIA/RIA plates from Costar™ (Corning, Inc., Corning, N.Y.) with 200 ng of purified $\alpha_{IIb}\beta_3$ in 100 µL of binding buffer, for 12 to 18 hours at 37° C. Coated plates were subsequently washed, blocked, aspirated and re-washed as described previously for the $\alpha_v\beta_3$ ELISA. Locations of control wells and compound addition steps were also the same as described previously for the $\alpha_v\beta_3$ ELISA. Human fibrinogen, depleted of plasminogen, was purchased from Calbiochem (San Diego, Calif.) and biotinylated using a commercial kit (EZ-Link™ Sulfo-NHS-LC) from Pierce (Rockford, Ill.). Biotin-fibrinogen was diluted to 100 ng/mL in binding buffer/Tween-20, and 50 µL/well was added to the compound plates coated with $\alpha_{IIb}\beta_3$ in the presence or absence of compounds. The subsequent incubation and wash steps were the same as described previously for the $\alpha_v\beta_3$ ELISA. Bound biotin-fibrinogen was detected by the addition of 100 µL/well of streptavidin that was conjugated to HRP (Jackson ImmunoResearch Laboratories, Inc., West Grove, Pa.). The streptavidin-HRP conjugate was used at 250 ng/mL in binding buffer/Tween-20 containing 2% BSA. The subsequent incubation, wash and development steps were the same as described previously for the $\alpha_v\beta_3$ ELISA.

Cell Adhesion Assays

Short-Term Assays.

Assays to measure cell adhesion to extracellular matrix proteins in the presence or absence of compounds were conducted using both immortalized and primary human cells. The melanoma lines G-361 and A2058 were obtained from the American Type Culture Collection (ATCC, Rockville, Md.). The G-361 line was maintained in McCoy's 5A Medium (16600-082, GibcoBRL) supplemented with 10% fetal calf serum (FCS), and L-glutamine; the A2058 line was maintained in DMEM Medium (11960-044, Gibco BRL) supplemented with 10% fetal calf serum (FCS), and L-glutamine. Primary human umbilical vein endothelial cells (HUVEC) from pooled donors were obtained from Clonetics (San Diego, Calif.). HUVEC cultures were maintained and passaged on schedules recommended by Clonetics.

Cell adhesion assays were performed using 96-well, flat-bottom, non-tissue culture-treated plates (9050, Costar™, Corning, Inc., Corning, N.Y.). The wells received 100 µL of PBS containing vitronectin (Collaborative Biomedical Products) at 1 µg/mL or fibronectin (GibcoBRL, Rockville, Md.) at 2 µg/mL, for 12 to 18 hours at 4° C. Wells D1 to D6 received PBS alone, and served as control wells to measure nonspecific attachment of cells to untreated plastic. Wells were aspirated, washed once with 250 µL PBS, and blocked with 250 µL of PBS containing 2% BSA, for 2 hours at room temperature. The wells were aspirated, and received 250 µL of adhesion buffer, composed of Hepes-Buffered Saline Solution (HBSS, Clonetics) containing 1% BSA, 1 mM $CaCl_2$, 1 mM $MgCl_2$ and 2 mM $MnCl_2$. The wells were aspirated completely and 40 µL of adhesion buffer was added, followed by the addition of various dilutions of compounds in 5% DMSO/95% water. During the plate-blocking step, human cells were washed once with PBS, followed by gentle detachment with sterile PBS containing 10 mM EDTA. Detached cells were counted, pelleted, and gently resuspended at one million cells per mL in warm adhesion buffer. 50 µL Of the cell suspension (fifty thousand cells) was added to the plates containing compounds, and plates were transferred to a 37° C. incubator for 1 hour. Subsequently, the unattached cells were removed by one gentle wash of 300 µL/well warm cell media lacking fetal calf serum, followed by the addition of 100 µL/well warm cell media lacking fetal calf serum. 25 µL Of PBS containing 2 mg/mL MTT (3-[4,5-dimethylthiazole-2-yl]-2,5-diphenyltetrazolium bromide; Sigma) was added, and plates were returned to the 37° C. incubator for 1 to 1½ hours. Wells were aspirated, and the metabolized MTT formazan product was solubilized with 100 µL of ethanol/acetone (50%/50%). Plates were read at 540 nM in an EL340 Bio Kinetics Reader (Bio-Tek Instruments, Inc); the mean absorbance from control wells (D1-D6) was subtracted, and cell adhesion relative to the control wells lacking compounds (D7-D12) was plotted.

Long-Term Adhesion, Growth and Survival Assays.

The short-term adhesion assay (one-hour co-incubation of cells with compounds) could be adapted to assays that measure longer-term (5 to 48 hours) effects of compounds on the adhesion, growth and/or survival of cells seeded onto various ECM proteins. For assays using MTT as the readout, compound evaluations were conducted similarly to the one-hour assays with several modifications. First, only HUVEC cells were utilized, and each well was seeded with 17,000 cells instead of 50,000. Second, the adhesion buffer was substituted with regular growth medium to support the growth and survival of adhering HUVEC over extended time periods.

Administration of the compounds of the present invention (hereinafter the "active compound(s)") can be affected by any method that enables delivery of the compounds to the site of action. These methods include oral routes, intraduodenal routes, parenteral injection (including intravenous, subcutaneous, intramuscular, intravascular or infusion), topical, and rectal administration. The compound represented by Formula I, or a pharmaceutically acceptable salt thereof, may also be administered by controlled release means and/or delivery devices.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for example vinblastine; alkylating agents, for example cisplatin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N̄-(3,4-dihydro-2-methyl-4-oxoquinazolin-6-ylmethyl)-N̄-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration such as a tablet, capsule, cachets, pill, powder, granules, sustained release formulations, solution, as a suspension in an aqueous liquid, as a non-aqueous liquid, as an oil-in-water emulsion, as a water-in-oil liquid emulsion, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and one or more of the compound according to the invention as an active ingredient. In addition, it may include other medicinal or pharmaceutical agents, carriers, adjuvants, etc. Optionally, tablets, capsules, or pills may be coated by standard aqueous or nonaqueous techniques.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include, for example, a solid, liquid, or gas, such as inert diluents or fillers, water and various organic solvents. The pharmaceutical compositions may, if desired, contain additional ingredients such as flavorings, binders, excipients and the like. Thus for oral administration, tablets containing various excipients, such as citric acid, may be employed together with various disintegrants such as starch, alginic acid and certain complex silicates and with binding agents such as sucrose, gelatin and acacia. Additionally, lubricating agents such as magnesium stearate, sodium lauryl sulfate, hydroxypropylcellulose, and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring or dyes and emulsifying agents or suspending agents, together with diluents such as water, ethanol, propylene glycol, glycerin, or combinations thereof Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula 1 of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula 1, or pharmaceutically acceptable salts or solvates thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, abnormal cell growth may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

The present invention is further illustrated by, but not limited in scope to, the following examples and preparations.

ABBREVIATIONS

DMAP N,N-dimethylaminopyridine
DMF N,N-Dimethylformamide
DMSO Dimethylsulfoxide
HATU O-(7-Azabenzotriazol-1-yl)-N,N,N',N'-tetramethyluronium hexafluorophosphate
LCMS Liquid Chromatography/Mass Spectometry
NMP N-Methylpyrrolidinone
NMR Nuclear magnetic resonance
RP-HPLC Reverse Phase High Pressure Liquid Chromatography
TBTU O-(1H-Benzotriazol-1-yl)-N,N,N',N'-tetramethyluronium tetrafluoroborate Compound Numbering Compounds are numbered according to the relevant procedure [i.e. Compound 25b corresponds to the compound prepared in Procedure 25, Part (b)]. Compounds synthesised as part of combinatorial libraries are assigned a code of type Lx, where L denotes "Library" and x is the compound number.

Details for Experimental Procedures of Discrete Examples

Reverse phase, high pressure liquid chromatography used in the following preparations was effected according to the following general method. A HiChrom column (C18 silica packing, 5 micron particle size, 20×100 mm; AnaChem), was previously equilibrated in a mixture of water, acetonitrile, and trifluoroacetic acid (100:100:0.1) at pH 3.0. Samples were eluted using a linear gradient of 20 to 80% acetonitrile in water, containing 0.1% trifluoroacetic acid, at pH 3.0, over 20 minutes, with a flow rate of 10 mLmin$^{-1}$. Analysis was undertaken at 220 nm using a diode array detector.

Where a compound was isolated in the final instance by evaporation from aqueous hydrochloric acid, this was assumed to afford the compound as its corresponding hydrochloride salt. Likewise, where a compound was purified by RP-HPLC using a trifluoroacetic acid buffered mobile phase, it was assumed to be isolated as its trifluoroacetate salt. Salt equivalence was not determined for compounds.

Analytical Procedures $^1$H NMR analysis was conducted on a Varian Gemini instrument at 400 MHz, using standard-procedures.

LCMS analysis was performed using a Gilson 215 autosampler and Gilson 819 autoinjector, attached to a Hewlett Packard HP110. Mass spectra were obtained on a Micromass Platform LC mass spectrometer, using positive and negative electrospray ionisation. Masses found refer to the most abundant MH$^+$ positive ion found corresponding to title compound, unless otherwise stated.

The following general methods were used:

Method A: HiChrom RP3 column (5 micron, 3.2×100 mm), 7.5 minute gradient or

Method B: Supelco Discovery C18 (5 micron, 4.6×50 mm), 4.8 minute gradient or

Method C: Waters Symmetry C18 (5 micron, 2.1×30 mm), 3.5 minute gradient

Samples were eluted using a linear gradient of 0-100% Solvent B in Solvent A over either 4.8 or 7.5 minutes (see above). The buffer used was either formic acid (0.1%) or ammonium acetate (10 mM). The buffer used was observed to have no noticeable effect on sample retention time.

Mobile Phase I: (plus buffer)

Solvent A: Water (95%), acetonitrile (5%).

Solvent B: Acetonitrile (100%).

Mobile Phase II: (plus buffer)

Solvent A: Water (95%), methanol (5%).

Solvent B: Methanol (100%).

Preparation 1

(a) Methyl 3-(5-nitro-1H-benzimidazol-1-yl)butanoate and methyl 3-(6-nitro-1H-benzimidazol-1-yl)butanoate

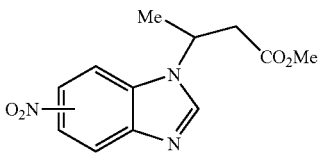

To a solution of 5-nitrobenzimidazole (250 mg, 1.53 mmol) in dry methanol (10 mL) was added methyl crotonate (325 μL, 3.06 mmol) and sodium methoxide (35 μL of a 25 wt % solution in methanol, 153 μmol), and the resulting solution heated to reflux for 48 hours. The solution was then evaporated in vacuo to afford the title compound as a ca. 1:1 mixture of regioisomers (as determined by $^1$H NMR), $^1$H NMR: (CDCl$_3$) of the mixture, 8.65 (d, J=2.20), 8.43 (d, J=2.20), 8.25-8.14 (m), 7.81 (d, J=8.79), 7.55 (d, J=9.16), 5.09-5.01 (m), 3.59 (s), 3.58 (s), 3.06-2.87 (m), 1.73 (d, J=6.96), 1.71 (d, J=6.96).

(b) Methyl 3-(5-amino-1H-benzimidazol-1-yl)butanoate & methyl 3-(6-amino-1H-benzimidazol-1-yl)butanoate

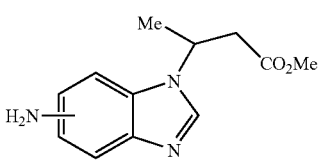

To a solution of the mixture of methyl 3-(5-nitro-1H-benzimidazol-1-yl)butanoate & methyl 3-(6-nitro-1H-benzimidazol-1-yl)butanoate (400 mg, 1.52 mmol, ca. 1:1 mixture) in methanol (10 mL) was added palladium on carbon (100 mg, 10% w/w Pd). The suspension was then stirred under an atmosphere of hydrogen for 110 hours. The suspension was filtered, evaporated in vacuo, and the residue purified by flash column chromatography on silica gel, eluting with a mixture of dichloromethane and methanol (97:3 to 9:1). This gave, in order of elution, methyl 3-(5-amino-1H-benzimidazol-1-yl)butanoate (91 mg), [LCMS (Method A, Mobile Phase II) RT=3.24 min, MH$^+$ 234]; methyl 3-(6-amino-1H-benzimidazol-1-yl)butanoate (78 mg), [LCMS (Method A, Mobile Phase II) RT=3.38 min, MH$^+$ 234].

Example 1c 3-(5-Amino-1H-benzimidazol-1-yl)butanoic acid

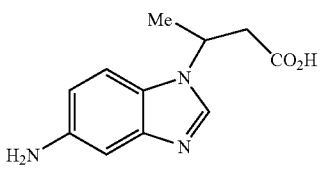

A solution of methyl 3-(5-amino-1H-benzimidazol-1-yl)butanoate (91 mg, 390 μmol) in hydrochloric acid (5 mL of a 5N solution) was stirred at room temperature for 163 hours. The solution was then evaporated in vacuo to afford the title compound, [LCMS (Method A, Mobile Phase II) RT=1.54 min, MH$^+$ 220].

(d) Example 1d 3-(6-Amino-1H-benzimidazol-1-yl)butanoic acid

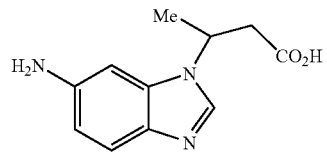

A solution of methyl 3-(6-amino-1H-benzimidazol-1-yl)butanoate (78 mg, 334 μmol) in hydrochloric acid (5 mL of a 5N solution) was stirred at room temperature for 163 hours. The solution was then evaporated in vacuo to afford the title compound, [LCMS (Method A, Mobile Phase II) RT=1.53 min, MH$^+$ 220].

Example 2

(a) Ethyl-3-(5-nitro-1H-benzimidazol-1-yl)-3-phenyl-2-propenoate & ethyl-3-(6-nitro-1H-benzimidazol-1-yl)-3-phenyl-2-propenoate

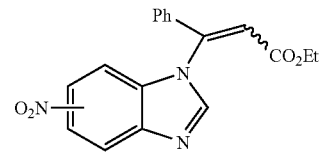

To a solution of 5-nitrobenzimidazole (3.00 g, 18.4 mmol) in DMF (60 mL) was added ethyl phenylpropiolate (3.34 mL, 20.2 mmol) and potassium carbonate (2.80 g, 20.3 mmol). The suspension was then heated to 110° C., and stirred for 20 hours. The suspension was evaporated to dryness in vacuo, and the residue was purified by flash column chromatography on silica gel, eluting with a mixture of dichloromethane and methanol (95:5), to give a mixture of the title compounds. [LCMS (Method A, II) RT=5.70 and 5.80 min respectively, MH$^+$ 338].

(b) Ethyl 3-(5-amino-1H-benzimidazol-1-yl)-3-phenylpropanoate & ethyl 3-(6-amino-1H-benzimidazol-1-yl)-3-phenylpropanoate

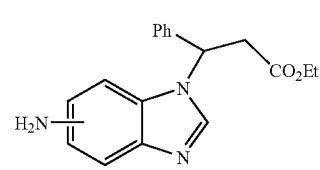

To a mixture of ethyl-3-(5-nitro-1H-benzimidazol-1-yl)-3-phenyl-2-propenoate and ethyl-3-(6-nitro-1H-benzimidazol-1-yl)-3-phenyl-2-propenoate (5.34 g, 15.8 mmol) in a mixture of ethanol and water (10:1, 66 mL) was added palladium on carbon (801 mg, 10% w/w Pd) and ammonium formate (6.0 g, 95 mmol). The suspension was heated to reflux, and was stirred at this temperature for 1.5 hours. The reaction mixture was allowed to cool to room temperature, then filtered through Celite®, and the filter pad washed several times with ethanol. The combined filtrates were evaporated in vacuo, and the residue was purified by flash column chromatography on silica gel, eluting with a mixture of dichloromethane and methanol (99:1) to give, in order of elution, ethyl 3-(6-amino-1H-benzimidazol-1-yl)-3-phenylpropanoate, [LCMS (Method A, Mobile Phase I) RT=3.33 min, MH+ 310] and ethyl 3-(5-amino-1H-benzimidazol-1-yl)-3-phenylpropanoate (1.96 g), [LCMS (Method A, Mobile Phase I) RT=3.35 min, MH+ 310].

(c) Example 2c 3-(5-Amino-1H-benzimidazol-1-yl)-3-phenylpropanoic acid

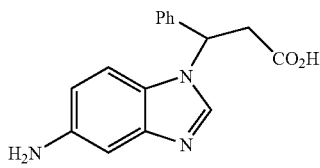

A solution of ethyl 3-(5-amino-1H-benzimidazol-1-yl)-3-phenylpropanoate (40 mg, 129 µmol) in hydrochloric acid (20 mL of a 5N solution) was stirred at room temperature for 72 hours. The solution was evaporated in vacuo and purified by RP-HPLC to afford the title compound, [LCMS (Method A, Mobile Phase II) RT=2.61 min, MH+ 282].

(d) 3-(6-Amino-1H-benzimidazol-1-yl)-3-phenylpropanoic acid

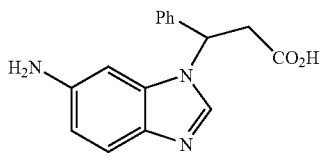

A solution of ethyl 3-(6-amino-1H-benzimidazol-1-yl)-3-phenylpropanoate, (25 mg, 81 µmol) in hydrochloric acid (20 mL of a 5N solution) was stirred at room temperature for 96 hours. The solution was evaporated in vacuo and purified by RP-HPLC to afford the title compound, [LCMS (Method A, Mobile Phase II) RT=2.59 min, MH+ 282].

Preparation 3

(a) Ethyl 3-(1H-benzimidazol-1-yl)-3-(4-ethylphenyl)-2-propenoate

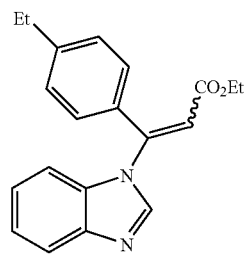

To a solution of benzimidazole (118 mg, 1.00 mmol) in DMF (3 mL) was added ethyl 3-(4-ethylphenyl)-2-propynoate (202 mg, 1.00 mmol) and potassium carbonate (152 mg, 1.10 mmol). This suspension was heated to 100° C. for 48 hours, then cooled to room temperature, and evaporated in vacuo. The residue was partitioned between water and dichloromethane, and the separated aqueous layer extracted with dichloromethane. The combined organic layers were dried over anhydrous magnesium sulfate, filtered, and evaporated in vacuo. The residue was purified by flash column chromatography on silica gel, eluting with a mixture of dichloromethane and methanol (96:4) to afford (in order of elution), ethyl (2Z)-3-(1H-benzimidazol-1-yl)-3-(4-ethylphenyl)-2-propenoate, mixed fractions, and ethyl (2E)-3-(1H-benzimidazol-1-yl)-3-(4-ethylphenyl)-2-propenoate.

E isomer; $^1$H NMR: (CDCl$_3$), 8.02 (s, 1H), 7.90 (dd, J=8.06, 0.73, 1H), 7.34-7.20 (m, 6H), 6.97 (d, J=8.06, 1H), 6.48 (s, 1H), 4.05 (q, J=6.96, 2H), 2.73 (q, J=7.69, 2H), 1.30 (t, J=7.69, 3H), 1.05 (t, J=6.96, 3H)

Z isomer; $^1$H NMR: (CDCl$_3$), 7.87 (s, 1H), 7.83 (d, J=8.06, 1H), 7.34-7.22 (m, 6H), 7.15 (d, J=8.06, 1H), 6.27 (s, 1H), 4.16 (q, J=6.96, 2H), 2.74 (q, J=7.69, 2H), 1.30 (t, J=7.69, 3H), 1.21 (t, J=6.96, 3H).

(b) Example 3b (2E)-3-(1H-Benzimidazol-1-yl)-3-(4-ethylphenyl)-2-propenoic acid

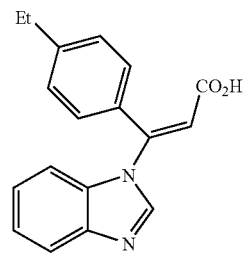

A solution of ethyl (2E)-3-(1H-benzimidazol-1-yl)-3-(4-ethylphenyl)-2-propenoate (46 mg, 143 µmol) in hydrochloric acid (10 mL of a 5N solution) was stirred at room temperature for 72 hours, and then heated at reflux for 6 hours.

(c) Example 3c

(2Z)-3-(1H-Benzimidazol-1-yl)-3-(4-ethylphenyl)-2-propenoic acid

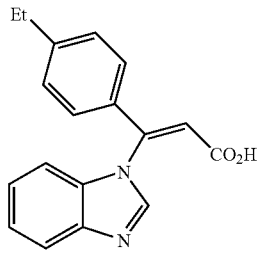

A solution of ethyl (2Z)-3-(1H-benzimidazol-1-yl)-3-(4-ethylphenyl)-2-propenoate (60 mg, 187 μmol) in hydrochloric acid (10 mL of a 5N solution) was stirred at room temperature for 72 hours, and then heated at reflux for 6 hours. The solution was cooled to room temperature, and evaporated in vacuo to afford the title compound, [LCMS (Method A, Mobile Phase I) RT=6.63 min, MH$^+$ 294].

Preparation 4

(a) Ethyl 3-(1H-benzimidazol-1-yl)-3-(4-ethylphenyl)propanoate

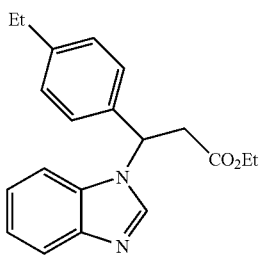

To a solution of ethyl 3-(1H-benzimidazol-1-yl)-3-(4-ethylphenyl)-2-propenoate (E/Z mixture, 181 mg, 566 μmol) in a mixture of ethanol and water (10:1, 2.75 mL) was added palladium on carbon (27 mg, 10% w/w Pd) and ammonium formate (143 mg, 2.26 mmol). The suspension was brought to reflux for 3 hours, cooled to room temperature, and was filtered through a pad of Celite® and evaporated in vacuo. The residue was purified by flash column chromatography on silica gel, eluting with a mixture of dichloromethane and methanol (96:4) to afford the title compound, $^1$H NMR: (CDCl$_3$), 8.03 (s, 1H), (d, J=6.96, 1H), 7.31-7.06 (m, 7H), 6.01 (dd, J=8.79, 6.59, 1H), 4.04 (t, J=6.96, 2H), 3.38 (dd, J=15.75, 8.79, 1H), 3.31 (dd, J=15.75, 6.59, 1H), 2.62 (q, J=7.69, 2H), 1.18 (t, J=7.69, 3H), 1.09 (t, J=6.96, 3H).

(b) Example 4b

3-(1H-Benzimidazol-1-yl)-3-(4-ethylphenyl)propanoic acid

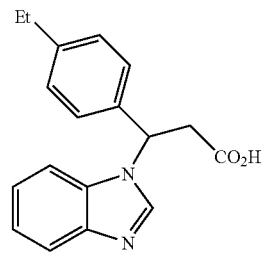

A suspension of ethyl 3-(1H-benzimidazol-1-yl)-3-(4-ethylphenyl)propanoate (180 mg, 559 μmol) in hydrochloric acid (10 mL of a 5N solution) was stirred at room temperature for 72 hours. A mixture of acetonitrile and methanol (10:1, 11 mL) was added, and the resulting solution stirred at room temperature for 110 hours. The solution was warmed to reflux for 24 hours, and evaporated in vacuo. The residue was taken up into aqueous sodium carbonate, and the resulting solution extracted with diethyl ether. The aqueous phase was acidified with dilute hydrochloric acid (pH<4), and extracted with dichloromethane. The combined dichloromethane extracts were evaporated in vacuo to afford the title compound, [LCMS (Method A, Mobile Phase I) RT=4.20 min, MH$^+$ 296].

Preparation 5

(a) Ethyl 3-(1H-benzimidazol-1-yl)-3-(1,1'-biphenyl)-4-yl-2-propenoate

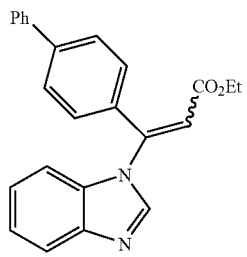

Using the process in Preparation 3, ethyl 3-(1,1'-biphenyl)-4-yl-2-propynoate gave the title compound (318 mg) as an approximate 3:1 mix of geometric isomers, as determined by $^1$H NMR. $^1$H NMR: (CDCl$_3$) of the mixture, 8.01 (s), 7.92-7.16 (m), 6.95 (d, J=8.06), 6.51 (s), 6.31 (s), 4.18 (q, J=7.32), 4.01 (q, J=7.32), 1.22 (t, J=7.32), 1.00 (t, J=7.32).

(b) Ethyl 3-(1H-benzimidazol-1-yl)-3-(1,1'-biphenyl)-4-ylpropanoate

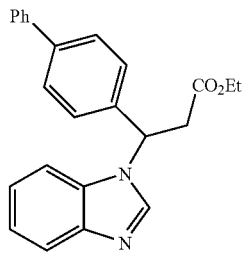

To a solution of ethyl 3-(1H-benzimidazol-1-yl)-3-(1,1'-biphenyl)-4-yl-2-propenoate (318 mg, 861 μmol) in a mixture of ethanol and water (17:2, 4.2 mL) was added palladium on carbon (47 mg, 10% w/w Pd) and ammonium formate (218 mg, 3.46 mmol). The suspension was brought to reflux for 3 hours, cooled to room temperature, and was filtered through a pad of Celite® and evaporated in vacuo. The residue was purified by flash column chromatography on silica gel, eluting with a mixture of dichloromethane and methanol (97:3) to afford the title compound, [LCMS (Method A, Mobile Phase I) RT=6.51 min, MH$^+$ 371.7].

(c) Example 5c 3-(1H-Benzimidazol-1-yl)-3-(1,1'-biphenyl)-4-ylpropanoic acid

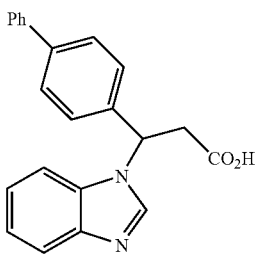

A solution of ethyl 3-(1H-benzimidazol-1-yl)-3-(1,1'-biphenyl)-4-ylpropanoate (276 mg, 746 μmol) in hydrochloric acid (50 mL of a 5N solution) was stirred at room temperature for 12 hours. Acetonitrile (I mL) was then added, and stirring continued for 110 hours. The solution was warmed to reflux for 24 hours and was then cooled to room temperature and evaporated in vacuo. The residue was taken up into aqueous sodium carbonate and the resulting solution extracted with diethyl ether. The aqueous phase was acidified with dilute hydrochloric acid (pH<4), and re-extracted with dichloromethane. The combined dichloromethane extracts were evaporated in vacuo, and the residue was recrystallized from methanol to afford the title compound, [LCMS (Method A, Mobile Phase I) RT=4.66 min, MH$^+$ 343].

Preparation 6

(a) Ethyl 3-[4-bromo-6-(trifluoromethyl)-1H-benzimidazol-1-yl]-3-phenyl-2-propenoate

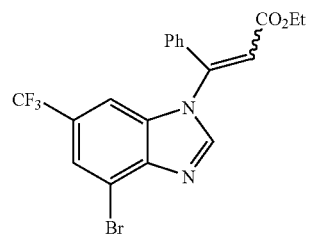

To a solution of 4-bromo-6-trifluoromethylbenzimidazole (1.00 g, 3.77 mmol) in DMF (10 mL) was added potassium carbonate (520 mg, 3.77 mmol) and ethyl phenylpropiolate (690 μL, 4.15 mmol). The suspension was then warmed to 100° C. for 4 hours, cooled to room temperature, and was evaporated in vacuo. The residue was purified by flash column chromatography on silica gel, eluting with a mixture of dichloromethane and methanol (99:1), to afford the title compound as a mixture of geometric isomers (ca. 6:1 as determined by $^1$H NMR). $^1$H NMR: (CDCl$_3$) of the mixture, 8.16 (s), 8.13 (s), 7.76 (br), 7.57-7.17 (m), 6.61 (s), 6.30 (s), 4.18 (q, J=7.32), 4.07 (q, J=7.32), 1.21 (t, J=7.32), 1.10 (t, J=7.32).

(b) Ethyl 3-phenyl-3-[6-(trifluoromethyl)-1H-benzimidazol-1-yl]propanoate

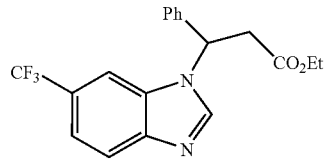

To a solution of ethyl 3-[4-bromo-6-(trifluoromethyl)-1H-benzimidazol-1-yl]-3-phenyl-2-propenoate (111 mg, 253 μmol) in ethanol (4 mL) was added palladium on carbon (23 mg, 10% w/w Pd) and ammonium formate (159 mg, 2.52 mmol). The suspension was heated to reflux for 3 hours, then cooled to room temperature, and filtered through a pad of Celite®. The filtrate was evaporated in vacuo to afford the title compound, $^1$H NMR: (CDCl$_3$), 8.10 (s, 1H), 7.79 (d, J=8.79, 1H), 7.49 (s, 1H), 7.42 (d, H=8.79, 1H), 7.31-7.23 (m, 3H), 7.18-7.14 (m, 2H), 6.00 (dd, J=6.96, 6.96, 1H), 3.98 (q, J=7.32, 2H), 3.36-3.25 (m, 2H), 1.03 (t, J=7.32, 3H).

(c) Example 6c

3-Phenyl-3-[6-(trifluoromethyl)-1H-benzimidazol-1-yl]propanoic acid

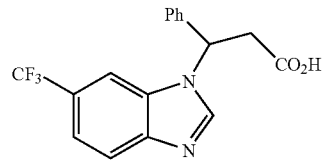

A solution of ethyl 3-phenyl-3-[6-(trifluoromethyl)-1H-benzimidazol-1-yl]propanoate (74 mg, 204 μmol) in hydrochloric acid (10 mL of a 5N solution) was stirred at room temperature for 96 hours. The solution was evaporated in vacuo to afford the title compound, [LCMS (Method A, Mobile Phase II) RT=4.07 min, MH+ 335].

Preparation 7

(a) tert-Butyl (3R)-3-(2-nitroanilino)-3-phenylpropanoate

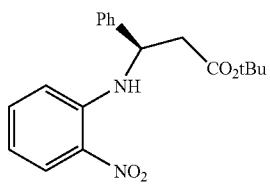

To a solution of 2-fluoronitrobenzene (150 mg, 1.06 mmol) in dichloromethane (4 mL) was added tert-butyl (3R)-3-amino-3-phenylpropanoate (235 mg, 1.06 mmol) and triethylamine (300 μL, 2.12 mmol). The solution was stirred at room temperature for 4 hours, and was then evaporated in vacuo. The residue was purified by flash column chromatography on silica gel, eluting with dichloromethane, to afford the title compound, $^1$H NMR: (CD$_3$OD), 8.76 (br m, 1H), 8.18 (d, J=7.69, 1H), 7.44 (d, J=7.69, 2H), 7.40-7.37 (m, 2H), 7.32-7.28 (m, 1H), 6.84 (d, J=8.79 1H), 6.73-6.69 (m, 1H), 5.12 (dd, J=13.18, 6.59 1H), 2.91 (d, J=6.59 2H), 1.41 (s, 9H).

(b) tert-Butyl (3R)-3-(2-aminoanilino)-3-phenylpropanoate

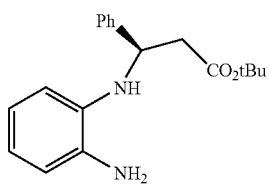

To a solution of tert-butyl (3R)-3-(2-nitroanilino)-3-phenylpropanoate (100 mg, 292 μmol) in a mixture of ethanol and water (4 mL, 3:1), was added palladium on carbon (20 mg, 10% w/w Pd) and ammonium formate (191 mg, 3.03 mmol). The suspension was heated to reflux for 10 minutes, and was then cooled to room temperature, filtered through a pad of Celite®, and evaporated in vacuo. The residue was purified by flash column chromatography on silica gel, eluting with a mixture of dichloromethane and methanol (98:2) to afford the title compound, $^1$H NMR: (CD$_3$OD) 7.41 (d, J=7.3, 1H), 7.33-7.31 (m, 2H), 7.25-7.21 (m, 1H), 6.75-6.73 (m, 1H), 6.72-6.52 (m, 2H), 6.47-6.45 (m, 1H), 4.82 (obs., 1H), 2.87 (dd, J=14.6, 7.7, 1H), 2.74 (dd, J=14.6, 6.2, 1H), 1.41 (s, 9H).

(c) tert-Butyl (3R)-3-(1H-benzimidazol-1-yl)-3-phenylpropanoate

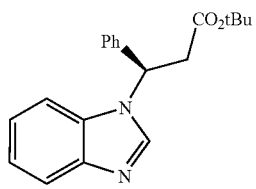

To a solution of tert-butyl (3R)-3-(2-aminoanilino)-3-phenylpropanoate (78 mg, 250 μmol) in 2-ethoxyethanol (2 mL), was added formamidine acetate (41 mg, 394 μmol). The solution was heated at 80° C. for 1.75 hours, and was then evaporated in vacuo. The residue was purified by flash column chromatography on silica gel, eluting with a mixture of dichloromethane and methanol (98:2) to afford the title compound, [LCMS (Method A, Mobile Phase I) RT=6.30 min, MH+ 323].

(d) Example 7d (3R)-3-(1H-Benzimidazol-1-yl)-3-phenylpropanoic acid

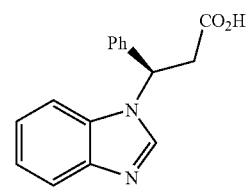

A solution of tert-butyl (3R)-3-(1H-benzimidazol-1-yl)-3-phenylpropanoate (92 mg, 285 μmol) in hydrochloric acid (20 mL of a 5N solution) was stirred at room temperature for 48 hours. The solution was then evaporated in vacuo to give a gum. Trituration of this residue with diethyl ether afforded the title compound, [LCMS (Method B, Mobile Phase I) RT=3.45 min, MH+ 267].

The corresponding S-enantiomer was prepared with a similar procedure, using tert-butyl (3S)-3-amino-3-phenylpropanoate, to give the title compound, [LCMS (Method A, Mobile Phase I) RT=3.43 min, MH+ 267].

A racemic mixture was prepared using the procedure as described in Preparation 2. Benzimidazole and ethyl phenylpropiolate gave the title compound, [LCMS (Method A, Mobile Phase II) RT=3.35 min, MH+ 267].

Example 8

3-(1H-Benzimidazol-1-yl)-3-(4-chlorophenyl)propanoic acid

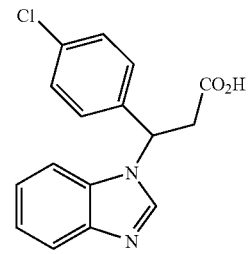

Using the procedure of Preparation 7, the title compound, (12.7 mg), was prepared using ethyl 3-amino-3-(4-chlorophenyl)propanoate as a starting material [prepared from commercially available (4-chlorophenyl)-β-alanine according to literature methods]. [LCMS (Method A, Mobile Phase I) RT=4.01 min, MH+ 301].

Example 9

(3R)-3-(1H-Benzimidazol-1-yl)-4-phenylbutanoic acid

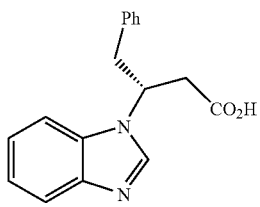

Using the procedure of Preparation 7, tert-butyl (3R)-3-amino-4-phenylbutanoate gave the title compound (91 mg), [LCMS (Method A, Mobile Phase I) RT=3.62 min, MH+ 282]. Starting from tert-butyl (3S)-3-amino-4-phenylbutanoate, the corresponding S-enantiomer, (204 mg), was prepared in a similar manner. [LCMS (Method A, Mobile Phase I) RT=3.54 min, MH=282].

Preparation 10

(a) 3-{3-[(4-Methoxybenzyl)amino]-2-nitroanilino}-3-phenylpropanoic acid

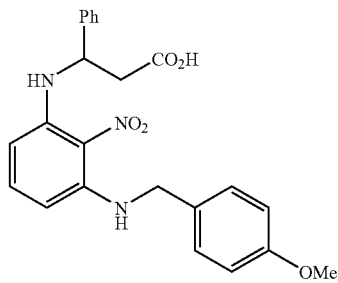

To a solution of 2,6-difluoronitrobenzene (200 mg, 1.26 mmol) in DMSO (2 mL) was added 3-amino-3-phenylpropionic acid (228 mg, 1.39 mmol) and potassium carbonate (347 mg, 2.52 mmol). The suspension was heated to 100° C. for 0.5 hour, and 4-methoxybenzylamine (180 μL, 1.39 mmol) was added, and heating continued for a further 3 hours. The suspension was cooled to room temperature, and partitioned between water and ethyl acetate. The aqueous layer was acidified with dilute hydrochloric acid (pH<4), and then extracted with ethyl acetate. The combined ethyl acetate extracts were dried over anhydrous magnesium sulfate, filtered, and evaporated in vacuo. The residue was purified by flash column chromatography on silica gel, eluting with a mixture of dichloromethane and methanol (19:1) to afford the title compound, [LCMS (Method A, Mobile Phase II) RT=4.75 min, MH+ 422].

(b) 3-{2-Amino-3-[(4-methoxybenzyl)amino]anilino}-3-phenylpropanoic acid

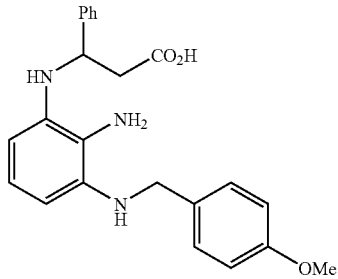

To a solution of 3-{3-[(4-methoxybenzyl)amino]-2-nitroanilino}-3-phenylpropanoic acid (176 mg, 418 μmol) in ethanol (6 mL) was added Raney-nickel (Aldrich22, 167-8, catalytic, ca. 5 mg) and hydrazine hydrate (200 μL, 4.12 mmol). The resulting suspension was stirred at room temperature for 0.6 hour. The suspension was filtered through Celite®, and the pad washed with ethanol. The combined filtrates were evaporated in vacuo, and the residue purified by flash column chromatography on silica gel, eluting with a mixture of dichloromethane and methanol (19:1) to afford the title compound, $^1$H NMR: (CD$_3$OD), 7.76-7.74 (m, 1H), 7.66-7.61 (m, 1H), 7.41-7.20 (m, 7H), 6.91-6.87 (m, 2H), 6.50-6.46 (m, 1H), 6.23-6.21 (m, 1H), 6.07-6.05 (m, 1H), 4.81 (br t, J=6.59, 1H), 4.27-4.24 (m, 3H), 3.80 (s, 3H), 2.90 (dd, J=15.38, 8.79, 1H), 2.76 (dd, J=15.38, 9.89, 1H).

(c) Example 10c

N-[1-(4-Methoxybenzyl)-1H-benzimidazol-4-yl]-3-phenylpropanoic acid

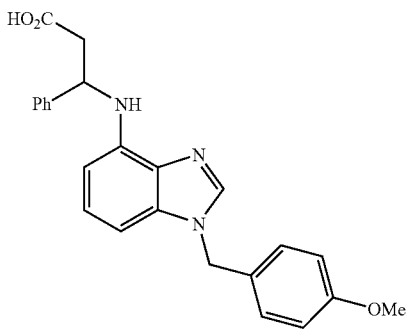

A solution of 3-{2-amino-3-[(4-methoxybenzyl)amino]anilino}-3-phenylpropanoic acid (18 mg, 46 μmol) in triethylorthoformate (2 mL) was heated at 100° C. for 2 hours. The solution was then cooled to room temperature, evaporated in vacuo, and the residue purified by RP-HPLC to afford the title compound, [LCMS (Method A, Mobile Phase II) RT=4.36 min, MH+ 402].

Preparation 11

(a) 3-[3-(Benzylamine)-2-nitroanilino]-3-phenylpropanoic acid

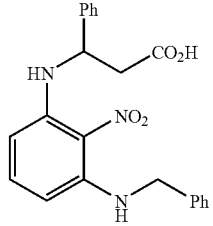

To a solution of 2,6-difluoronitrobenzene (500 mg, 3.14 mmol) in DMSO (3 mL) was added 3-amino-3-phenylpropionic acid (623 mg, 3.77 mmol) and potassium carbonate (529 mg, 3.83 mmol). The suspension was heated to 100° C. for 0.5 hour, then benzylamine (410 µL, 3.75 mmol) was added, and heating continued for a further 3 hours. The suspension was cooled to room temperature, and partitioned between water and ethyl acetate. The aqueous layer was separated and acidified with dilute hydrochloric acid (pH<4), and extracted with ethyl acetate. The combined ethyl acetate extracts were dried over anhydrous magnesium sulfate, filtered, and evaporated in vacuo. The residue was purified by flash column chromatography on silica gel, eluting with a mixture of dichloromethane and methanol (97:3) to afford the title compound, $^{1}$H NMR: (CD$_3$OD) 7.45-7.21 (m, 10H), 6.98 (dd, J=8.42, 8.42, 1H), 5.97 (d, J=8.42, 1H), 5.87 (d, J=8.79, 1H), 5.07-5.01 (m, 1H), 4.40-4.43 (m, 2H), 2.95-2.81 (m, 2H).

(b) 3-[2-Amino-3-(benzylamine)anilino]-3-phenylpropanoic acid

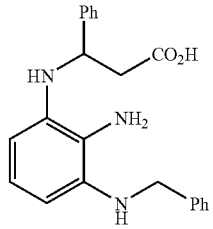

To a solution of 3-[3-(benzylamine)-2-nitroanilino]-3-phenylpropanoic acid (75 mg, 192 µmol) in a mixture of 1,4-dioxane, water and 0.88 ammonia solution (3:3:0.1, 6.1 mL) was added sodium dithionite (267 mg, 1.53 mmol). The solution was stirred at room temperature for 0.1 hour, and then extracted with ethyl acetate. The combined ethyl acetate extracts were dried over anhydrous magnesium sulfate, filtered, and evaporated in vacuo to afford the title compound, [LCMS (Method A, Mobile Phase II) RT=4.35 min, MH$^+$ 362].

(c) Example 11c

N-(1-Benzyl-1H-benzimidazol-4-yl)-3-phenylpropanoic acid

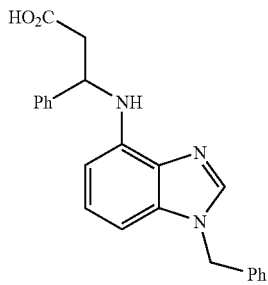

A solution of 3-[2-amino-3-(benzylamine)anilino]-3-phenylpropanoic acid (35 mg, 97 µmol) in triethylorthoformate (2 mL) was heated to 100° C. for 0.6 hour. The solution was evaporated in vacuo, and the residue dissolved in a mixture of hydrochloric acid (10 mL of a 5N solution) and acetonitrile (5 mL). This solution was stirred at room temperature for 48 hours, and then evaporated in vacuo. The residue was purified by RP-HPLC to afford the title compound, [LCMS (Method A, Mobile Phase II) RT=4.31 min, MH$^+$ 372.5].

Preparation 12

(a) 1-{3-[(3-Methoxy-3-oxo-1-phenylpropyl)amino]-2-nitrophenyl}-4-piperidinecarboxylic acid

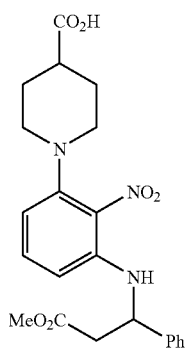

To a solution of 2,6-difluoronitrobenzene (272 mg, 1.71 mmol) in DMSO (2 mL) was added methyl-3-amino-3-phenylpropanoate (553 mg, 2.57 mmol) and potassium carbonate (709 mg, 5.13 mmol), and the suspension stirred at room temperature for 24 hours. 4-Piperidinecarboxylic acid (335 mg, 2.59 mmol) was added, and the resulting suspension stirred at room temperature for 24 hours, and then heated at 100° C. for 3 hours. The suspension was cooled to room temperature, and diluted with water. The aqueous solution was extracted with ethyl acetate, and the separated aqueous layer acidified with dilute hydrochloric acid (pH<4), and re-extracted with ethyl acetate. The second organic extracts were evaporated in vacuo, and the residue purified by flash column chromatography on silica gel, eluting with a mixture of dichloromethane and methanol (96:4) to afford the title compound, $^{1}$H NMR: (CDCl$_3$) 7.36-7.22 (m, 5H), 7.02 (t, J=8.06, 1H), 6.34 (dd, J=8.06, 1.10, 1H), 6.19 (d, J=8.06, 1H), 4.89-4.85 (m, 1H), 3.66 (s, 3H), 3.25-3.21 (m, 2H), 2.87-2.77 (m, 4H), 2.48-2.41 (m, 1H), 2.02-1.82 (m, 4H).

(b) 1-[1-(3-Methoxy-3-oxo-1-phenylpropyl)-1H-benzimidazol-4-yl]-4-piperidinecarboxylic acid

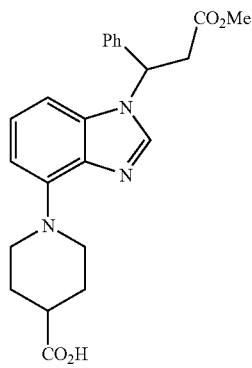

To a solution of 1-{3-[(3-methoxy-3-oxo-1-phenylpropyl)amino]-2-nitrophenyl}-4-piperidinecarboxylic acid (696 mg, 1.63 mmol) in ethanol (5 mL) was added Raney-Nickel (catalytic, ca. 5 mg) and hydrazine hydrate (316 μL, 6.52 mmol). The solution was stirred at room temperature for 3 hours, filtered, and evaporated in vacuo. The residue (560 mg) was dissolved in triethylorthoformate (5 mL), and heated at 60° C. for 0.5 hour. The resulting solution was cooled to room temperature, and evaporated in vacuo. The residue was purified by flash column chromatography on silica gel, eluting with a mixture of dichloromethane and methanol (92:8) to afford the title compound, $^1$H NMR: (CD$_3$OD) 8.27 (s, 1H), 7.34-7.28 (m, 5H), 7.10 (t, J=8.06, 1H), 6.99 (br d, J=8.06, 1H), 6.68 (d, J=8.06, 1H), 6.08 (dd, J=9.16, 6.22, 1H), 3.95-3.91 (m, 2H), 3.59 (obs dd, J=16.11, 9.16, 1H), 3.59 (s, 3H), 3.45 (dd, J=16.11, 6.22, 1H), 2.86-2.80 (m, 2H), 2.47-2.43 (m, 1H), 2.06-1.98 (m, 4H).

(c) Methyl 3-phenyl-3-(4-{4-[(1,4,5,6-tetrahydro-2-pyrimidinylamino)carbonyl]-1-piperidinyl}-1H-benzimidazol-1-yl)propanoate

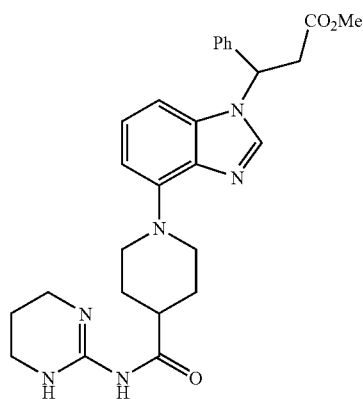

To a solution of 1-[1-(3-methoxy-3-oxo-1-phenylpropyl)-1H-benzimidazol-4-yl]-4-piperidinecarboxylic acid (70 mg, 172 μmol) in DMF was added N,N-diisopropylethylamine (60 μL, 344 μmol) and TBTU (66 mg, 206 μmol). The solution was stirred at room temperature for 0.5 hour, then 2-amino-1,4,5,6-tetrahydropyrimidine hydrobromide (34 mg, 189 μmol) was added. The mixture was heated to 80° C. for 8 hours, cooled to room temperature, and evaporated in vacuo. The residue was purified by RP-HPLC to afford the title compound, [LCMS (Method A, Mobile Phase II) RT=4.66 min, MH$^+$ 489].

(d) Example 12d

3-Phenyl-3-(4-{4-[(1,4,5,6-tetrahydro-2-pyrimidinylamino)carbonyl]-1-piperidinyl}-1H-benzimidazol-1-yl)propanoic acid

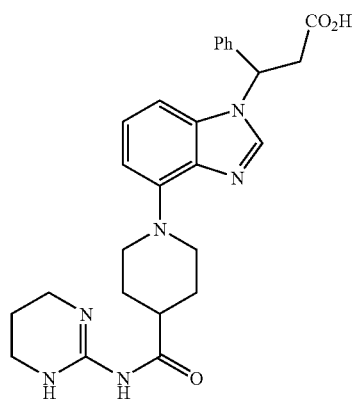

A solution of methyl 3-phenyl-3-(4-{4-[(1,4,5,6-tetrahydro-2-pyrimidinylamino)carbonyl]-1-piperidinyl}-1H-benzimidazol-1-yl)propanoate (17 mg, 24 μmol) in hydrochloric acid (10 mL of a 5N solution) was stirred at room temperature for 48 hours. The solution was evaporated in vacuo, and the residue purified by RP-HPLC to afford the title compound, [LCMS (Method A, Mobile Phase II) RT=3.5 min, MH$^+$ 475].

Preparation 13

(a) Ethyl 3-{5-[(4-nitrobenzoyl)amino]-1H-benzimidazol-1-yl}-3-phenylpropanoate

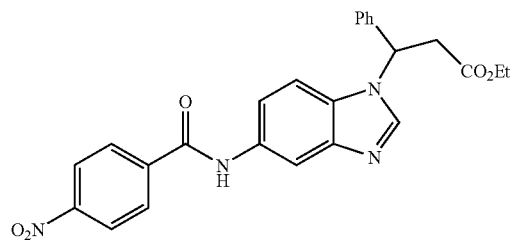

To a solution of ethyl 3-(5-amino-1H-benzimidazol-1-yl)-3-phenylpropanoate (100 mg, 324 μmol) in dichloromethane (6 mL) was added triethylamine (100 μL, 710 μmol) and 4-nitrobenzoyl chloride (132 mg, 712 μmol). The solution was stirred at room temperature for 96 hours, and was evaporated in vacuo. The residue was purified by flash column chromatography on silica gel, eluting with dichloromethane and methanol (97:3) to afford the title compound, [LCMS (Method A, Mobile Phase I) RT=4.92 min, MH$^+$ 459].

(b) Example 13b

3-{5-[(4-Nitrobenzoyl)amino]-1H-benzimidazol-1-yl}-3-phenylpropanoic acid

A solution of ethyl 3-{5-[(4-nitrobenzoyl)amino]-1H-benzimidazol-1-yl}-3-phenylpropanoate (60 mg, 131 μmol) in a mixture of acetonitrile (10 mL) and hydrochloric acid (20 mL of a 5N solution) was stirred at room temperature for 72 hours. The resulting precipitate was collected by filtration, and air-dried to afford the title compound, [LCMS (Method A, Mobile Phase II) RT=3.84 min, MH$^+$ 431].

Preparation 14

(a) Ethyl 3-{5-[(4-aminobenzoyl)amino]-1H-benzimidazol-1-yl}-3-phenylpropanoate

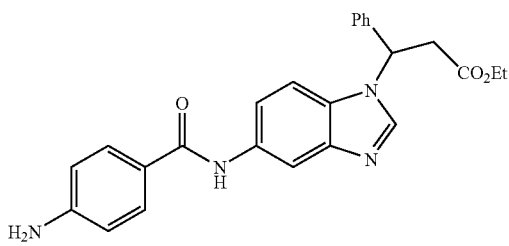

To a solution of ethyl 3-{5-[(4-nitrobenzoyl)amino]-1H-benzimidazol-1-yl}-3-phenylpropanoate (297 mg, 648 µmol) in a mixture of ethanol and water (4:1, 10 mL), was added palladium on carbon (60 mg, 10% w/w Pd) and ammonium formate (245 mg, 3.89 mmol). The resulting suspension was heated to reflux for 2 hours, and was then cooled to room temperature, and filtered through a pad of Celite®. The filtrate was evaporated to dryness, to afford the crude title compound, which was used directly without further purification, [LCMS (Method A, Mobile Phase I) RT=4.04 min, MH$^+$ 430].

(b) Example 14b

3-{5-[(4-Aminobenzoyl)amino]-1H-benzimidazol-1-yl}-3-phenylpropanoic acid

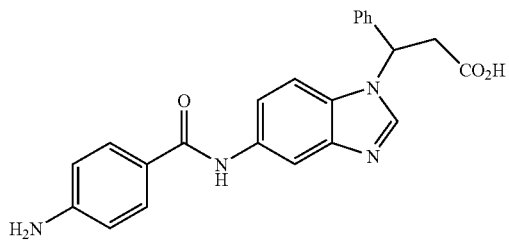

A solution of ethyl 3-{5-[(4-aminobenzoyl)amino]-1H-benzimidazol-1-yl}-3-phenylpropanoate (50 mg, 117 µmol) was dissolved in hydrochloric acid (25 mL of a 5N solution), and stirred at room temperature for 110 hours. The solution was evaporated in vacuo to afford the title compound, [LCMS (Method A, Mobile Phase II) RT=3.27 min, MH$^+$ 401].

Preparation 15

(a) Ethyl 3-{5-[(4-{[amino(imino)methyl]amino}benzoyl)amino]-1H-benzimidazol-1-yl}-3-phenylpropanoate

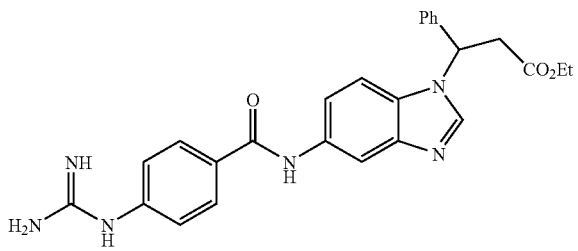

To a solution of ethyl 3-{5-[(4-aminobenzoyl)amino]-1H-benzimidazol-1-yl}-3-phenylpropanoate (60 mg, 140 µmol) in acetonitrile (1.2 mL) was added benzotriazolo-1-carboxamidine tosylate (55 mg, 157 µmol). The resulting suspension was heated to reflux for 16 h, then cooled to room temperature, evaporated in vacuo, and the residue purified by RP-HPLC to afford the title compound, [LCMS (Method A, Mobile Phase II) RT=4.25 min, MH$^+$ 471].

(b) Example 15b

3-{5-[(4-{[Amino(imino)methyl]amino}benzoyl)amino]-1H-benzimidazol-1-yl}-3-phenylpropanoic acid

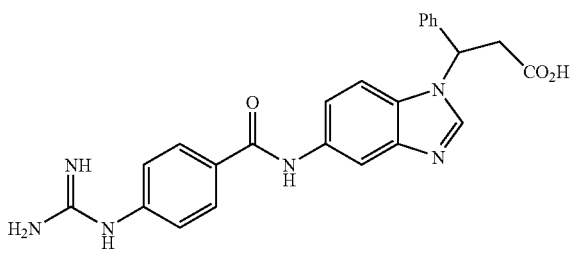

A solution of ethyl 3-{5-[(4-{[amino(imino)methyl]amino}benzoyl)amino]-1H-benzimidazol-1-yl}-3-phenylpropanoate (4.0 mg, 8.5 µmol) in hydrochloric acid (10 mL of a 5N solution) was stirred at room temperature for 72 hours. The solution was then evaporated in vacuo to afford the title compound, [LCMS (Method A, Mobile Phase II) RT=2.95 min, MH$^+$ 443].

Preparation 16

(a) Ethyl 3-{5-[(3-nitrobenzoyl)amino]-1H-benzimidazol-1-yl}-3-phenylpropanoate

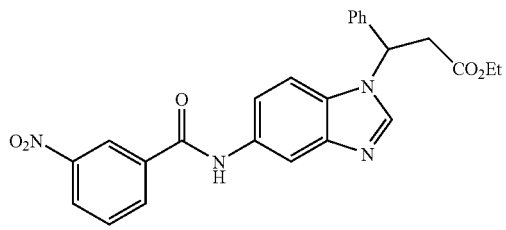

To a solution of ethyl 3-(5-amino-1H-benzimidazol-1-yl)-3-phenylpropanoate (250 mg, 809 µmol) in dichloromethane (15 mL) was added triethylamine (280 µL, 2.03 mmol), 3-nitrobenzoyl chloride (375 mg, 2.03 mmol) and DMAP (10 mg, 81 µmol). The solution was stirred at room temperature for 144 hours, and was then evaporated in vacuo. The residue was purified by flash column chromatography on silica gel, eluting with a mixture of dichloromethane and methanol (97:3) to afford the title compound, [LCMS (Method A, Mobile Phase II) RT=5.53 min, MH$^+$ 459].

(b) Example 16b

3-{5-[(3-Nitrobenzoyl)amino]-1H-benzimidazol-1-yl}-3-phenylpropanoic acid

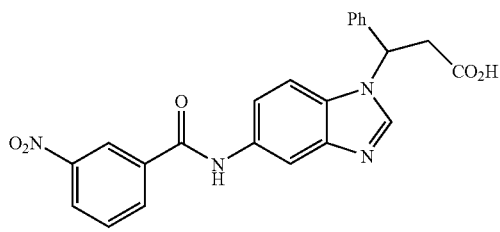

A solution of ethyl 3-{5-[(3-nitrobenzoyl)amino]-1H-benzimidazol-1-yl}-3-phenylpropanoate (40 mg, 87 μmol) in hydrochloric acid (20 mL of a 5N solution) was stirred at room temperature for 110 hours. The solution was then evaporated in vacuo, and purified by RP-HPLC to give the title compound, [LCMS (Method A, Mobile Phase II) RT=3.91 min, MH+ 431].

Preparation 17

(a) Ethyl 3-{5-[(3-aminobenzoyl)amino]-1H-benzimidazol-1-yl}-3-phenylpropanoate

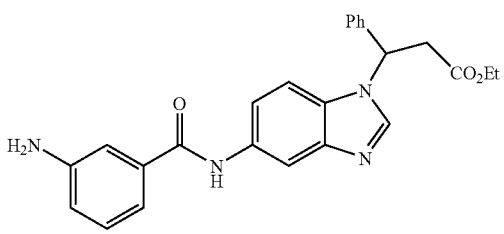

To a solution of ethyl 3-{5-[(3-nitrobenzoyl)amino]-1H-benzimidazol-1-yl}-3-phenylpropanoate (190 mg, 415 μmol) in a mixture of ethanol and water (4:1, 10 mL) was added palladium on carbon (38 mg, 10% w/w Pd) and ammonium formate (130 mg, 2.06 mmol). The suspension was heated to reflux for 2 hours, cooled to room temperature and filtered through a pad of Celite®. The filtrate was then evaporated in vacuo to afford the title compound, [LCMS (Method A, Mobile Phase I) RT=3.85 min, MH+ 429].

(b) Example 17b

3-{5-[(3-Aminobenzoyl)amino]-1H-benzimidazol-1-yl}-3-phenylpropanoic acid

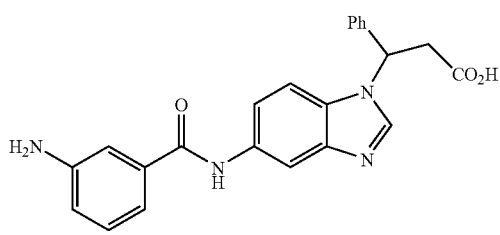

A solution of ethyl 3-{5-[(3-aminobenzoyl)amino]-1H-benzimidazol-1-yl}-3-phenylpropanoate (50 mg, 117 μmol) in hydrochloric acid (20 mL of a 5N solution) was stirred at room temperature for 110 hours. The solution was then evaporated in vacuo, and the residue was purified by RP-HPLC to afford the title compound, [LCMS (Method A, Mobile Phase II) RT=3.25 min, MH+ 401].

Preparation 18

(a) Ethyl 3-{5-[(3-{[amino(imino)methyl]amino}benzoyl)amino]-1H-benzimidazol-1-yl}-3-phenylpropanoate

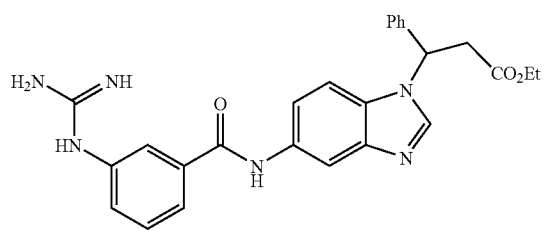

To a solution of ethyl 3-{5-[(3-aminobenzoyl)amino]-1H-benzimidazol-1-yl}-3-phenylpropanoate (60 mg, 140 μmol) in acetonitrile (1.2 mL) was added benzotriazolo-1-carboxamidine tosylate (50 mg, 142 μmol). The resulting suspension was heated to reflux for 16 hours, cooled to room temperature, and evaporated in vacuo. The residue was purified by RP-HPLC to afford the title compound, [LCMS (Method A, Mobile Phase II) RT=4.19 min, MH+ 471].

(b) Example 18b

3-{5-[(3-{[Amino(imino)methyl]amino}benzoyl)amino]-1H-benzimidazol-1-yl}-3-phenylpropanoic acid

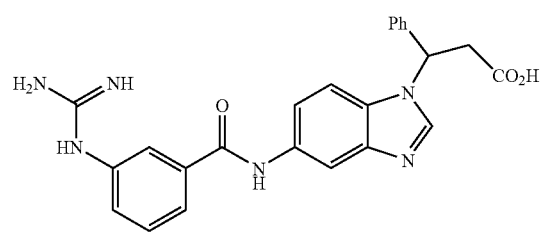

A solution of ethyl 3-{5-[(3-{[amino(imino)methyl]amino}benzoyl)amino]-1H-benzimidazol-1-yl}-3-phenylpropanoate (32 mg, 68 μmol) in hydrochloric acid (20 mL of a 5N solution) was stirred at room temperature for 96 hours. The solution was evaporated in vacuo and the residue was purified by RP-HPLC to afford the title compound, [LCMS (Method A, Mobile Phase II) RT=2.99 min, MH+ 443].

Preparation 19

(a) Ethyl 3-{5-[(2-nitrobenzoyl)amino]-1H-benzimidazol-1-yl}-3-phenylpropanoate

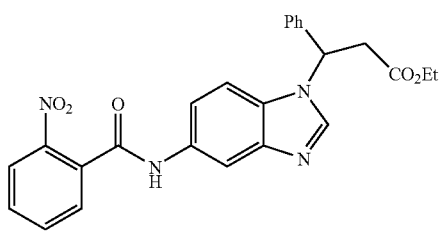

To a solution of ethyl 3-(5-amino-1H-benzimidazol-1-yl)-3-phenylpropanoate (250 mg, 809 μmol) in dichloromethane (15 mL) was added triethylamine (250 μL, 1.78 mmol) and 2-nitrobenzoyl chloride (240 μL, 1.78 mmol). The solution was stirred at room temperature for 110 hours, and was then evaporated in vacuo. The residue was purified by flash column chromatography on silica gel, eluting with a mixture of dichloromethane and methanol (97:3) to afford the title compound, [LCMS (Method A, Mobile Phase II) RT=5.23 min, MH$^+$ 459].

(b) Ethyl 3-{5-[(2-aminobenzoyl)amino]-1H-benzimidazol-1-yl}-3-phenylpropanoate

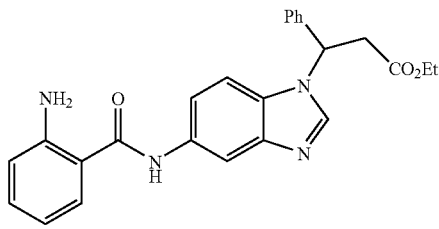

To a solution of ethyl 3-{5-[(2-nitrobenzoyl)amino]-1H-benzimidazol-1-yl}-3-phenylpropanoate (30 mg, 66 μmol) in a mixture of ethanol and water (4:1, 5 mL), was added palladium on carbon (6.0 mg, 10% w/w Pd) and ammonium formate (20 mg, 317 μmol). The suspension was heated to reflux for 3 hours, then cooled to room temperature, and filtered through a pad of Celite®. The filtrate was evaporated in vacuo to afford the title compound, $^1$H NMR: (CD$_3$OD), 8.48 (s, 1H), 8.06 (s, 1H), 7.64 (dd, J=7.69, 1.46, 1H), 7.50-7.35 (br, 7H), 7.28-7.24 (m, 1H), 6.82 (dd, J=8.42, 0.73 1H), 6.74-6.70 (m, 1H), 6.18 (dd, J=9.52, 5.86, 1H), 4.09 (1, J=7.32, 2H), 3.66 (dd, J=16.11, 9.52, 1H), 3.51 (dd, J=16.11, 5.86, 1H), 1.13 (t, J=7.32, 3H).

(c) Example 19c

3-{5-[(2-Aminobenzoyl)amino]-1H-benzimidazol-1-yl}-3-phenylpropanoic acid

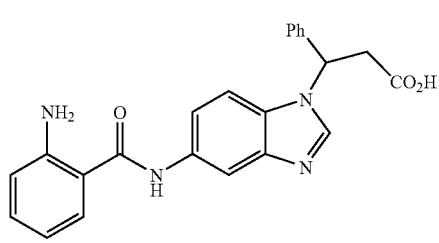

A solution of ethyl 3-{5-[(2-aminobenzoyl)amino]-1H-benzimidazol-1-yl}-3-phenylpropanoate (15 mg, 35 μmol) in hydrochloric acid (10 mL of a 5N solution) was stirred at room temperature for 72 hours. The solution was then evaporated in vacuo, and the residue was purified by RP-HPLC to afford the title compound, [LCMS (Method A, Mobile Phase II) RT=3.75 min, MH$^+$ 401].

Preparation 20

(a) Ethyl 3-{5-[(anilinocarbonyl)amino]-1H-benzimidazol-1-yl}-3-phenylpropanoate

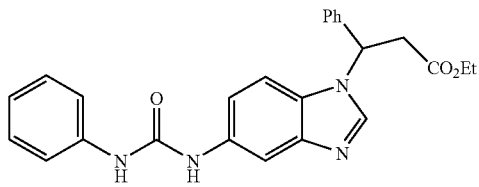

To a solution of ethyl 3-(5-amino-1H-benzimidazol-1-yl)-3-phenyl propanoate (0.400 g, 1.29 mmol) in methanol (15 mL) was added phenyl isocyanate (170 μL, 1.56 mmol) and N,N-diisopropylethylamine (270 μL, 1.55 mmol). The solution was stirred at room temperature for 72 hours, and then evaporated in vacuo. The residue was purified by flash column chromatography on silica gel, eluting with a mixture of dichloromethane and methanol (95:5) to afford the title compound, [LCMS (Method A, Mobile Phase I) RT=4.68 min, MH$^+$ 429], and the corresponding methyl ester [LCMS (Method A, Mobile Phase I) RT=4.48 min, MH$^+$ 415] in a 2:1 ratio.

(b) Example 20b

3-{5-[(Anilinocarbonyl)amino]-1H-benzimidazol-1-yl}-3-phenylpropanoic acid

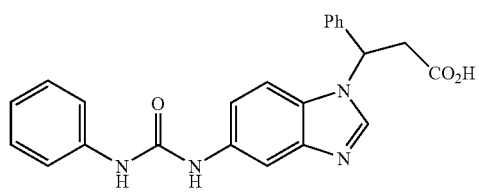

A solution of ethyl 3-{5-[(anilinocarbonyl)amino]-1H-benzimidazol-1-yl}-3-phenylpropanoate (491 mg, 1.14 mmol) in a mixture of hydrochloric acid (40 mL of a 5N solution) and acetonitrile (20 mL) was stirred at room temperature for 24 hours. Additional aliquotes of hydrochloric acid (20 mL of a 5N solution) and acetonitrile (10 mL) were then added, and stirring was continued for a further 72 hours. The solution was then evaporated in vacuo to afford the title compound, [LCMS (Method A, Mobile Phase I) RT=4.11 min, MH$^+$ 401].

Preparation 21

(a) Ethyl 3-{5-[(2-phenoxybenzoyl)amino]-1H-benzimidazol-1-yl}-3-phenylpropanoate

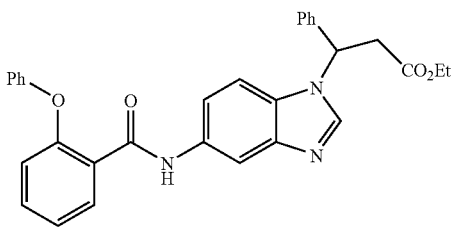

To a solution of 2-phenoxybenzoic acid (38 mg, 177 μmol) in acetonitrile (5 mL) was added N,N-diisopropylethylamine (40 μL, 229 μmol) and TBTU (62 mg, 193 μmol). The solution was stirred at room temperature for 0.5 hours, ethyl 3-(5-amino-1H-benzimidazol-1-yl)-3-phenyl propanoate (50 mg, 162 μmol) was added, and stirring continued at room temperature for 24 hours. The solution was evaporated in vacuo, and the residue was purified by flash column chromatography on silica gel, eluting with a mixture of dichloromethane and methanol (95:5) to afford the title compound. [LCMS (Method A, Mobile Phase I) RT=5.33 min, MH$^+$ 506].

(b) Example 21b

3-{5-[(2-Phenoxybenzoyl)amino]-1H-benzimidazol-1-yl}-3-phenylpropanoic acid

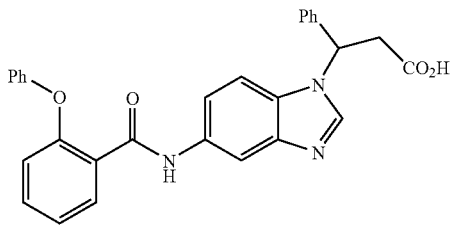

A solution of ethyl 3-{5-[(2-phenoxybenzoyl)amino]-1H-benzimidazol-1-yl}-3-phenylpropanoate (68 mg, 135 μmol) in a mixture of hydrochloric acid (20 mL of a 5N solution) and acetonitrile (20 mL) was stirred at room temperature for 48 hours. The solution was then concentrated in vacuo, and the resulting solid filtered off and vacuum-dried to afford the title compound, [LCMS (Method A, Mobile Phase I) RT=2.70 min, MH$^+$ 478].

Example 22

3-{5-[(2,6-Dimethoxybenzoyl)amino]-1H-benzimidazol-1-yl}-3-phenylpropanoic acid

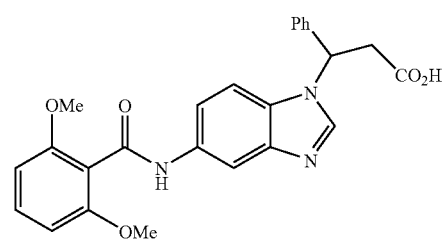

Using the procedure of Preparation 21, the title compound (31 mg) was prepared from ethyl 3-(5-amino-1H-benzimidazol-1-yl)-3-phenylpropanoate and 2,6-dimethoxybenzoic acid. [LCMS (Method C, Mobile Phase I) RT=2.25 min, MH$^+$ 446].

Example 23

3-Phenyl-3-[5-({[2-(phenylsulfanyl)-3-pyridinyl]carbonyl}amino)-1H-benzimidazol-1-yl]propanoic acid

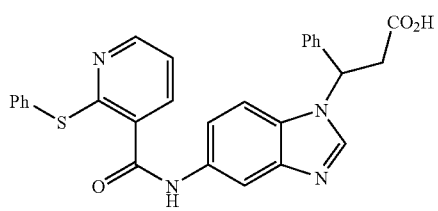

Using the procedure of Preparation 21, the title compound (48 mg) was prepared from ethyl 3-(5-amino-1H-benzimidazol-1-yl)-3-phenyl propanoate and 2-(phenylsulfanyl)nicotinic acid, and purified by RP-HPLC. [LCMS (Method A, Mobile Phase I) RT=4.35 min, MH$^+$ 495].

Example 24

3-(5-{[(2-Phenoxy-3-pyridinyl)carbonyl]amino}-1H-benzimidazol-1-yl)-3-phenylpropanoic acid

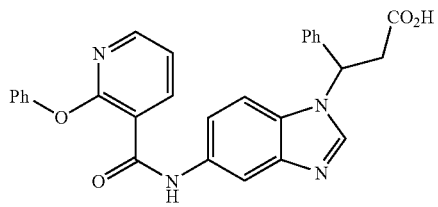

Using the procedure of Preparation 21, the title compound (52 mg) was prepared from ethyl 3-(5-amino-1H-benzimidazol-1-yl)-3-phenyl propanoate and 2-phenoxynicotinic acid, and purified by RP-HPLC. [LCMS (Method A, Mobile Phase I) RT=4.51 min, MH$^+$ 479].

Example 25

3-{5-[(2-Hydroxy-5-nitrobenzoyl)amino]-1H-benzimidazol-1-yl}-3-phenylpropanoic acid

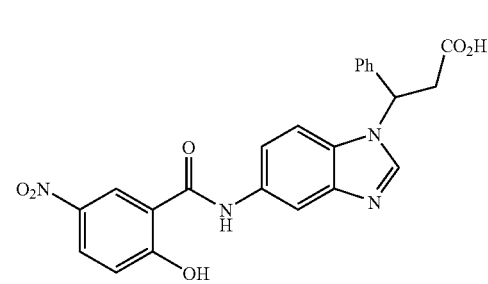

Using a similar procedure to that described in Preparation 21, the title compound (9 mg) was prepared from ethyl 3-(5-amino-1H-benzimidazol-1-yl)-3-phenyl propanoate and 2-hydroxy-5-nitrobenzoic acid (HATU was substituted for TBTU), and purified by RP-HPLC. [LCMS (Method A, Mobile Phase I) RT=4.46 min, MH$^+$ 447].

Preparation 26

(a) Ethyl 3-{6-[(4-nitrobenzoyl)amino]-1H-benzimidazol-1-yl}-3-phenylpropanoate

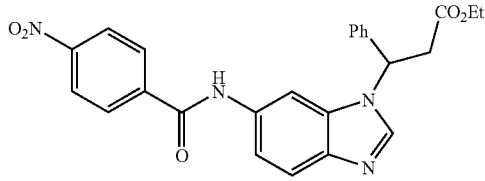

To a solution of ethyl 3-(6-amino-1H-benzimidazol-1-yl)-3-phenylpropanoate (200 mg, 647 μmol) in dichloromethane (15 mL) was added triethylamine (190 μL, 1.43 mmol) and 4-nitrobenzoyl chloride (264 mg, 1.43 mmol). The solution was stirred at room temperature for 72 hours, and was then evaporated in vacuo. The residue was purified by flash column chromatography on silica gel, eluting with a mixture of dichloromethane and methanol (97:3) to afford the title compound, [LCMS (Method A, Mobile Phase II) RT=5.42 min, MH$^+$ 459].

(b) Example 26b

3-{6-[(4-Nitrobenzoyl)amino]-1H-benzimidazol-1-yl}-3-phenylpropanoic acid

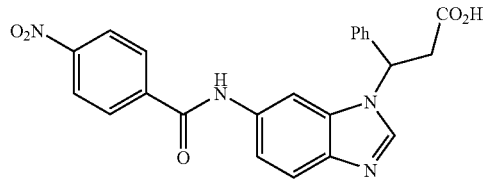

A solution of ethyl 3-{6-[(4-nitrobenzoyl)amino]-1H-benzimidazol-1-yl}-3-phenylpropanoate (40 mg, 87 μmol) in hydrochloric acid (20 mL of a 5N solution) was stirred at room temperature for 110 hours. The solution was then evaporated in vacuo, and the residue was purified by RP-HPLC to afford the title compound, [LCMS (Method A, Mobile Phase II) RT=3.89 min, MH$^+$ 431].

Preparation 27

(a) Ethyl 3-{6-[(4-aminobenzoyl)amino]-1H-benzimidazol-1-yl}-3-phenylpropanoate

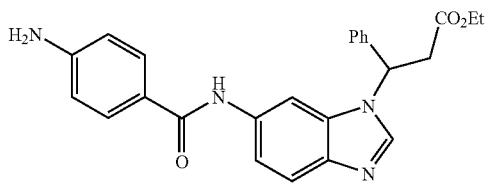

To a solution of ethyl 3-{6-[(4-nitrobenzoyl)amino]-1H-benzimidazol-1-yl}-3-phenylpropanoate (241 mg, 526 μmol) in a mixture of ethanol and water (6:1, 14 mL) was added palladium on carbon (48 mg, 10% w/w Pd) and ammonium formate (200 mg, 3.18 mmol). The suspension was heated to reflux for 2 hours, and was then cooled to room temperature, and filtered through a pad of Celite®. The filtrate was evaporated in vacuo to afford the title compound, [LCMS (Method A, Mobile Phase II) RT=4.61 min, MH$^+$ 429].

(b) Example 27b

3-{6-[(4-Amino benzoyl)amino]-1H-benzimidazol-1-yl}-3-phenylpropanoic acid

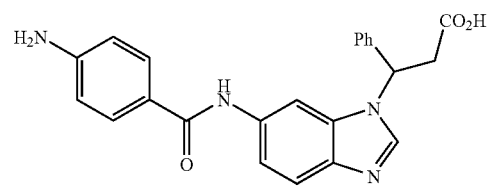

A solution of ethyl 3-{6-[(4-aminobenzoyl)amino]-1H-benzimidazol-1-yl}-3-phenylpropanoate (50 mg, 117 μmol) in hydrochloric acid (20 mL of a 5N solution) was stirred at room temperature for 72 hours. The solution was then evaporated in vacuo, and the residue was purified by RP-HPLC to afford the title compound, [LCMS (Method A, Mobile Phase II) RT=3.20 min, MH$^+$ 401].

Preparation 28

(a) Ethyl 3-{6-[(4-{[amino(imino)methyl]amino}benzoyl)amino]-1H-benzimidazol-1-yl}-3-phenylpropanoate

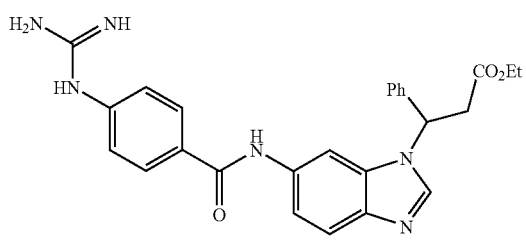

To a solution of ethyl 3-{6-[(4-aminobenzoyl)amino]-1H-benzimidazol-1-yl}-3-phenylpropanoate (60 mg, 140 μmol) in acetonitrile (1.2 mL) was added benzotriazolo-1-carboxamidine tosylate (50 mg, 142 μmol). The resulting suspension was then heated to reflux for 16 hours. Additional benzotriazolo-1-carboxamidine tosylate (50 mg, 142 μmol) was then added, and heating was continued for a further 16 hours. The suspension was cooled to room temperature, evaporated in vacuo, and the residue was purified by RP-HPLC to afford the title compound, [LCMS (Method A, Mobile Phase II) RT=3.86 min, MH$^+$ 471].

(b) Example 28b

3-{6-[(4-{[Amino(imino)methyl]amino}benzoyl)amino]-1H-benzimidazol-1-yl}-3-phenylpropanoic acid

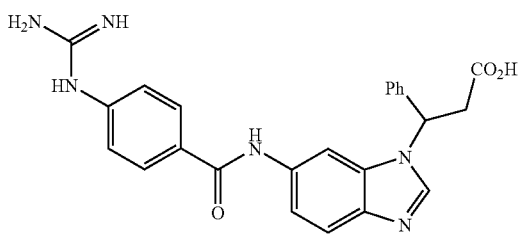

A solution of ethyl 3-{6-[(4-{[amino(imino)methyl]amino}benzoyl)amino]-1H-benzimidazol-1-yl}-3-phenylpropanoate (15 mg, 32 µmol) in hydrochloric acid (20 mL of a 5N solution) was stirred at room temperature for 96 hours. The solution was then evaporated in vacuo, and the residue was purified by RP-HPLC to afford the title compound, [LCMS (Method A, Mobile Phase II) RT=2.86 min, MH$^+$ 443].

Preparation 29

(a) Ethyl 3-{6-[(3-nitrobenzoyl)amino]-1H-benzimidazol-1-yl}-3-phenylpropanoate

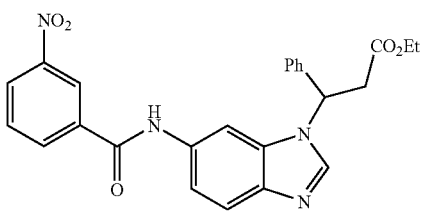

To a solution of ethyl 3-(6-amino-1H-benzimidazol-1-yl)-3-phenylpropanoate (200 mg, 647 µmol) in dichloromethane (15 mL) was added triethylamine (190 µL, 1.43 mmol) and 3-nitrobenzoyl chloride (264 mg, 1.43 mmol). The solution was stirred at room temperature for 96 hours, and DMAP (7.0 mg, 57 µmol) and 3-nitrobenzoyl chloride (120 mg, 647 µmol) was added, and the stirring continued at room temperature for 72 hours. Triethylamine (90 µL, 639 µmol), 3-nitrobenzoyl chloride (120 mg, 647 µmol) and DMAP (7.0 mg, 57 µmol) were then added. The solution was stirred at room temperature for 72 hours, evaporated in vacuo, and the residue purified by flash column chromatography on silica gel, eluting with a mixture of dichloromethane and methanol (97:3), to afford the title compound, [LCMS (Method A, Mobile Phase I) RT=5.52 min, MH$^+$ 459].

(b) Example 29b

3-{6-[(3-Nitrobenzoyl)amino]-1H-benzimidazol-1-yl}-3-phenylpropanoic acid

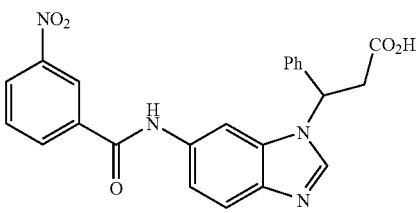

A solution of ethyl 3-{6-[(3-nitrobenzoyl)amino]-1H-benzimidazol-1-yl}-3-phenylpropanoate (40 mg, 87 µmol) in hydrochloric acid (20 mL of a 5N solution) was stirred at room temperature for 96 hours. The solution was then evaporated in vacuo, and the residue was purified by RP-HPLC to afford the title compound, [LCMS (Method A, Mobile Phase II) RT=3.92 min, MH$^+$ 431].

Preparation 30

(a) Ethyl 3-{6-[(3-aminobenzoyl)amino]-1H-benzimidazol-1-yl}-3-phenylpropanoate

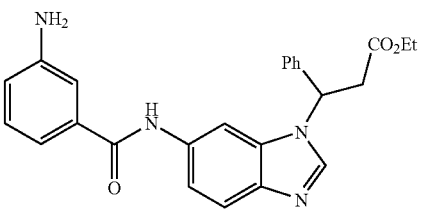

To a solution of ethyl 3-{6-[(3-nitrobenzoyl)amino]-1H-benzimidazol-1-yl}-3-phenylpropanoate (231 mg, 504 µmol) in a mixture of ethanol and water (4:1, 10 mL), was added palladium on carbon (46 mg, 10% w/w Pd) and ammonium formate (191 mg, 3.03 mmol). The suspension was heated to reflux for 3 hours, and was then cooled to room temperature, and filtered through a pad of Celite®. The filtrate was evaporated in vacuo to afford the title compound, $^1$H NMR: (CD$_3$OD), 8.43 (s, 1H), 8.14 (d, J=1.46, 1H), 7.65 (d, J=8.79, 1H), 7.47 (dd, J=8.79, 1.83, 1H), 7.30 (br, 8H), 6.92-6.90 (m, 1H), 6.11 (dd, J=9.52, 6.22, 1H), 4.04 (q, J=7.32, 2H), 3.62 (dd, J=16.11, 9.52, 1H), 3.46 (dd, J=16.11, 6.22, 1H), 1.08 (t, J=7.32, 3H).

(b) Example 30b

3-{6-[(3-Aminobenzoyl)amino]-1H-benzimidazol-1-yl}-3-phenylpropanoic acid

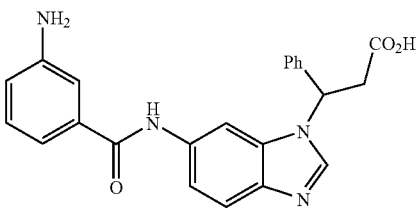

A solution of ethyl 3-{6-[(3-aminobenzoyl)amino]-1H-benzimidazol-1-yl}-3-phenylpropanoate (50 mg, 117 µmol) in hydrochloric acid (20 mL of a 5N solution) was stirred at room temperature for 96 hours. The solution was evaporated in vacuo, and the residue was purified by RP-HPLC to afford the title compound, [LCMS (Method A, Mobile Phase II) RT=3.36 min, MH⁺ 401].

Preparation 31

(a) Ethyl 3-{6-[(3-{[amino(imino)methyl]amino}benzoyl)amino]-1H-benzimidazol-1-yl}-3-phenylpropanoate

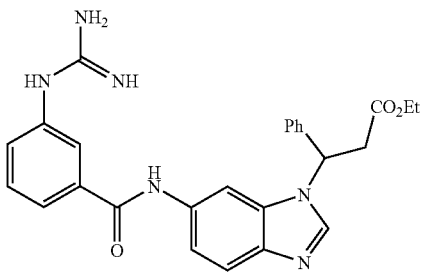

To a solution of ethyl 3-{6-[(3-aminobenzoyl)amino]-1H-benzimidazol-1-yl}-3-phenylpropanoate (70 mg, 164 µmol) in acetonitrile (1.2 mL) was added benzotriazolo-1-carboxamidine tosylate (57 mg, 163 µmol), and the resulting suspension heated to reflux for 16 hours. The suspension was then cooled to room temperature, evaporated in vacuo, and the residue was purified by RP-HPLC to afford the title compound, [LCMS (Method A, Mobile Phase II) RT=3.96 min, MH⁺ 471].

(b) Example 31b

3-{6-[(3-{[Amino(imino)methyl]amino}benzoyl)amino]-1H-benzimidazol-1-yl}-3-phenylpropanoic acid

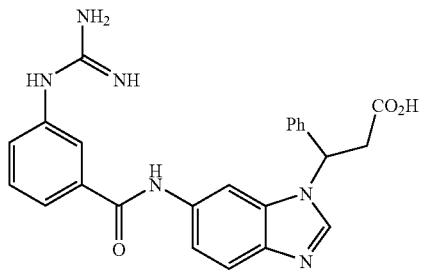

A solution of ethyl 3-{6-[(3-{[amino(imino)methyl]amino}benzoyl)amino]-1H-benzimidazol-1-yl}-3-phenylpropanoate (24 mg, 51 µmol) in hydrochloric acid (20 mL of a 5N solution) was stirred at room temperature for 72 hours. The solution was evaporated in vacuo, and the residue was purified by RP-HPLC to afford the title compound, [LCMS (Method A, Mobile Phase II) RT=2.96 min, MH⁺ 443].

Preparation 32

(a) Ethyl 3-{6-[(2-nitrobenzoyl)amino]-1H-benzimidazol-1-yl}-3-phenylpropanoate

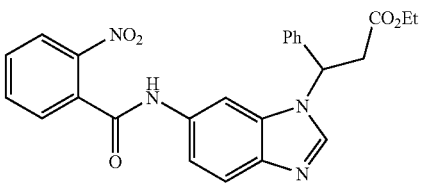

To a solution of ethyl 3-(6-amino-1H-benzimidazol-1-yl)-3-phenylpropanoate (200 mg, 647 µmol) in dichloromethane (15 mL) was added triethylamine (200 µL, 1.43 µmol) and 2-nitrobenzoyl chloride (190 µL, 1.43 mmol). The solution was stirred at room temperature for 96 hours, and was evaporated in vacuo. The residue was purified by flash column chromatography on silica gel, eluting with a mixture of dichloromethane and methanol (97:3) to afford the title compound, [LCMS (Method A, Mobile Phase II) RT=5.12 min, MH⁺ 459].

(b) Example 32b

3-{6-[(2-Nitrobenzoyl)amino]-1H-benzimidazol-1-yl}-3-phenylpropanoic acid & Example 32c: 3-{6-[(2-aminobenzoyl)amino]-1H-benzimidazol-1-yl}-3-phenylpropanoic acid

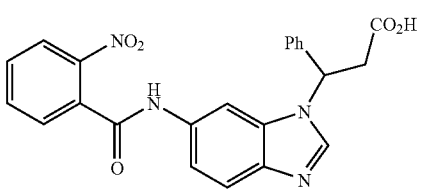

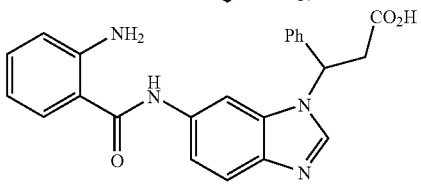

To a solution of ethyl 3-{6-[(2-nitrobenzoyl)amino]-1H-benzimidazol-1-yl}-3-phenylpropanoate (24 mg, 52 µmol) in a mixture of ethanol and water (5:1, 6 mL), was added palladium on carbon (50 mg, 10% w/w Pd) and ammonium formate (17 mg, 270 µmol). The suspension was heated to reflux for 2 hours, cooled to room temperature, filtered through a pad of Celite® and the filtrate was evaporated in vacuo. The residue was taken up in hydrochloric acid (20 mL of a 5N solution) was stirred at room temperature for 72 hours, evaporated in vacuo, and the residue was purified by RP-HPLC to afford the title compounds 3-{6-[(2-aminobenzoyl)amino]-1H-benzimidazol-1-yl}-3-phenylpropanoic acid, [LCMS (Method A, Mobile Phase II) RT=3.65 min, MH⁺ 401], and 3-{6-[(2-nitrobenzoyl)amino]-1H-benzimidazol-1-yl}-3-phenylpropanoic acid, [LCMS (Method A, Mobile Phase II) RT=3.58 min, MH⁺ 431].

Preparation 33

(a) Methyl 3-{6-[(anilinocarbonyl)amino]-1H-benzimidazol-1-yl}-3-phenylpropanoate

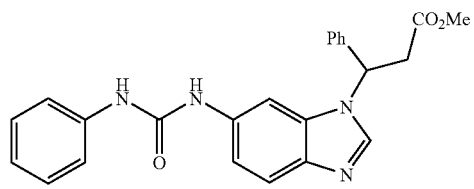

To a solution of ethyl 3-(6-amino-1H-benzimidazol-1-yl)-3-phenylpropanoate (150 mg, 485 μmol) in methanol (6 mL) was added phenyl isocyanate (50 μL, 460 μmol) and N,N-diisopropylethylamine (80 μL, 459 μmol). The solution was stirred at room temperature for 48 hours, and additional aliquots of phenyl isocyanate (10 μL, 92 μmol) and N,N-diisopropylethylamine (16 μL, 92 μmol) were added. The solution was stirred at room temperature for an additional 24 hours, and was then evaporated in vacuo. The residue was purified by flash column chromatography on silica gel, eluting with a mixture of dichloromethane and methanol (95:5) to afford the title compound, [LCMS (Method A, Mobile Phase II) RT 5.13 min, MH$^+$ 415].

(b) Example 33b

3-{6-[(Anilinocarbonyl)amino]-1H-benzimidazol-1-yl}-3-phenylpropanoic acid

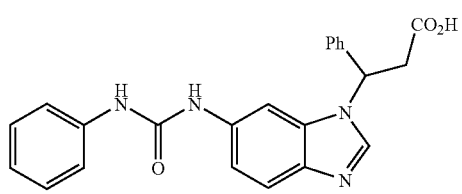

A solution of methyl 3-{6-[(anilinocarbonyl)amino]-1H-benzimidazol-1-yl}-3-phenylpropanoate (90 mg, 210 μmol) in a mixture of hydrochloric acid (20 mL of a 5N solution) and acetonitrile (10 mL) was stirred at room temperature for 72 hours. The solution was evaporated in vacuo to afford the title compound, [LCMS (Method A, Mobile Phase II) RT=3.77 min, MH$^+$ 401].

Example 34

3-{6-[(2-Phenoxybenzoyl)amino]-1H-benzimidazol-1-yl}-3-phenylpropanoic acid

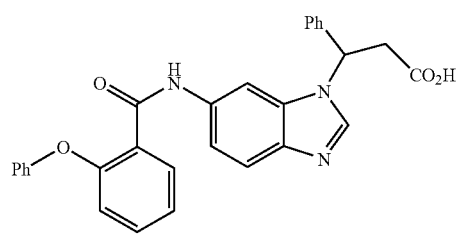

Using the procedure of Preparation 21, the title compound (48 mg) was prepared from ethyl 3-(6-amino-1H-benzimidazol-1-yl)-3-phenyl propanoate. [LCMS (Method A, Mobile Phase I) RT=4.76 min, MH$^+$ 478].

Example 35

3-{6-[(2,6-Dimethoxybenzoyl)amino]-1H-benzimidazol-1-yl}-3-phenylpropanoic acid

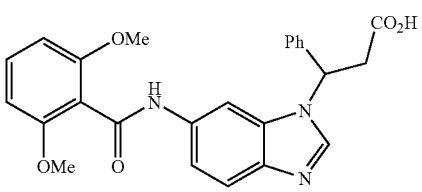

Using the procedure of Preparation 21, the title compound (35 mg) was prepared from ethyl 3-(6-amino-1H-benzimidazol-1-yl)-3-phenyl propanoate and 2,6-dimethoxybenzoic acid, and purified by RP-HPLC. [LCMS (Method A, Mobile Phase I) RT=3.71 min, MH$^+$ 446].

Example 36

3-{6-[(1H-Indol-3-ylacetyl)amino]-1H-benzimidazol-1-yl}-3-phenylpropanoic acid

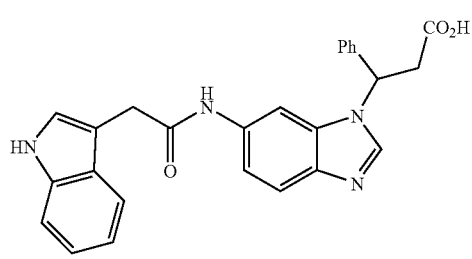

Using the procedure of Preparation 21, the title compound (22 mg) was prepared from ethyl 3-(6-amino-1H-benzimidazol-1-yl)-3-phenyl propanoate and indole 3-acetic acid, and purified by RP-HPLC. [LCMS (Method A, Mobile Phase I) RT=4.08 min, MH$^+$ 439].

Example 37

3-(6-{[3-(1H-Indol-3-yl)propanoyl]amino}-1H-benzimidazol-1-yl)-3-phenylpropanoic acid

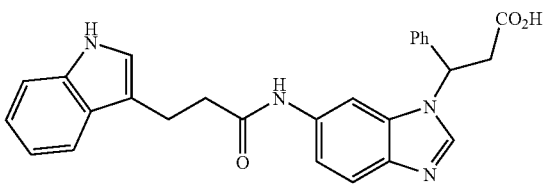

Using a similar procedure to that described in Preparation 21, the title compound (25 mg) was prepared from ethyl 3-(6-amino-1H-benzimidazol-1-yl)-3-phenylpropanoate and 3-indolepropionic acid. Hydrolysis of the intermediate ethyl 3-(6-{[3-(1H-indol-3-yl)propanoyl]amino}-1H-benzimidazol-1-yl)-3-phenylpropanoate in this case was carried out using an aqueous solution of sodium hydroxide (2N), followed by RP-HPLC purification of the concentrated residue. [LCMS (Method A, Mobile Phase I) RT=4.29 min, MH+ 453].

Example 38

3-Phenyl-3-[6-({[2-(phenylsulfanyl)-3-pyridinyl]carbonyl}amino)-1H-benzimidazol-1-yl]propanoic acid

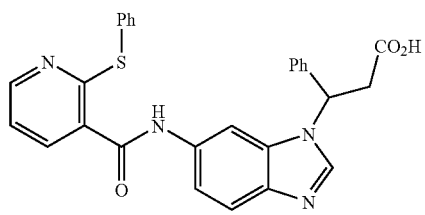

Using the procedure of Preparation 21, the title compound (49 mg) was prepared from ethyl 3-(6-amino-1H-benzimidazol-1-yl)-3-phenyl propanoate and 2-(phenylsulfanyl)nicotinic acid, and purified by RP-HPLC. [LCMS (Method A, Mobile Phase I) RT=4.37 min, MH+ 495].

Example 39

3-(6-{[2,4-Bis(trifluoromethyl)benzoyl]amino}-1H-benzimidazol-1-yl)-3-phenylpropanoic acid

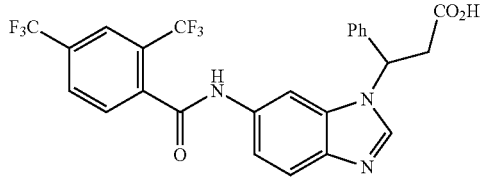

Using the procedure of Preparation 21, the title compound (23 mg) was prepared from ethyl 3-(6-amino-1H-benzimidazol-1-yl)-3-phenyl propanoate and 2,4-bis(trifluoromethyl)benzoic acid, and purified by RP-HPLC. [LCMS (Method A, Mobile Phase I) RT=5.04 min, MH+ 522].

Example 40

3-{6-[(2-Bromo-5-methoxybenzoyl)amino]-1H-benzimidazol-1-yl}-3-phenylpropanoic acid

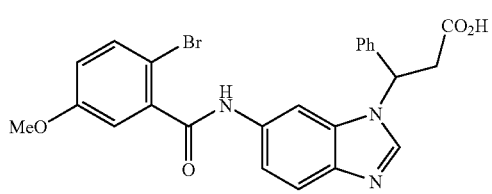

Using the procedure of Preparation 21, the title compound (56 mg) was prepared from ethyl 3-(6-amino-1H-benzimidazol-1-yl)-3-phenylpropanoate and 2-bromo-5-methoxybenzoic acid, and purified by RP-HPLC. [LCMS (Method A, Mobile Phase I) RT=4.35 min, MH+ 496].

Example 41

3-{6-[(2-Fluoro-6-iodobenzoyl)amino]-1H-benzimidazol-1-yl}-3-phenylpropanoic acid

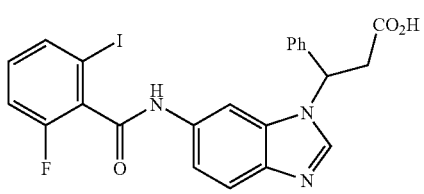

Using the procedure of Preparation 21, the title compound (48 mg) was prepared from ethyl 3-(6-amino-1H-benzimidazol-1-yl)-3-phenylpropanoate and 2-fluoro-6-iodobenzoic acid. [LCMS (Method A, Mobile Phase I) RT=4.33 min, MH+ 530].

Example 42

3-Phenyl-3-(6-{[(4-phenyl-1,2,3-thiadiazol-5-yl)carbonyl]amino}-1H-benzimidazol-1-yl)propanoic acid

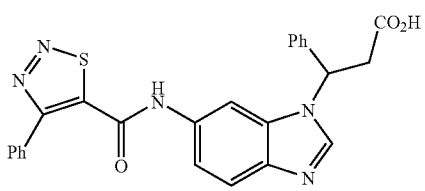

Using the procedure of Preparation 21, the title compound (14 mg) was prepared from ethyl 3-(6-amino-1H-benzimidazol-1-yl)-3-phenyl propanoate and 4-phenyl-1,2,3-thiadiazole-5-carboxylic acid, and purified by RP-HPLC. [LCMS (Method A, Mobile Phase I) RT=4.35 min, MH+ 470].

Example 43

3-{6-[(3-Bromo-2,6-dimethoxybenzoyl)amino]-1H-benzimidazol-1-yl}-3-phenylpropanoic acid

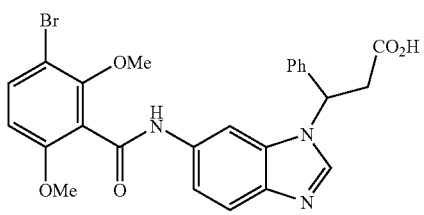

Using the procedure of Preparation 21, the title compound (24 mg) was prepared from ethyl 3-(6-amino-1H-benzimidazol-1-yl)-3-phenylpropanoate and 3-bromo-2,6-dimethoxybenzoic acid, and purified by RP-HPLC. [LCMS (Method A, Mobile Phase I) RT=4.43 min, MH$^+$ 526].

Example 44

3-Phenyl-3-{6-[(2,3,5-trichloro-6-hydroxybenzoyl)amino]-1H-benzimidazol-1-yl}propanoic acid

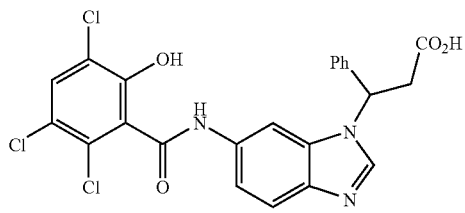

Using a similar procedure to that described in Preparation 21, the title compound (19 mg) was prepared from ethyl 3-(6-amino-1H-benzimidazol-1-yl)-3-phenylpropanoate and 3,5,6-trichlorosalicylic acid (HATU was substituted for TBTU), and purified by RP-HPLC. [LCMS (Method A, Mobile Phase I) RT=4.54 min, MH$^+$ 506].

Preparation 45

(a) Methyl (3R)-3-(2,4-dinitroanilino)-3-phenylpropanoate

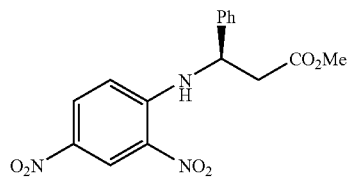

To a solution of 2,4-dinitrochlorobenzene (5.1 g, 25 mmol) in methanol (60 mL) was added methyl (3R)-3-amino-3-phenylpropanoate (3.75 g, 21 mmol, prepared according to Davies et. al., Tetrahedron Asymm., 1991, 183) and triethylamine (2.9 mL, 21 mmol). The mixture was brought to reflux, heating in total for 5 hours, and was then cooled and evaporated in vacuo. The residue was purified by flash column chromatography on silica gel, eluting with a mixture of dichloromethane and methanol (95:5), to afford the title compound, [LCMS (Method C, Mobile Phase I) RT=3.22 mins, MH$^+$ 346].

(b) Methyl (3R)-3-(2-amino-4-nitroanilino)-3-phenylpropanoate

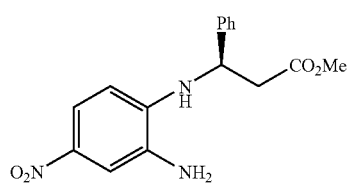

To a solution of methyl (3R)-3-(2,4-dinitroanilino)-3-phenylpropanoate (3.14 g, 9.1 mmol) in a mixture of ethanol (100 mL) and water (10 mL) was added ammonium formate (2.3 g, 36 mmol) and palladium on carbon (300 mg, 10% w/w Pd). The mixture was stirred at room temperature for 2 hours, then filtered through a pad of Celite®, evaporated in vacuo. The residue was purified by flash column chromatography on silica gel, eluting with a mixture of dichloromethane and methanol (95:5), to afford the title compound, [LCMS (Method C, Mobile Phase I) RT=2.94 mins, MH$^+$ 316].

(c) Methyl (3R)-3-(5-nitro-1H-benzimidazol-1-yl)-3-phenylpropanoate

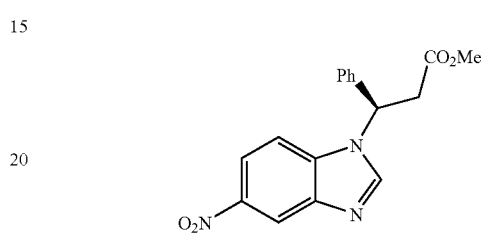

To a solution of methyl (3R)-3-(2-amino-4-nitroanilino)-3-phenylpropanoate (2.10 g, 6.7 mmol) in 2-ethoxyethanol (65 mL) was added formamidine acetate (2.8 g, 26.6 mmol), and the mixture heated to 85° C. for 5 hours. The mixture was then cooled to room temperature, evaporated in vacuo, and the residue purified by flash column chromatography on silica gel, eluting with a mixture of dichloromethane and methanol (95:5) to afford a mixture of the title compound and the corresponding 2-ethoxyethanol ester, which was used directly without any additional purification. [LCMS (Method C, Mobile Phase I) RT=2.86 mins (broad), MH$^+$ 326 (Me-ester) and 384 (EtOCH$_2$CH$_2$-ester)].

(d) Methyl (3R)-3-(5-amino-1H-benzimidazol-1-yl)-3-phenylpropanoate

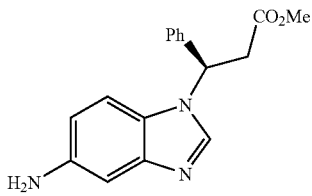

To a solution of the crude mixture of methyl (3R)-3-(5-nitro-1H-benzimidazol-1-yl)-3-phenylpropanoate and the corresponding 2-ethoxyethanol ester (714 mg, ca. 2.2 mmol) in a mixture of 1,4-dioxane (10 mL) and water (10 mL) was added concentrated ammonia solution (0.3 mL) and sodium dithionite (3.06 g, 17.6 mmol). The solution was stirred at room temperature for 3 hours, then diluted with brine, and extracted with ethyl acetate. The combined ethyl acetate extracts were dried over anhydrous magnesium sulfate, filtered, and evaporated in vacuo. The residue was purified by flash column chromatography on silica gel, gradient eluting with a mixture of dichloromethane and methanol (95:5, then 9:1), to afford a mixture of the title compound and the corresponding 2-ethoxyethanol ester, which was used directly without any additional purification. [LCMS (Method C, Mobile Phase I) RT=1.95 mins, MH$^+$ 296 (Me-ester) and RT=2.13 mins, MH$^+$ 354 (EtOCH$_2$CH$_2$-ester)].

(e) Methyl (3R)-3-{5-[(anilinocarbonyl)amino]-1H-benzimidazol-1-yl}-3-phenylpropanoate

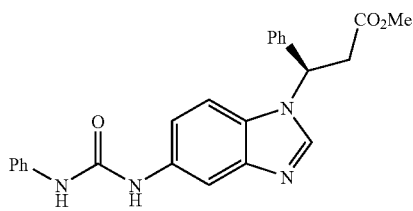

To a solution of the crude mixture of methyl (3R)-3-(5-amino-1H-benzimidazol-1-yl)-3-phenylpropanoate and the corresponding 2-ethoxyethanol ester (186 mg, ca. 629 µmol) in methanol (5.5 mL) was added N,N-diisopropylamine (132 µL, 750 µmol) and phenyl isocyanate (82 µL, 750 µmol). The solution was stirred at room temperature for 12 hours, then evaporated in vacuo, and purified by flash column chromatography on silica gel, eluting with a mixture of dichloromethane and methanol (95:5) to afford the title compound, [LCMS (Method C, Mobile Phase I) RT=2.33 mins, MH$^+$ 415].

(f) Example 45f (3R)-3-{5-[(Anilinocarbonyl)amino]-1H-benzimidazol-1-yl}-3-phenylpropanoic acid

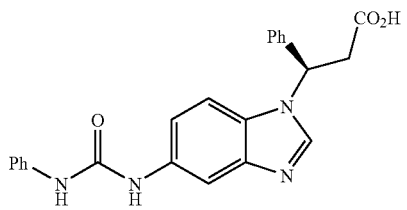

A solution of methyl (3R)-3-{5-[(anilinocarbonyl)amino]-1H-benzimidazol-1-yl}-3-phenylpropanoate (204 mg, 492 µmol) in a mixture of tetrahydrofuran (2 mL), acetonitrile (20 mL) and hydrochloric acid (50 mL of a 5N solution) was stirred at room temperature for 110 hours. The solution was evaporated in vacuo to afford the title compound, [LCMS (Method C, Mobile Phase I) RT=2.25 min, MH$^+$ 401.34].

Example 46

(3S)-3-(5-Nitro-1H-benzimidazol-1-yl)-3-phenylpropanoic acid

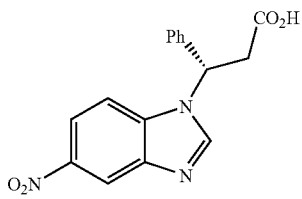

Using a similar procedure to that described in Preparation 45, the title compound (19 mg) was prepared from methyl (3S)-3-amino-3-phenylpropanoate and 2,4-dinitrochlorobenzene, and liberated as the free acid using a procedure similar to that described in Preparation II. [LCMS (Method C, Mobile Phase I) RT=2.60 min, MH$^+$ 312].

Preparation 47

(a) Methyl 3-(1,1'-biphenyl)-4-yl-3-(2,4-dinitroanilino)propanoate

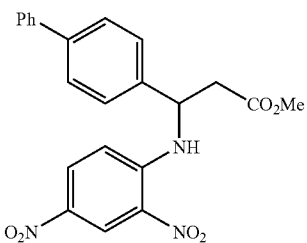

To a solution of 2,4-dinitrofluorobenzene (247 mg, 847 µmol) in methanol (2 mL) was added N,N-diisopropylethylamine (147 µL, 844 µmol) and methyl 3-amino-3-(1,1'-biphenyl)-4-ylpropanoate (158 mg, 849 µmol). The solution was stirred at room temperature for 72 hours, then evaporated in vacuo. The residue was purified by flash column chromatography on silica gel, eluting with a mixture of petroleum ether and dichloromethane (1:1 to 0:1), to afford the title compound, [LCMS (Method B, Mobile Phase I) RT=3.81 min, MH$^+$ 422].

(b) Methyl 3-(2-amino-4-nitroanilino)-3-(1,1'-biphenyl)-4-ylpropanoate

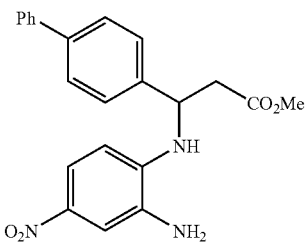

To a solution of methyl 3-(1,1'-biphenyl)-4-yl-3-(2,4-dinitroanilino)propanoate (320 mg, 760 µmol) in ethanol (3 mL) was added palladium on carbon (64 mg, 10% active Pd), ammonium formate (239 mg, 3.80 mmol) and water (1 mL). The solution was stirred at room temperature for 1.5 hour, and was then filtered through a pad of Celite®. The filter pad was washed with ethyl acetate, and the filtrate evaporated in vacuo. The residue was purified by flash column chromatography on silica gel, eluting with dichloromethane, to afford the title compound, [LCMS (Method A, Mobile Phase I) RT=3.44 min, MH$^+$ 392].

(c) Methyl 3-(1,1'-biphenyl)-4-yl-3-(5-nitro-1H-benzimidazol-1-yl)propanoate

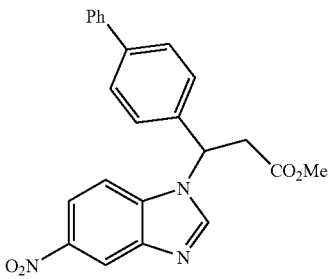

To a solution of methyl 3-(2-amino-4-nitroanilino)-3-(1,1'-biphenyl)-4-ylpropanoate (60 mg, 153 μmol) in 2-ethoxyethanol (1 mL) was added formamidine acetate (48 mg, 461 μmol). The solution was heated to reflux for 6 hours, then cooled to room temperature, and evaporated in vacuo. The residue was purified by flash column chromatography on silica gel, eluting with dichloromethane, to afford the title compound, [LCMS (Method A, Mobile Phase I) RT=6.11 min, MH$^+$ 402].

(d) Example 47d 3-(1,1'-Biphenyl)-4-yl-3-(5-nitro-1H-benzimidazol-1-yl)propanoic acid

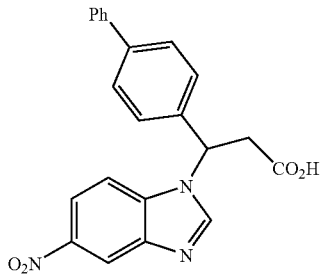

A solution of methyl 3-(1,1'-biphenyl)-4-yl-3-(5-nitro-1H-benzimidazol-1-yl)propanoate (21 mg, 52 μmol) in hydrochloric acid (10 mL of a 5N solution) was stirred at room temperature for 48 hours. The solution was evaporated in vacuo to afford the title compound, [LCMS (Method A, Mobile Phase I) RT=5.63 min, MH$^+$ 388].

Preparation 48

(a) Methyl 3-(5-amino-1H-benzimidazol-1-yl)-3-(1,1'-biphenyl)-4-ylpropanoate

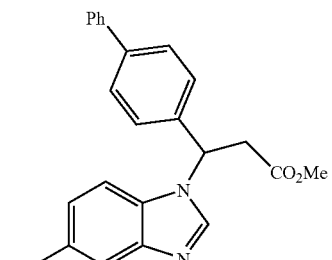

To a solution of methyl 3-(1,1'-biphenyl)-4-yl-3-(5-nitro-1H-benzimidazol-1-yl)propanoate (47 mg, 117 μmol) in ethanol (2 mL) was added palladium on carbon (9.0 mg, 10% active Pd), ammonium formate (37 mg, 587 μmol) and water (0.5 mL). The solution was heated at reflux for 4 hours, the cooled to room temperature, and filtered through Celite®. The filtrate was evaporated in vacuo, and the residue was purified by flash column chromatography on silica gel, eluting with a mixture of dichloromethane and methanol (97:3) to afford the title compound, [LCMS (Method B, Mobile Phase I) RT=2.26 min, MH$^+$ 372].

(b) Example 48b 3-(5-Amino-1H-benzimidazol-1-yl)-3-(1,1'-biphenyl)-4-ylpropanoic acid

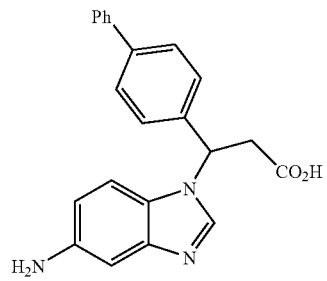

A solution of methyl 3-(5-amino-1H-benzimidazol-1-yl)-3-(1,1'-biphenyl)-4-ylpropanoate (10 mg, 27 μmol) in hydrochloric acid (10 mL of a 5N solution) was stirred at room temperature for 48 hours. The solution was then evaporated in vacuo to afford the title compound, [LCMS (Method A, Mobile Phase I) RT=4.11 min, MH$^+$ 358].

Preparation 49

(a) Methyl 3-(1,1'-biphenyl)-4-yl-3-{5-[(phenylsulfonyl)amino]-1H-benzimidazol-1-yl}propanoate

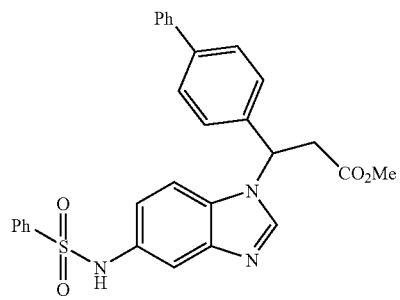

To a solution of methyl 3-(5-amino-1H-benzimidazol-1-yl)-3-(1,1'-biphenyl)-4-ylpropanoate (15 mg, 40 μmol) in dichloromethane (500 μL) was added benzenesulfonyl chloride (6.0 μL, 47 μmol) and N,N-diisopropylethylamine (8.0 μL, 46 μmol). The solution was stirred at room temperature for 48 hours, and was then evaporated in vacuo. The residue was purified by flash column chromatography on silica gel, eluting with a mixture of dichloromethane and methanol (96:4), to afford the title compound, [LCMS (Method A, Mobile Phase I) RT=5.50 min, MH$^+$ 513].

(b) Example 49b

3-[1,1'-Biphenyl]-4-yl-3-{5-[(phenylsulfonyl)amino]-1H-benzimidazol-1-yl}propanoic acid

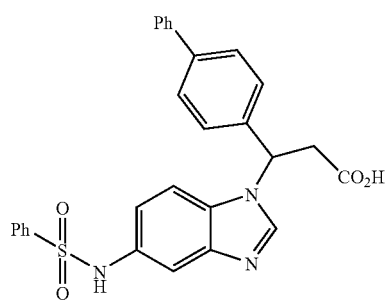

A solution of methyl 3-(1,1'-biphenyl)-4-yl-3-{5-[(phenylsulfonyl)amino]-1H-benzimidazol-1-yl}propanoate (12 mg, 23 µmol) in hydrochloric acid (10 mL of a 5N solution) was stirred at room temperature for 120 hours. The solution was evaporated in vacuo to afford the title compound, [LCMS (Method A, Mobile Phase I) RT=5.04 min, MH$^+$ 498].

Example 50

3-(5-Nitro-1H-benzimidazol-1-yl)-3-(3-pyridinyl)propanoic acid

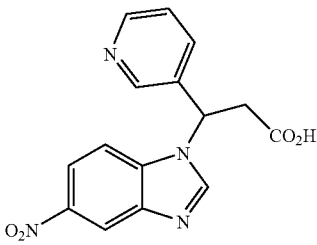

Using the procedure of Preparation 47, the title compound, (28 mg), was prepared from methyl 3-amino-3-(3-pyridinyl)propanoate. [LCMS (Method A, Mobile Phase I) RT=3.09 min, MH$^+$ 313].

Example 51

3-(5-Amino-1H-benzimidazol-1-yl)-3-(3-pyridinyl)propanoic acid

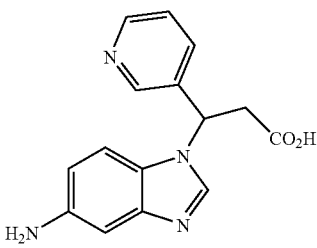

Using the procedure of Preparation 48, the title compound, (27 mg), was prepared from methyl 3-(5-nitro-1H-benzimidazol-1-yl)-3-(3-pyridinyl)propanoate. [LCMS (Method A, Mobile Phase I) RT=1.12 min, MH$^+$ 283].

Example 52

3-{5-[(Phenylsulfonyl)amino]-1H-benzimidazol-1-yl}-3-(3-pyridinyl)propanoic acid

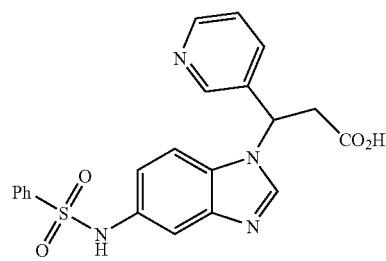

Using the procedure of Preparation 49, the title compound, (40 mg), was prepared from methyl 3-(5-amino-1H-benzimidazol-1-yl)-3-(3-pyridinyl)propanoate. [LCMS (Method A, Mobile Phase I) RT=3.17 min, MH$^+$ 423].

Example 53

3-(2-Naphthyl)-3-(5-nitro-1H-benzimidazol-1-yl)propanoic acid

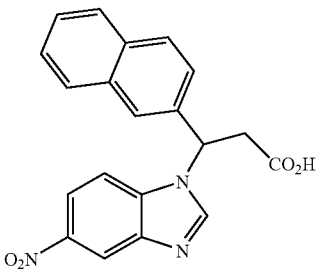

Using the procedure of Preparation 47, the title compound, (28 mg), was prepared from methyl 3-amino-3-(2-naphthyl)propanoate. [LCMS (Method A, Mobile Phase I) RT=5.27 min, MH$^+$ 362].

Example 54

3-(5-Amino-1H-benzimidazol-1-yl)-3-(2-naphthyl)propanoic acid

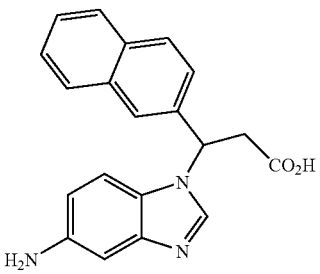

Using the procedure of Preparation 48, the title compound, (16 mg), was prepared from methyl 3-(2-naphthyl)-3-(5-nitro-1H-benzimidazol-1-yl)propanoate. [LCMS (Method A, Mobile Phase I) RT=3.62 min, MH+ 332].

Example 55

3-(2-Naphthyl)-3-{5-[(phenylsulfonyl)amino]-1H-benzimidazol-1-yl}propanoic acid

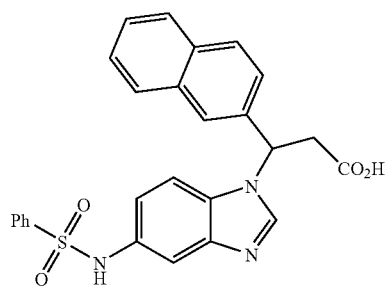

Using the procedure of Preparation 49, the title compound, (3.0 mg), was prepared from methyl 3-(5-amino-1H-benzimidazol-1-yl)-3-(2-naphthyl)propanoate. The title compound was purified by RP-HPLC. [LCMS (Method A, Mobile Phase I) RT=4.65 min, MH+ 472].

Example 56

3-(1-Naphthyl)-3-(5-nitro-1H-benzimidazol-1-yl)propanoic acid

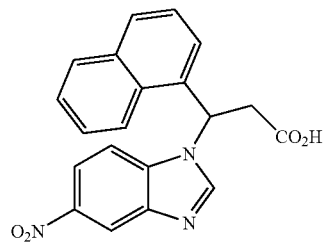

Using the procedure of Preparation 47, the title compound, (4.0 mg), was prepared from methyl 3-amino-3-(1-naphthyl)propanoate. The title compound was purified by RP-HPLC. [LCMS (Method A, Mobile Phase I) RT=5.18 min, MH+ 362].

Example 57

3-(5-Amino-1H-benzimidazol-1-yl)-3-(1-naphthyl)propanoic acid

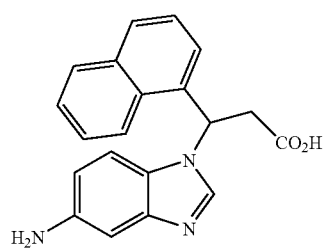

Using the procedure of Preparation 48, the title compound, (35 mg), was prepared from methyl 3-(1-naphthyl)-3-(5-nitro-1H-benzimidazol-1-yl)propanoate. [LCMS (Method A, Mobile Phase I) RT=3.41 min, MH+ 332].

Example 58

3-(2-Naphthyl)-3-{5-[(phenylsulfonyl)amino]-1H-benzimidazol-1-yl}propanoic acid

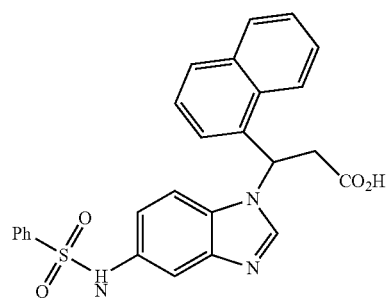

Using the procedure of Preparation 49, the title compound, (11 mg), was prepared from methyl 3-(5-amino-1H-benzimidazol-1-yl)-3-(1-naphthyl)propanoate. [LCMS (Method A, Mobile Phase I) RT=4.68 min, MH+ 472].

Example 59

3-(5-Amino-1H-benzimidazol-1-yl)-3-(4-methoxyphenyl)propanoic acid

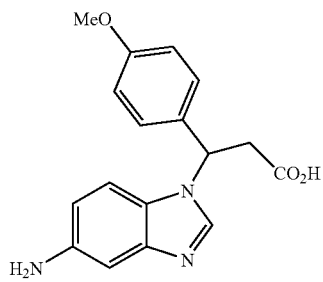

Using a combination of Preparations 47 and 48, the title compound, (3.0 mg), was prepared from methyl 3-amino-3-(4-methoxyphenyl)propanoate. [LCMS (Method A, Mobile Phase I) RT=2.90 min, MH+ 312].

Example 60

3-(4-Methoxyphenyl)-3-{5-[(phenylsulfonyl)amino]-1H-benzimidazol-1-yl}propanoic acid

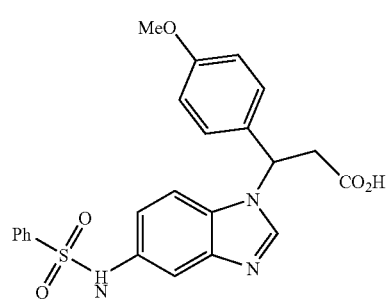

Using the procedure of Preparation 49, the title compound, (4.0 mg), was prepared from methyl 3-(5-amino-1H-benzimidazol-1-yl)-3-(4-methoxyphenyl)propanoate. [LCMS (Method A, Mobile Phase I) RT=4.17 min, MH⁺ 452].

Preparation 61

(a) 4-[(3-Ethoxy-3-oxo-1-phenylpropyl)amino]-3-nitrobenzoic acid

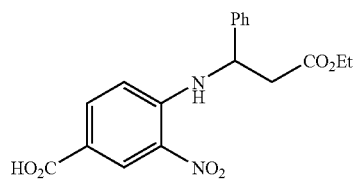

To a solution of 4-fluoro-3-nitrobenzoic acid (185 mg, 1.00 mmol) in DMSO (2 mL) was added ethyl-3-amino-3-phenylpropanoate (231 mg, 1.20 mmol) and potassium carbonate (166 mg, 1.20 mmol). The suspension was heated to 100° C. for 3 hours, cooled to room temperature and diluted with water. The solution was partitioned between ethyl acetate and dilute hydrochloric acid (2N), and the aqueous phase separated, and extracted with ethyl acetate. The combined organic layers were dried over anhydrous magnesium sulfate, filtered, and evaporated in vacuo. The residue was purified by flash column chromatography on silica gel, eluting with a mixture of dichloromethane and methanol (96:4) to afford the title compound, [LCMS (Method A, Mobile Phase II) RT=4.19 min, MH⁺ 359].

(b) 3-Amino-4-[(3-ethoxy-3-oxo-1-phenylpropyl)amino]benzoic acid

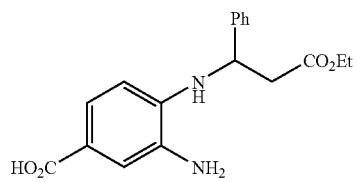

To a solution of 4-[(3-ethoxy-3-oxo-1-phenylpropyl)amino]-3-nitrobenzoic acid, (70 mg, 196 µmol) in a mixture of 1,4-dioxane, water and 0.88 ammonia solution (3:3:0.2, 6.2 mL) was added sodium dithionite (272 mg, 1.52 mmol). The resulting solution was stirred at room temperature for 20 hours, and then extracted with ethyl acetate. The combined extracts were dried over anhydrous magnesium sulfate, filtered, and evaporated in vacuo, to afford the title compound, [LCMS (Method A, Mobile Phase II) RT=3.93 min, MH⁺ 329].

(c) 1-(3-Ethoxy-3-oxo-1-phenylpropyl)-1H-benzimidazole-5-carboxylic acid

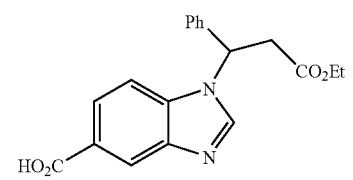

To a solution of 3-amino-4-[(3-ethoxy-3-oxo-1-phenylpropyl)amino]benzoic acid (57 mg, 174 µmol) in 2-ethoxyethanol (1.2 mL) was added formamidine acetate (27 mg, 259 µmol), and the solution heated to 70° C. for 1 hour. The solution was evaporated in vacuo, and the residue purified by flash column chromatography on silica gel, eluting with a mixture of dichloromethane and methanol (19:1) to afford the title compound, [LCMS (Method A, Mobile Phase II) RT=4.46 min, MH⁺ 339].

(d) Example 61d 1-(2-Carboxy-1-phenylethyl)-1H-benzimidazole-5-carboxylic acid

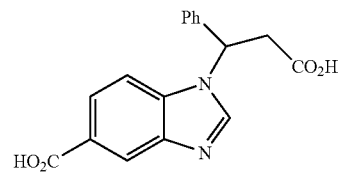

A solution of 1-(3-ethoxy-3-oxo-1-phenylpropyl)-1H-benzimidazole-5-carboxylic acid (40 mg, 118 µmol) in a mixture of hydrochloric acid (10 mL of a 5N solution) and acetonitrile (6 mL) was stirred at room temperature for 72 hours. The solution was evaporated in vacuo to afford the title compound, [LCMS (Method A, Mobile Phase I) RT=5.26 min, MH⁺ 311].

Preparation 62

(a) Ethyl 3-[5-(anilinocarbonyl)-1H-benzimidazol-1-yl]-3-phenylpropanoate

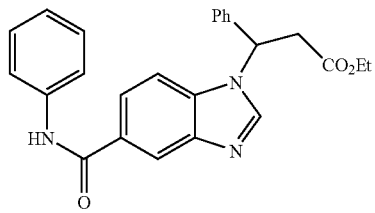

To a solution of 1-(3-ethoxy-3-oxo-1-phenylpropyl)-1H-benzimidazole-5-carboxylic acid (50 mg, 148 µmol) in DMF (3 µL) was added N,N-diisopropylethylamine (50 µL, 287 µmol) and TBTU (57 mg, 177 µmol). The solution was stirred at room temperature for 0.5 hour, aniline (20 µL, 220 µmol) was added, and stirring continued at room temperature for 72 hours. The solution was evaporated in vacuo, and the residue was purified by flash column chromatography on silica gel, eluting with a mixture of dichloromethane and methanol (98:2) to afford the title compound, [LCMS (Method A, Mobile Phase I) RT=5.30 min, MH⁺ 414].

(b) Example 62b

3-[5-(Anilinocarbonyl)-1H-benzimidazol-1-yl]-3-phenylpropanoic acid

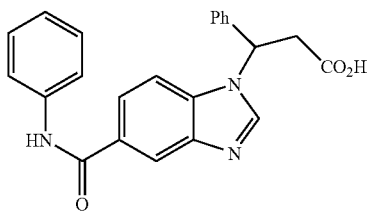

A solution of ethyl 3-[5-(anilinocarbonyl)-1H-benzimidazol-1-yl]-3-phenylpropanoate (27 mg, 65 μmol) in a mixture of hydrochloric acid (20 mL of a 5N solution) and acetonitrile (15 mL) was stirred at room temperature for 96 hours. The resulting suspension was then concentrated and filtered, and the resulting solid dried in vacuo over $P_2O_5$ to afford the title compound, [LCMS (Method A, Mobile Phase I) RT=4.54 min, MH$^+$ 386].

Preparation 63

(a) Ethyl 3-phenyl-3-(5-{[4-(2-pyrazinyl)-1-piperazinyl]carbonyl}-1H-benzimidazol-1-yl)propanoate

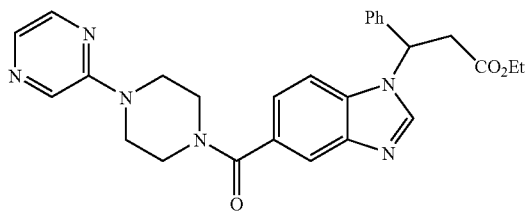

To a solution of 1-(3-ethoxy-3-oxo-1-phenylpropyl)-1H-benzimidazole-5-carboxylic acid (70 mg, 207 μmol) in DMF (4 mL) was added N,N-diisopropylethylamine (40 μL, 229 μmol) and TBTU (80 mg, 249 μmol). The solution was stirred at room temperature for 0.5 hour, 1-(2-pyrazinyl) piperazine (41 mg, 249 μmol) was added, and stirring continued at room temperature for 24 hours. The solution was evaporated in vacuo, and the residue was purified by flash column chromatography on silica gel, eluting with a mixture of dichloromethane and methanol (95:5) to afford the title compound, [LCMS (Method A, Mobile Phase I) RT=4.33 min, MH$^+$ 485].

(b) Example 63b

3-Phenyl-3-(5-{[4-(2-pyrazinyl)-1-piperazinyl]carbonyl}-1H-benzimidazol-1-yl)propanoic acid

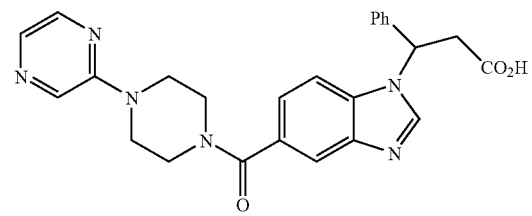

A solution of ethyl 3-phenyl-3-(5-{[4-(2-pyrazinyl)-1-piperazinyl]carbonyl}-1H-benzimidazol-1-yl) propanoate (92 mg, 190 μmol) in a mixture of hydrochloric acid (20 mL of a 5N solution) and acetonitrile (15 mL) was stirred at room temperature for 72 hours. The resulting suspension was then evaporated in vacuo, and the residue was purified by RP-HPLC to afford the title compound, [LCMS (Method A, Mobile Phase I) RT=3.64 min, MH$^+$ 457].

Library Experimental Details

Generic Procedure for Sulfonamide Synthesis

To a solution of N,N-diisopropylethylamine in 1,2-dichloroethane (30 μL, 10 μmol) was added ethyl 3-(5-amino-1H-benzimidazol-1-yl)-3-phenylpropanoate in 1,2-dichloroethane (30 μL, 10 μmol). The appropriate sulfonyl chloride in 1,2-dichloroethane (30 μL, 10 μmol) was then added, and the mixture agitated for 48 hours. The solution was evaporated in vacuo, and the residue taken up into acetonitrile (50 μL). Hydrochloric acid (100 μL of a 5N solution) was added, and the reaction agitated for a further 48 hours. The resulting solution was then evaporated in vacuo, to afford the title compounds.

| Ex. | IUPAC Name | LCMS MH$^+$/MH$^-$ | HPLC RT/min (Method A, Mobile Phase II) |
|---|---|---|---|
| L1 | 3-[5-({[4-amino-3-chlorophenyl]sulfonyl}amino)-1H-benzimidazol-1-yl]-3-phenylpropanoic acid | 471 | 3.63 |
| L2 | 3-{5-[(2,1,3-benzothiadiazol-4-ylsulfonyl)amino]-1H-benzimidazol-1-yl}-3-phenylpropanoic acid | 480 | 3.62 |
| L3 | 3-phenyl-3-[5-({[4-(trifluoromethoxy)phenyl]sulfonyl}amino)-1H-benzimidazol-1-yl]propanoic acid | 506 | 4.27 |
| L4 | 3-(5-{[(4-bromophenyl)sulfonyl]amino}-1H-benzimidazol-1-yl)-3-phenylpropanoic acid | 502 | 4.01 |
| L5 | 3-{5-[({5-[2-(methylsulfanyl)-4-pyrimidinyl]-2-thienyl}sulfonyl)amino]-1H-benzimidazol-1-yl}-3-phenylpropanoic acid | 552 | 4.12 |
| L6 | 3-(5-{[(2,3,4,5,6-pentamethylphenyl)sulfonyl]amino}-1H-benzimidazol-1-yl)-3-phenylpropanoic acid | 492 | 4.32 |
| L7 | 3-phenyl-3-{5-[(phenylsulfonyl)amino]-1H-benzimidazol-1-yl}propanoic acid | 422 | 3.66 |
| L8 | 3-(5-{[(4-tert-butylphenyl)sulfonyl]amino}-1H-benzimidazol-1-yl)-3-phenylpropanoic acid | 478 | 4.35 |

-continued

| Ex. | IUPAC Name | LCMS MH+/MH− | HPLC RT/min (Method A, Mobile Phase II) |
|---|---|---|---|
| L9 | 3-{5-[(1-naphthylsulfonyl)amino]-1H-benzimidazol-1-yl}-3-phenylpropanoic acid | 472 | 4.03 |
| L10 | 3-{5-[(2-naphthylsulfonyl)amino]-1H-benzimidazol-1-yl}-3-phenylpropanoic acid | 472 | 4.07 |
| L11 | 3-[5-({[5-(dimethylamino)-1-naphthyl]sulfonyl}amino)-1H-benzimidazol-1-yl]-3-phenylpropanoic acid | 515 | 4.24 |
| L12 | 3-(5-{[(4-fluorophenyl)sulfonyl]amino}-1H-benzimidazol-1-yl)-3-phenylpropanoic acid | 440 | 3.77 |
| L13 | 3-(5-{[(4-nitrophenyl)sulfonyl]amino}-1H-benzimidazol-1-yl)-3-phenylpropanoic acid | 467 | 3.90 |
| L14 | 3-[5-({[2-(acetylamino)-4-methyl-1,3-thiazol-5-yl]sulfonyl}amino)-1H-benzimidazol-1-yl]-3-phenylpropanoic acid | 500 | 3.39 |
| L15 | 3-({[1-(2-carboxy-1-phenylethyl)-1H-benzimidazol-5-yl]amino}sulfonyl)benzoic acid | 466 | 2.77 |
| L16 | 3-[5-({[5-(3-isoxazolyl)-2-thienyl]sulfonyl}amino)-1H-benzimidazol-1-yl]-3-phenylpropanoic acid | 495 | 3.83 |
| L17 | 3-(5-{[(3,5-dimethyl-4-isoxazolyl)sulfonyl]amino}-1H-benzimidazol-1-yl)-3-phenylpropanoic acid | 441 | 3.65 |
| L18 | 3-(5-({[4-aminophenyl]sulfonyl}amino)-1H-benzimidazol-1-yl)-3-phenylpropanoic acid | 437 | 3.31 |
| L19 | 3-(5-{[(1-methyl-1H-imidazol-4-yl)sulfonyl]amino}-1H-benzimidazol-1-yl)-3-phenylpropanoic acid | 426 | 3.02 |
| L20 | 3-phenyl-3-{5-[(2-thienylsulfonyl)amino]-1H-benzimidazol-1-yl}propanoic acid | 428 | 3.64 |
| L21 | 3-{5-[(methylsulfonyl)amino]-1H-benzimidazol-1-yl}-3-phenylpropanoic acid | 360 | 3.05 |
| L22 | 3-(5-({[4-(methylsulfonyl)phenyl]sulfonyl}amino)-1H-benzimidazol-1-yl]-3-phenylpropanoic acid | 500 | 3.53 |
| L23 | 3-phenyl-3-[5-({[2-(trifluoroacetyl)-1,2,3,4-tetrahydro-7-isoquinolinyl]sulfonyl}amino)-1H-benzimidazol-1-yl]propanoic acid | 573 | 4.07 |

Generic Procedure for Urea Synthesis

To a solution of ethyl 3-(5-amino-1H-benzimidazol-1-yl)-3-phenylpropanoate in 1,2-dichloroethane (30 μL, 10 μmol) was added the appropriate isocyanate in 1,2-dichloroethane (30 μL, 10 μmol), and the mixture agitated for 48 hours. The solution was evaporated in vacuo, and the residue taken up into acetonitrile (50 μL). Hydrochloric acid (100 μL of a 5N solution) was added, and the reaction agitated for a further 48 hours. The resulting solution was then evaporated in vacuo, to afford the title compounds.

| Ex. | IUPAC Name | LCMS MH+/MH− | HPLC RT/min (Method A, Mobile Phase II) |
|---|---|---|---|
| L24 | 3-[5-({[(carboxymethyl)amino]carbonyl}amino)-1H-benzimidazol-1-yl]-3-phenylpropanoic acid | 381 (−ve) | 1.63 |
| L25 | 3-(5-{[(benzylamino)carbonyl]amino}-1H-benzimidazol-1-yl)-3-phenylpropanoic acid | 415 | 3.70 |
| L26 | 3-{5-[(anilinocarbonyl)amino]-1H-benzimidazol-1-yl}-3-phenylpropanoic acid | 401 | 3.74 |
| L27 | 3-(5-{[(4-fluoroanilino)carbonyl]amino}-1H-benzimidazol-1-yl)-3-phenylpropanoic acid | 419 | 3.83 |
| L28 | 3-(5-{[(4-methoxyanilino)carbonyl]amino}-1H-benzimidazol-1-yl)-3-phenylpropanoic acid | 431 | 3.69 |
| L29 | 3-[5-({[4-(methylsulfanyl)anilino]carbonyl}amino)-1H-benzimidazol-1-yl]-3-phenylpropanoic acid | 447 | 4.04 |
| L30 | 3-(5-{[(4-nitroanilino)carbonyl]amino}-1H-benzimidazol-1-yl)-3-phenylpropanoic acid | 446 | 3.96 |
| L31 | 3-phenyl-3-[5-({[4-(trifluoromethyl)anilino]carbonyl}amino)-1H-benzimidazol-1-yl]propanoic acid | 469 | 4.36 |
| L32 | 3-(5-{[(3,4-dimethylanilino)carbonyl]amino}-1H-benzimidazol-1-yl)-3-phenylpropanoic acid | 429 | 4.13 |
| L33 | 3-[5-({[4-(benzyloxy)anilino]carbonyl}amino)-1H-benzimidazol-1-yl]-3-phenylpropanoic acid | 507 | 4.45 |
| L34 | 3-[5-({[(2,6-dichloro-4-pyridinyl)amino]carbonyl}amino)-1H-benzimidazol-1-yl]-3-phenylpropanoic acid | 470 | 4.01 |

| Ex. | IUPAC Name | LCMS MH+/MH- | HPLC RT/min (Method A, Mobile Phase II) |
|---|---|---|---|
| L35 | 3-(5-{[(cyclohexylamino)carbonyl]amino}-1H-benzimidazol-1-yl)-3-phenylpropanoic acid | 407 | 3.80 |
| L36 | 3-phenyl-3-{5-[({[2-(2-thienyl)ethyl]amino}carbonyl)amino]-1H-benzimidazol-1-yl}propanoic acid | 435 | 3.77 |

Generic Procedure for Amide Synthesis

To a solution of the appropriate carboxylic acid in NMP (60 μL, 20 μmol) was added N,N-diisopropylethylamine in NMP (36 μL, 20 μmol) and HATU in NMP (36 μL, 12 μmol). A solution of either ethyl 3-(5-amino-1H-benzimidazol-1-yl)-3-phenylpropanoate or ethyl 3-(6-amino-1H-benzimidazol-1-yl)-3-phenylpropanoate in NMP (30 μL, 10 μmol) was then added, and the resulting solution agitated for 90 hours. The solution was evaporated in vacuo, and the residue taken up in acetonitrile (120 μL). Hydrochloric acid (180 μL of a 5N solution) was added, and the solution agitated for a further 72 hours. The solution was evaporated in vacuo to afford the title compounds.

(* denotes isomers formed)

| Ex. | IUPAC Name | LCMS MH+/MH- | HPLC RT/min | LCMS Method | Mobile Phase |
|---|---|---|---|---|---|
| L37 | 3-phenyl-3-{5-[(2-quinolinylcarbonyl)amino]-1H-benzimidazol-1-yl}propanoic acid | 437 | 2.29 | B | II |
| L38 | 3-{5-[(3-isoquinolinylcarbonyl)amino]-1H-benzimidazol-1-yl}-3-phenylpropanoic acid | 437 | 2.20 | B | II |
| L39 | 3-phenyl-3-{5-[(2-quinoxalinylcarbonyl)amino]-1H-benzimidazol-1-yl}propanoic acid | 438 | 2.07 | B | II |
| L40 | 3-{5-[(1-isoquinolinylcarbonyl)amino]-1H-benzimidazol-1-yl}-3-phenylpropanoic acid | 437 | 2.16 | B | II |
| L41 | 3-{5-[(2,3-dihydro-1H-indol-2-ylcarbonyl)amino]-1H-benzimidazol-1-yl}-3-phenylpropanoic acid | 427 | 2.08, 2.22* | B | II |
| L42 | 3-phenyl-3-{5-[(2-quinoxalinylamino)-1H-benzimidazol-1-yl}propanoic acid | 438 | 1.76 | B | II |
| L43 | 3-phenyl-3-{5-[(2-pyrazinylcarbonyl)amino]-1H-benzimidazol-1-yl}propanoic acid | 388 | 1.66 | B | II |
| L44 | 3-phenyl-3-{5-[(3-pyridinylcarbonyl)amino]-1H-benzimidazol-1-yl}propanoic acid | 387 | 1.56 | B | II |
| L45 | 3-[5-(isonicotinoylamino)-1H-benzimidazol-1-yl]-3-phenylpropanoic acid | 387 | 1.59 | B | II |
| L46 | 3-(5-{[(2-hydroxy-3-pyridinyl)carbonyl]amino}-1H-benzimidazol-1-yl)-3-phenylpropanoic acid | 403 | 1.56 | B | II |
| L47 | 3-{5-[(1H-indol-2-ylcarbonyl)amino]-1H-benzimidazol-1-yl}-3-phenylpropanoic acid | 425 | 2.21 | B | II |
| L48 | 3-{5-[(1H-indol-3-ylcarbonyl)amino]-1H-benzimidazol-1-yl}-3-phenylpropanoic acid | 425 | 1.96 | B | II |
| L49 | 3-{5-[(3-nitrobenzoyl)amino]-1H-benzimidazol-1-yl}-3-phenylpropanoic acid | 431 | 2.05 | B | II |
| L50 | 3-phenyl-3-{5-[(3-pyridinylacetyl)amino]-1H-benzimidazol-1-yl}propanoic acid | 401 | 1.56 | B | II |
| L51 | 3-{5-[(1H-imidazol-4-ylacetyl)amino]-1H-benzimidazol-1-yl}-3-phenylpropanoic acid | 390 | 1.20, 1.27* | B | II |
| L52 | 3-(5-{[(2E)-3-(3-nitrophenyl)-2-propenoyl]amino}-1H-benzimidazol-1-yl)-3-phenylpropanoic acid | 457 | 2.24 | B | II |
| L53 | 3-(5-{[3-(1H-benzimidazol-2-yl)propanoyl]amino}-1H-benzimidazol-1-yl)-3-phenylpropanoic acid | 454 | 1.80 | B | II |
| L54 | 3-phenyl-3-(5-{[3-(3,4,5-trimethoxyphenyl)propanoyl]amino}-1H-benzimidazol-1-yl)propanoic acid | 505 | 1.97 | B | II |
| L55 | 3-{5-[(1H-indol-3-ylacetyl)amino]-1H-benzimidazol-1-yl}-3-phenylpropanoic acid | 439 | 2.00 | B | II |
| L56 | 3-(5-{[3-(1H-indol-3-yl)propanoyl]amino}-1H-benzimidazol-1-yl)-3-phenylpropanoic acid | 453 | 2.09 | B | II |
| L57 | 3-phenyl-3-{5-[(2-pyridinylcarbonyl)amino]-1H-benzimidazol-1-yl}propanoic acid | 387 | 1.87 | B | II |
| L58 | 3-(5-{[4-(1H-indol-3-yl)butanoyl]amino}-1H-benzimidazol-1-yl)-3-phenylpropanoic acid | 467 | 2.33 | B | II |

-continued

| Ex. | IUPAC Name | LCMS MH+/MH− | HPLC RT/min | LCMS Method | Mobile Phase |
|---|---|---|---|---|---|
| L59 | 3-(5-{[(5-methyl-2-pyrazinyl)carbonyl]amino}-1H-benzimidazol-1-yl)-3-phenylpropanoic acid | 402 | 1.74 | B | II |
| L60 | 3-(5-{[(5-methyl-2-phenyl-2H-1,2,3-triazol-4-yl)carbonyl]amino}-1H-benzimidazol-1-yl)-3-phenylpropanoic acid | 468 | 2.45 | B | II |
| L61 | 3-(5-{[(4-oxo-4,5,6,7-tetrahydro-1-benzofuran-3-yl)carbonyl]amino}-1H-benzimidazol-1-yl)-3-phenylpropanoic acid | 444 | 2.01 | B | II |
| L62 | 3-[5-({[2-(methylsulfanyl)-3-pyridinyl]carbonyl}amino)-1H-benzimidazol-1-yl]-3-phenylpropanoic acid | 433 | 1.85 | B | II |
| L63 | 3-[5-({[3-chloro-4-(isopropylsulfonyl)-2-thienyl]carbonyl}amino)-1H-benzimidazol-1-yl]-3-phenylpropanoic acid | 532 | 2.08 | B | II |
| L64 | 3-(5-{[(6-oxo-1,4,5,6-tetrahydro-3-pyridazinyl)carbonyl]amino}-1H-benzimidazol-1-yl)-3-phenylpropanoic acid | 406 | 1.50 | B | II |
| L65 | 3-[5-({[2-(2,3-dihydro-1,4-benzodioxin-2-yl)-1,3-thiazol-4-yl]carbonyl}amino)-1H-benzimidazol-1-yl]-3-phenylpropanoic acid | 528 | 2.44 | B | II |
| L66 | 3-[5-({(2E)-3-[3-nitro-4-(1-pyrrolidinyl)phenyl]-2-propenoyl}amino)-1H-benzimidazol-1-yl]-3-phenylpropanoic acid | 526 | 2.49 | B | II |
| L67 | 3-(5-{[3-(2-oxocyclododecyl)propanoyl]amino}-1H-benzimidazol-1-yl)-3-phenylpropanoic acid | 519 | 2.76 | B | II |
| L68 | 3-(5-{[(1-tert-butyl-3-methyl-1H-pyrazol-5-yl)carbonyl]amino}-1H-benzimidazol-1-yl)-3-phenylpropanoic acid | 446 | 2.00 | B | II |
| L69 | 3-(5-{[(2Z)-2-(3-oxo-2-benzofuran-1(3H)-ylidene)ethanoyl]amino}-1H-benzimidazol-1-yl)-3-phenylpropanoic acid | 454 | 1.99 | B | II |
| L70 | 3-{5-[(1-benzothien-2-ylcarbonyl)amino]-1H-benzimidazol-1-yl}-3-phenylpropanoic acid | 442 | 2.29 | B | II |
| L71 | 3-phenyl-3-(5-{[4-(trifluoromethoxy)benzoyl]amino}-1H-benzimidazol-1-yl)propanoic acid | 470 | 2.37 | B | II |
| L72 | 3-(5-{[(5-chloro-2-hydroxy-3-pyridinyl)carbonyl]amino}-1H-benzimidazol-1-yl)-3-phenylpropanoic acid | 437 | 1.74 | B | II |
| L73 | 3-(5-{[(2E)-4-oxo-4-(2,3,4,5,6-pentamethylphenyl)-2-butenoyl]amino}-1H-benzimidazol-1-yl)-3-phenylpropanoic acid | 510 | 2.62 | B | II |
| L74 | 3-(5-{[(6-bromo-2-oxo-2H-chromen-3-yl)carbonyl]amino}-1H-benzimidazol-1-yl)-3-phenylpropanoic acid | 534 | 2.47 | B | II |
| L75 | 3-phenyl-3-(5-{[4-(trifluoroacetyl)benzoyl]amino}-1H-benzimidazol-1-yl)propanoic acid | 480(−ve) | 1.89 | B | II |
| L76 | 3-[5-({[(4-chlorobenzoyl)amino]acetyl}amino)-1H-benzimidazol-1-yl]-3-phenylpropanoic acid | 477 | 1.99 | B | II |
| L77 | 3-(5-{[(2,7-dimethylpyrazolo[1,5-a]pyrimidin-6-yl)carbonyl]amino}-1H-benzimidazol-1-yl)-3-phenylpropanoic acid | 455 | 1.77 | B | II |
| L78 | 3-(5-{[(4-acetyl-5-methyl-2-oxo-2,3-dihydro-1H-pyrrol-3-yl)acetyl]amino}-1H-benzimidazol-1-yl)-3-phenylpropanoic acid | 462 | 1.71 | B | II |
| L79 | 3-phenyl-3-(5-{[(4-phenyl-1,2,3-thiadiazol-5-yl)carbonyl]amino}-1H-benzimidazol-1-yl)propanoic acid | 470 | 2.13 | B | II |
| L80 | 3-[5-({[1-(4-chlorobenzyl)-5-oxo-3-pyrrolidinyl]carbonyl}amino)-1H-benzimidazol-1-yl]-3-phenylpropanoic acid | 517 | 2.11 | B | II |
| L81 | 3-(5-{[({[(Z)-1-(4-chlorophenyl)ethylidene]amino}oxy)acetyl]amino}-1H-benzimidazol-1-yl)-3-phenylpropanoic acid | 491 | 2.47 | B | II |
| L82 | 3-phenyl-3-{5-[(1,2,3-thiadiazol-4-ylcarbonyl)amino]-1H-benzimidazol-1-yl}propanoic acid | 394 | 1.70 | B | II |
| L83 | 3-(5-{[(5-chloro-1-benzothien-3-yl)acetyl]amino}-1H-benzimidazol-1-yl)-3-phenylpropanoic acid | 490 | 2.44 | B | II |

-continued

| Ex. | IUPAC Name | LCMS MH+/MH− | HPLC RT/min | LCMS Method | Mobile Phase |
|---|---|---|---|---|---|
| L84 | 3-[5-({[5-chloro-2-(methylsulfanyl)-4-pyrimidinyl]carbonyl}amino)-1H-benzimidazol-1-yl]-3-phenylpropanoic acid | 468 | 2.12 | B | II |
| L85 | 3-[5-({[1-(2-furylmethyl)-5-oxo-3-pyrrolidinyl]carbonyl}amino)-1H-benzimidazol-1-yl]-3-phenylpropanoic acid | 473 | 1.78 | B | II |
| L86 | 3-(5-{[(3-tert-butyl-1-methyl-1H-pyrazol-5-yl)carbonyl]amino}-1H-benzimidazol-1-yl)-3-phenylpropanoic acid | 446 | 2.19 | B | II |
| L87 | 3-(5-{[(5-oxo-2-pyrrolidinyl)carbonyl]amino}-1H-benzimidazol-1-yl)-3-phenylpropanoic acid | 393 | 1.30 | B | II |
| L88 | 3-(5-{[(2,5-dimethoxyphenyl)acetyl]amino}-1H-benzimidazol-1-yl)-3-phenylpropanoic acid | 460 | 2.04 | B | II |
| L89 | 3-[5-({[2-(4-methylphenoxy)-3-pyridinyl]carbonyl}amino)-1H-benzimidazol-1-yl]-3-phenylpropanoic acid | 494 | 2.30 | B | II |
| L90 | 3-[5-(2-methyl-6-nitro-4-oxo-3(4H)-quinazolinyl)-1H-benzimidazol-1-yl]-3-phenylpropanoic acid | 470 | 2.03 | B | II |
| L91 | 3-(5-{[(3-methoxyphenyl)acetyl]amino}-1H-benzimidazol-1-yl)-3-phenylpropanoic acid | 430 | 2.00 | B | II |
| L92 | 3-(5-{[(4-methoxyphenyl)acetyl]amino}-1H-benzimidazol-1-yl)-3-phenylpropanoic acid | 430 | 1.99 | B | II |
| L93 | 3-(5-{[(2-methoxyphenyl)acetyl]amino}-1H-benzimidazol-1-yl)-3-phenylpropanoic acid | 430 | 2.04 | B | II |
| L94 | 3-(5-{[(2-phenoxy-3-pyridinyl)carbonyl]amino}-1H-benzimidazol-1-yl)-3-phenylpropanoic acid | 479 | 2.12 | B | II |
| L95 | 3-[5-({2-[4-(aminocarbonyl)phenoxy]-2-methylpropanoyl}amino)-1H-benzimidazol-1-yl]-3-phenylpropanoic acid | 487 | 1.77 | B | II |
| L96 | 3-phenyl-3-{5-[(1,2,3,4-tetrahydro-2-naphthalenylcarbonyl)amino]-1H-benzimidazol-1-yl}propanoic acid | 440 | 2.30 | B | II |
| L97 | 3-(5-{[(3,5-dimethyl-4-isoxazolyl)carbonyl]amino}-1H-benzimidazol-1-yl)-3-phenylpropanoic acid | 405 | 1.74 | B | II |
| L98 | 3-phenyl-3-{5-[(1H-pyrrol-2-ylcarbonyl)amino]-1H-benzimidazol-1-yl}propanoic acid | 375 | 1.79 | B | II |
| L99 | 3-[5-({[(2S)-5-oxopyrrolidinyl]carbonyl}amino)-1H-benzimidazol-1-yl]-3-phenylpropanoic acid | 393 | 1.30 | B | II |
| L100 | 3-phenyl-3-[5-({[(3S,4R,5S)-3,4,5-trihydroxy-1-cyclohexen-1-yl]carbonyl}amino)-1H-benzimidazol-1-yl]propanoic acid | 438 | 1.10 | B | II |
| L101 | 3-{5-[(cyclohexylacetyl)amino]-1H-benzimidazol-1-yl}-3-phenylpropanoic acid | 406 | 2.20 | B | II |
| L102 | 3-phenyl-3-(5-{[4-(1H-pyrrol-1-yl)benzoyl]amino}-1H-benzimidazol-1-yl)propanoic acid | 451 | 2.34 | B | II |
| L103 | 3-(5-{[(2,4-dihydroxy-5-pyrimidinyl)carbonyl]amino}-1H-benzimidazol-1-yl)-3-phenylpropanoic acid | 420 | 1.46 | B | II |
| L104 | 3-(5-{[2-(1,3-dioxo-1,3-dihydro-2H-isoindol-2-yl)propanoyl]amino}-1H-benzimidazol-1-yl)-3-phenylpropanoic acid | 483 | 2.02 | B | II |
| L105 | 3-(5-{[3-(1,3-dioxo-1,3-dihydro-2H-isoindol-2-yl)propanoyl]amino}-1H-benzimidazol-1-yl)-3-phenylpropanoic acid | 483 | 1.90 | B | II |
| L106 | 3-[5-({[1-(4-chlorophenyl)cyclopentyl]carbonyl}amino)-1H-benzimidazol-1-yl]-3-phenylpropanoic acid | 488 | 2.59 | B | II |
| L107 | 3-(5-{[(4-oxo-2-thioxo-1,3-thiazolidin-3-yl)acetyl]amino}-1H-benzimidazol-1-yl)-3-phenylpropanoic acid | 455 | 1.85 | B | II |
| L108 | 3-{5-[([1,1'-biphenyl]-4-ylacetyl)amino]-1H-benzimidazol-1-yl}-3-phenylpropanoic acid | 476 | 2.48 | B | II |
| L109 | 3-(5-{[(6-methoxy-3-oxo-2,3-dihydro-1H-inden-1-yl)acetyl]amino}-1H-benzimidazol-1-yl)-3-phenylpropanoic acid | 485 | 1.90 | B | II |
| L110 | 3-{5-[(9H-fluoren-9-ylacetyl)amino]-1H-benzimidazol-1-yl}-3-phenylpropanoic acid | 488 | 2.50 | B | II |

| Ex. | IUPAC Name | LCMS MH+/MH− | HPLC RT/min | LCMS Method | Mobile Phase |
|---|---|---|---|---|---|
| L111 | 3-(5-{[(9-oxo-9H-fluoren-1-yl)carbonyl]amino}-1H-benzimidazol-1-yl)-3-phenylpropanoic acid | 489 | 2.39 | B | II |
| L112 | 3-(5-{[(2-nitrophenyl)acetyl]amino}-1H-benzimidazol-1-yl)-3-phenylpropanoic acid | 445 | 2.00 | B | II |
| L113 | 3-(5-{[(4-nitrophenyl)acetyl]amino}-1H-benzimidazol-1-yl)-3-phenylpropanoic acid | 445 | 2.04 | B | II |
| L114 | 3-{5-[(9-anthrylcarbonyl)amino]-1H-benzimidazol-1-yl}-3-phenylpropanoic acid | 486 | 2.43 | B | II |
| L115 | 3-(5-{[(2-methylphenyl)acetyl]amino}-1H-benzimidazol-1-yl)-3-phenylpropanoic acid | 414 | 2.08 | B | II |
| L116 | 3-(5-{[(2,6-dioxo-1,2,3,6-tetrahydro-4-pyrimidinyl)carbonyl]amino}-1H-benzimidazol-1-yl)-3-phenylpropanoic acid | 421 | 2.50 | A | II |
| L117 | 3-(5-{[(4-methylphenyl)acetyl]amino}-1H-benzimidazol-1-yl)-3-phenylpropanoic acid | 414 | 3.68 | A | II |
| L118 | 3-{5-[(3-methylbenzoyl)amino]-1H-benzimidazol-1-yl}-3-phenylpropanoic acid | 400 | 3.63 | A | II |
| L119 | 3-phenyl-3-{5-[(4-vinylbenzoyl)amino]-1H-benzimidazol-1-yl}propanoic acid | 413 | 3.80 | A | II |
| L120 | 3-{5-[(4-methylbenzoyl)amino]-1H-benzimidazol-1-yl}-3-phenylpropanoic acid | 400 | 3.60 | A | II |
| L121 | 3-{5-[(2-methylbenzoyl)amino]-1H-benzimidazol-1-yl}-3-phenylpropanoic acid | 400 | 3.47 | A | II |
| L122 | 3-(5-{[(3-methylphenyl)acetyl]amino}-1H-benzimidazol-1-yl)-3-phenylpropanoic acid | 414 | 3.70 | A | II |
| L123 | 3-(5-{[(3-nitrophenyl)acetyl]amino}-1H-benzimidazol-1-yl)-3-phenylpropanoic acid | 445 | 3.58 | A | II |
| L124 | 3-{5-[(4-bromobenzoyl)amino]-1H-benzimidazol-1-yl}-3-phenylpropanoic acid | 464 | 3.81 | A | II |
| L125 | 3-phenyl-3-{5-[(9H-xanthen-9-ylcarbonyl)amino]-1H-benzimidazol-1-yl}propanoic acid | 490 | 4.10 | A | II |
| L126 | 3-{5-[(2-phenoxypropanoyl)amino]-1H-benzimidazol-1-yl}-3-phenylpropanoic acid | 430 | 3.69 | A | II |
| L127 | 3-(5-{[(1,3-dioxo-1,3-dihydro-2H-isoindol-2-yl)acetyl]amino}-1H-benzimidazol-1-yl)-3-phenylpropanoic acid | 469 | 3.28 | A | II |
| L128 | 3-{5-[(1,3-benzodioxol-5-ylcarbonyl)amino]-1H-benzimidazol-1-yl}-3-phenylpropanoic acid | 430 | 3.37 | A | II |
| L129 | 3-phenyl-3-{5-[(phenylacetyl)amino]-1H-benzimidazol-1-yl}propanoic acid | 400 | 3.42 | A | II |
| L130 | 3-{5-[(bicyclo[2.2.1]hept-5-en-2-ylcarbonyl)amino]-1H-benzimidazol-1-yl}-3-phenylpropanoic acid | 402 | 3.63 | A | II |
| L131 | 3-(5-{[hydroxy(phenyl)acetyl]amino}-1H-benzimidazol-1-yl)-3-phenylpropanoic acid | 416 | 3.12 | A | II |
| L132 | 3-(5-{[(2-naphthyloxy)acetyl]amino}-1H-benzimidazol-1-yl)-3-phenylpropanoic acid | 466 | 4.08 | A | II |
| L133 | 3-phenyl-3-(5-{[(1-phenylcyclopentyl)carbonyl]amino}-1H-benzimidazol-1-yl)propanoic acid | 454 | 4.04 | A | II |
| L134 | 3-phenyl-3-{5-[(2-sulfanylbenzoyl)amino]-1H-benzimidazol-1-yl}propanoic acid | 416 | 3.53 | A | II |
| L135 | 3-(5-{[cyclopentyl(phenyl)acetyl]amino}-1H-benzimidazol-1-yl)-3-phenylpropanoic acid | 468 | 4.25 | A | II |
| L136 | 3-{5-[(4-tert-butylbenzoyl)amino]-1H-benzimidazol-1-yl}-3-phenylpropanoic acid | 442 | 4.25 | A | II |
| L137 | 3-{5-[(1-adamantylcarbonyl)amino]-1H-benzimidazol-1-yl}-3-phenylpropanoic acid | 444 | 4.09 | A | II |
| L138 | 3-{5-[(4-methoxybenzoyl)amino]-1H-benzimidazol-1-yl}-3-phenylpropanoic acid | 416 | 3.42 | A | II |
| L139 | 3-{5-[(4-cyclohexylbenzoyl)amino]-1H-benzimidazol-1-yl}-3-phenylpropanoic acid | 468 | 4.65 | A | II |
| L140 | 3-[5-(1-naphthoylamino)-1H-benzimidazol-1-yl]-3-phenylpropanoic acid | 437 | 3.73 | A | II |
| L141 | 3-[5-(benzoylamino)-1H-benzimidazol-1-yl]-3-phenylpropanoic acid | 387 | 3.31 | A | II |
| L142 | 3-(5-{[(2E)-3-(4-bromophenyl)-2-propenoyl]amino}-1H-benzimidazol-1-yl)-3-phenylpropanoic acid | 492 | 4.09 | A | II |
| L143 | 3-{5-[(3-bromo-4-methoxybenzoyl)amino]-1H-benzimidazol-1-yl}-3-phenylpropanoic acid | 496 | 3.79 | A | II |
| L144 | 3-{5-[(4-butylbenzoyl)amino]-1H-benzimidazol-1-yl}-3-phenylpropanoic acid | 443 | 4.32 | A | II |

| Ex. | IUPAC Name | LCMS MH+/MH− | HPLC RT/min | LCMS Method | Mobile Phase |
|---|---|---|---|---|---|
| L145 | 3-(5-{[4-(dimethylamino)benzoyl]amino}-1H-benzimidazol-1-yl)-3-phenylpropanoic acid | 429 | 3.58 | A | II |
| L146 | 3-(5-{[(4-bromo-1-ethyl-3-methyl-1H-pyrazol-5-yl)carbonyl]amino}-1H-benzimidazol-1-yl)-3-phenylpropanoic acid | 498 | 3.58 | A | II |
| L147 | 3-{5-[(4-nitrobenzoyl)amino]-1H-benzimidazol-1-yl}-3-phenylpropanoic acid | 431 | 3.66 | A | II |
| L148 | 3-(5-{[(2-cyclopropyl-4-quinolinyl)carbonyl]amino}-1H-benzimidazol-1-yl)-3-phenylpropanoic acid | 477 | 3.72 | A | II |
| L149 | 3-phenyl-3-[5-({[2-(2-thienyl)-4-quinolinyl]carbonyl}amino)-1H-benzimidazol-1-yl]propanoic acid | 519 | 4.15 | A | II |
| L150 | 3-{5-[(3,5-dinitrobenzoyl)amino]-1H-benzimidazol-1-yl}-3-phenylpropanoic acid | 476 | 3.80 | A | II |
| L151 | 3-phenyl-3-{5-[(3-phenyl-2-propynoyl)amino]-1H-benzimidazol-1-yl}propanoic acid | 410 | 3.74 | A | II |
| L152 | 3-{5-[(4-fluoro-1-naphthoyl)amino]-1H-benzimidazol-1-yl}-3-phenylpropanoic acid | 454 | 3.86 | A | II |
| L153 | 3-(5-{[(7-methyl-2-phenyl-4-quinolinyl)carbonyl]amino}-1H-benzimidazol-1-yl)-3-phenylpropanoic acid | 527 | 4.33 | A | II |
| L154 | 3-(5-{[(5-bromo-4-methoxy-3-thienyl)carbonyl]amino}-1H-benzimidazol-1-yl)-3-phenylpropanoic acid | 500 | 3.96 | A | II |
| L155 | 3-{5-[(4-[1,1'-biphenyl]-4-yl-4-oxobutanoyl)amino]-1H-benzimidazol-1-yl}-3-phenylpropanoic acid | 518 | 4.25 | A | II |
| L156 | 3-{5-[(1-cyclohexen-1-ylcarbonyl)amino]-1H-benzimidazol-1-yl}-3-phenylpropanoic acid | 390 | 3.50 | A | II |
| L157 | 3-(5-{[(4-bromophenyl)acetyl]amino}-1H-benzimidazol-1-yl)-3-phenylpropanoic acid | 480 | 3.83 | A | II |
| L158 | 3-(5-{[2-(methylsulfanyl)benzoyl]amino}-1H-benzimidazol-1-yl)-3-phenylpropanoic acid | 432 | 3.48 | A | II |
| L159 | 3-(5-{[(2E)-3-(5-bromo-2-ethoxyphenyl)-2-propenoyl]amino}-1H-benzimidazol-1-yl)-3-phenylpropanoic acid | 536 | 4.31 | A | II |
| L160 | 3-(5-{[4-(methylsulfonyl)benzoyl]amino}-1H-benzimidazol-1-yl)-3-phenylpropanoic acid | 465 | 3.17 | A | II |
| L161 | 3-(5-{[2-nitro-4-(trifluoromethyl)benzoyl]amino}-1H-benzimidazol-1-yl)-3-phenylpropanoic acid | 499 | 3.86 | A | II |
| L162 | 3-{5-[([1,1'-biphenyl]-4-ylcarbonyl)amino]-1H-benzimidazol-1-yl}-3-phenylpropanoic acid | 462 | 4.17 | A | II |
| L163 | 3-{5-[(4-benzoylbenzoyl)amino]-1H-benzimidazol-1-yl}-3-phenylpropanoic acid | 490 | 3.94 | A | II |
| L164 | 3-phenyl-3-(5-{[4-(trifluoromethyl)benzoyl]amino}-1H-benzimidazol-1-yl)propanoic acid | 454 | 3.93 | A | II |
| L165 | 3-{5-[(4-acetylbenzoyl)amino]-1H-benzimidazol-1-yl}-3-phenylpropanoic acid | 428 | 3.27 | A | II |
| L166 | 3-{5-[(4-cyanobenzoyl)amino]-1H-benzimidazol-1-yl}-3-phenylpropanoic acid | 411 | 3.38 | A | II |
| L167 | 3-(5-{[2,4-bis(trifluoromethyl)benzoyl]amino}-1H-benzimidazol-1-yl)-3-phenylpropanoic acid | 522 | 4.08 | A | II |
| L168 | 3-phenyl-3-(5-{[3-(trifluoromethyl)benzoyl]amino}-1H-benzimidazol-1-yl)propanoic acid | 454 | 3.91 | A | II |
| L169 | 3-{5-[(3-cyanobenzoyl)amino]-1H-benzimidazol-1-yl}-3-phenylpropanoic acid | 412 | 3.37 | A | II |
| L170 | 3-{5-[(1H-benzimidazol-5-ylcarbonyl)amino]-1H-benzimidazol-1-yl}-3-phenylpropanoic acid | 426 | 2.89 | A | II |
| L171 | 3-{5-[(diphenylacetyl)amino]-1H-benzimidazol-1-yl}-3-phenylpropanoic acid | 477 | 4.10 | A | II |
| L172 | 3-{5-[(2-hydroxybenzoyl)amino]-1H-benzimidazol-1-yl}-3-phenylpropanoic acid | 402 | 3.57 | A | II |
| L173 | 3-{5-[(4-ethylbenzoyl)amino]-1H-benzimidazol-1-yl}-3-phenylpropanoic acid | 414 | 3.84 | A | II |
| L174 | 3-{5-[(3-bromo-2,6-dimethoxybenzoyl)amino]-1H-benzimidazol-1-yl}-3-phenylpropanoic acid | 526 | 3.68 | A | II |

| Ex. | IUPAC Name | LCMS MH+/MH− | HPLC RT/min | LCMS Method | Mobile Phase |
|---|---|---|---|---|---|
| L175 | 3-{5-[(4-bromo-2,3,5,6-tetrafluorobenzoyl)amino]-1H-benzimidazol-1-yl}-3-phenylpropanoic acid | 538 | 4.01 | A | II |
| L176 | 3-{5-[(5-bromo-2-furoyl)amino]-1H-benzimidazol-1-yl}-3-phenylpropanoic acid | 454 | 3.49 | A | II |
| L177 | 3-{5-[(3-iodobenzoyl)amino]-1H-benzimidazol-1-yl}-3-phenylpropanoic acid | 512 | 3.90 | A | II |
| L178 | 3-{5-[(2-formylbenzoyl)amino]-1H-benzimidazol-1-yl}-3-phenylpropanoic acid | 415 | 3.10 | A | II |
| L179 | 3-{5-[(2-bromobenzoyl)amino]-1H-benzimidazol-1-yl}-3-phenylpropanoic acid | 464 | 3.45 | A | II |
| L180 | 3-{5-[(3-bromobenzoyl)amino]-1H-benzimidazol-1-yl}-3-phenylpropanoic acid | 466 | 3.80 | A | II |
| L181 | 3-(5-{[(5-bromo-3-pyridinyl)carbonyl]amino}-1H-benzimidazol-1-yl)-3-phenylpropanoic acid | 465 | 3.31 | A | II |
| L182 | 3-(5-{[(5-bromo-2-thienyl)carbonyl]amino}-1H-benzimidazol-1-yl)-3-phenylpropanoic acid | 472 | 3.82 | A | II |
| L183 | 3-{5-[(2-bromo-5-methoxybenzoyl)amino]-1H-benzimidazol-1-yl}-3-phenylpropanoic acid | 494 | 3.58 | A | II |
| L184 | 3-{5-[(4-bromo-2-methylbenzoyl)amino]-1H-benzimidazol-1-yl}-3-phenylpropanoic acid | 478 | 3.87 | A | II |
| L185 | 3-{5-[(4-bromo-2-chlorobenzoyl)amino]-1H-benzimidazol-1-yl}-3-phenylpropanoic acid | 500 | 3.90 | A | II |
| L186 | 3-(5-{[(2E)-3-(3-bromo-4-fluorophenyl)-2-propenoyl]amino}-1H-benzimidazol-1-yl)-3-phenylpropanoic acid | 508 | 4.12 | A | II |
| L187 | 3-(5-{[(2E)-3-(6-bromo-1,3-benzodioxol-5-yl)-2-propenoyl]amino}-1H-benzimidazol-1-yl)-3-phenylpropanoic acid | 534 | 3.96 | A | II |
| L188 | 3-phenyl-3-[5-({[2-(phenylsulfanyl)-3-pyridinyl]carbonyl}amino)-1H-benzimidazol-1-yl]propanoic acid | 495 | 3.63 | A | II |
| L189 | 3-{5-[(2-hydroxy-5-nitrobenzoyl)amino]-1H-benzimidazol-1-yl}-3-phenylpropanoic acid | 447 | 2.88 | A | II |
| L190 | 3-{5-[(2-hydroxy-3-methoxybenzoyl)amino]-1H-benzimidazol-1-yl}-3-phenylpropanoic acid | 433 | 3.40 | A | II |
| L191 | 3-(5-{[(4-hydroxy-3-methoxyphenyl)acetyl]amino}-1H-benzimidazol-1-yl)-3-phenylpropanoic acid | 446 | 2.88 | A | II |
| L192 | 3-{5-[(2,5-dihydroxybenzoyl)amino]-1H-benzimidazol-1-yl}-3-phenylpropanoic acid | 419 | 3.09 | A | II |
| L193 | 3-{5-[(2-hydroxy-3-methylbenzoyl)amino]-1H-benzimidazol-1-yl}-3-phenylpropanoic acid | 416 | 3.96 | A | II |
| L194 | 3-{5-[(3-hydroxy-4-methylbenzoyl)amino]-1H-benzimidazol-1-yl}-3-phenylpropanoic acid | 416 | 33.8 | A | II |
| L195 | 3-(5-{[(3-hydroxy-4-methoxyphenyl)acetyl]amino}-1H-benzimidazol-1-yl)-3-phenylpropanoic acid | 447 | 3.10 | A | II |
| L196 | 3-(5-{[(4,7-dimethylpyrazolo[5,1-c][1,2,4]triazin-3-yl)carbonyl]amino}-1H-benzimidazol-1-yl)-3-phenylpropanoic acid | 456 | 3.44 | A | II |
| L197 | 3-(5-{[3-(2,4-dihydroxyphenyl)propanoyl]amino}-1H-benzimidazol-1-yl)-3-phenylpropanoic acid | 416 | 3.39 | A | II |
| L198 | 3-(5-{[(3,5-ditert-butyl-4-hydroxyphenyl)acetyl]amino}-1H-benzimidazol-1-yl)-3-phenylpropanoic acid | 528 | 4.47 | A | II |
| L199 | 3-(5-{[(6-hydroxy-2,5,7,8-tetramethyl-3,4-dihydro-2H-chromen-2-yl)carbonyl]amino}-1H-benzimidazol-1-yl)-3-phenylpropanoic acid | 514 | 3.90 | A | II |
| L200 | 3-{5-[(3,5-dichloro-2-hydroxybenzoyl)amino]-1H-benzimidazol-1-yl}-3-phenylpropanoic acid | 470 | 3.49 | A | II |
| L201 | 3-phenyl-3-{5-[(2,4,6-trihydroxybenzoyl)amino]-1H-benzimidazol-1-yl}propanoic acid | 434 | 3.01 | A | II |
| L202 | 3-{5-[(2-hydroxybenzoyl)amino]-1H-benzimidazol-1-yl}-3-phenylpropanoic acid | 402 | 3.56 | A | II |

-continued

| Ex. | IUPAC Name | LCMS MH+/MH− | HPLC RT/min | LCMS Method | Mobile Phase |
|---|---|---|---|---|---|
| L203 | 3-phenyl-3-{5-[(2,3,5-trichloro-6-hydroxybenzoyl)amino]-1H-benzimidazol-1-yl}propanoic acid | 504 | 3.55 | A | II |
| L204 | 3-{5-[(5-chloro-2-hydroxybenzoyl)amino]-1H-benzimidazol-1-yl}-3-phenylpropanoic acid | 437 | 3.85 | A | II |
| L205 | 3-{5-[(5-bromo-2-hydroxybenzoyl)amino]-1H-benzimidazol-1-yl}-3-phenylpropanoic acid | 480 (−ve) | 3.92 | A | II |
| L206 | 3-{5-[(2-hydroxy-4-methylbenzoyl)amino]-1H-benzimidazol-1-yl}-3-phenylpropanoic acid | 416 | 3.80 | A | II |
| L207 | 3-(5-{[(3,4-dihydroxyphenyl)acetyl]amino}-1H-benzimidazol-1-yl)-3-phenylpropanoic acid | 433 | 2.60 | A | II |
| L208 | 3-{5-[(2-fluoro-6-iodobenzoyl)amino]-1H-benzimidazol-1-yl}-3-phenylpropanoic acid | 530 | 3.57 | A | II |
| L209 | 3-phenyl-3-{6-[(2-quinolinylcarbonyl)amino]-1H-benzimidazol-1-yl}propanoic acid | 437 | 2.39 | B | I |
| L210 | 3-{6-[(3-isoquinolinylcarbonyl)amino]-1H-benzimidazol-1-yl}-3-phenylpropanoic acid | 437 | 2.31 | B | I |
| L211 | 3-phenyl-3-{6-[(2-quinoxalinylcarbonyl)amino]-1H-benzimidazol-1-yl}propanoic acid | 438 | 2.15 | B | I |
| L212 | 3-{6-[(1-isoquinolinylcarbonyl)amino]-1H-benzimidazol-1-yl}-3-phenylpropanoic acid | 438 | 2.29 | B | I |
| L213 | 3-{6-[(2,3-dihydro-1H-indol-2-ylcarbonyl)amino]-1H-benzimidazol-1-yl}-3-phenylpropanoic acid | 426 | 2.16 | B | I |
| L214 | 3-phenyl-3-{6-[(2-quinoxalinylcarbonyl)amino]-1H-benzimidazol-1-yl}propanoic acid | 438 | 1.75 | B | I |
| L215 | 3-phenyl-3-{6-[(2-pyrazinylcarbonyl)amino]-1H-benzimidazol-1-yl}propanoic acid | 388 | 1.62 | B | I |
| L216 | 3-phenyl-3-{6-[(3-pyridinylcarbonyl)amino]-1H-benzimidazol-1-yl}propanoic acid | 387 | 1.42 | B | I |
| L217 | 3-[6-(isonicotinoylamino)-1H-benzimidazol-1-yl]-3-phenylpropanoic acid | 387 | 1.37 | B | I |
| L218 | 3-(6-{[(2-hydroxy-3-pyridinyl)carbonyl]amino}-1H-benzimidazol-1-yl)-3-phenylpropanoic acid | 403 | 1.56 | B | I |
| L219 | 3-{6-[(1H-indol-2-ylcarbonyl)amino]-1H-benzimidazol-1-yl}-3-phenylpropanoic acid | 425 | 2.23 | B | I |
| L220 | 3-{6-[(1H-indol-3-ylcarbonyl)amino]-1H-benzimidazol-1-yl}-3-phenylpropanoic acid | 425 | 1.97 | B | I |
| L221 | 3-{6-[(3-nitrobenzoyl)amino]-1H-benzimidazol-1-yl}-3-phenylpropanoic acid | 431 | 2.14 | B | I |
| L222 | 3-(6-{[(2E)-3-(1H-indol-3-yl)-2-propenoyl]amino}-1H-benzimidazol-1-yl)-3-phenylpropanoic acid | 451 | 2.35 | B | I |
| L223 | 3-(6-{[(2E)-3-(3-nitrophenyl)-2-propenoyl]amino}-1H-benzimidazol-1-yl)-3-phenylpropanoic acid | 457 | 2.23 | B | I |
| L224 | 3-(6-{[3-(1H-benzimidazol-2-yl)propanoyl]amino}-1H-benzimidazol-1-yl)-3-phenylpropanoic acid | 454 | 1.33 | B | I |
| L225 | 3-phenyl-3-(6-{[3-(3,4,5-trimethoxyphenyl)propanoyl]amino}-1H-benzimidazol-1-yl)propanoic acid | 504 | 1.92 | B | I |
| L226 | 3-{6-[(1H-indol-3-ylacetyl)amino]-1H-benzimidazol-1-yl}-3-phenylpropanoic acid | 439 | 2.03 | B | I |
| L227 | 3-(6-{[3-(1H-indol-3-yl)propanoyl]amino}-1H-benzimidazol-1-yl)-3-phenylpropanoic acid | 453 | 2.15 | B | I |
| L228 | 3-phenyl-3-{6-[(2-pyridinylcarbonyl)amino]-1H-benzimidazol-1-yl}propanoic acid | 387 | 1.89 | B | I |
| L229 | 3-(6-{[(5-methyl-2-pyrazinyl)carbonyl]amino}-1H-benzimidazol-1-yl)-3-phenylpropanoic acid | 402 | 1.75 | B | I |
| L230 | 3-(6-{[(5-methyl-2-phenyl-2H-1,2,3-triazol-4-yl)carbonyl]amino}-1H-benzimidazol-1-yl)-3-phenylpropanoic acid | 467 | 2.63 | B | I |
| L231 | 3-(6-{[(4-oxo-4,5,6,7-tetrahydro-1-benzofuran-3-yl)carbonyl]amino}-1H-benzimidazol-1-yl)-3-phenylpropanoic acid | 444 | 2.05 | B | I |

-continued

| Ex. | IUPAC Name | LCMS MH+/MH− | HPLC RT/min | LCMS Method | Mobile Phase |
|---|---|---|---|---|---|
| L232 | 3-[6-({[2-(methylsulfanyl)-3-pyridinyl]carbonyl}amino)-1H-benzimidazol-1-yl]-3-phenylpropanoic acid | 433 | 1.90 | B | I |
| L233 | 3-[6-({[3-chloro-4-(isopropylsulfonyl)-2-thienyl]carbonyl}amino)-1H-benzimidazol-1-yl]-3-phenylpropanoic acid | 533 | 2.13 | B | I |
| L234 | 3-(6-{[(6-oxo-1,4,5,6-tetrahydro-3-pyridazinyl)carbonyl]amino}-1H-benzimidazol-1-yl)-3-phenylpropanoic acid | 406 | 1.46 | B | I |
| L235 | 3-[6-({[2-(2,3-dihydro-1,4-benzodioxin-2-yl)-1,3-thiazol-4-yl]carbonyl}amino)-1H-benzimidazol-1-yl]-3-phenylpropanoic acid | 527 | 2.45, 2.61* | B | I |
| L236 | 3-[6-({(2E)-3-[3-nitro-4-(1-pyrrolidinyl)phenyl]-2-propenoyl}amino)-1H-benzimidazol-1-yl]-3-phenylpropanoic acid | 526 | 2.59, 2.73* | B | I |
| L237 | 3-(6-{[3-(2-oxocyclododecyl)propanoyl]amino}-1H-benzimidazol-1-yl)-3-phenylpropanoic acid | 519 | 2.88 | B | I |
| L238 | 3-(6-{[(1-tert-butyl-3-methyl-1H-pyrazol-5-yl)carbonyl]amino}-1H-benzimidazol-1-yl)-3-phenylpropanoic acid | 446 | 2.12 | B | I |
| L239 | 3-(6-{[(2Z)-2-(3-oxo-2-benzofuran-1(3H)-ylidene)ethanoyl]amino}-1H-benzimidazol-1-yl)-3-phenylpropanoic acid | 454 | 2.00 | B | I |
| L240 | 3-{6-[(1-benzothien-2-ylcarbonyl)amino]-1H-benzimidazol-1-yl}-3-phenylpropanoic acid | 442 | 2.45 | B | I |
| L241 | 3-phenyl-3-(6-{[4-(trifluoromethoxy)benzoyl]amino}-1H-benzimidazol-1-yl)propanoic acid | 470 | 2.51 | B | I |
| L242 | 3-(6-{[(5-chloro-2-hydroxy-3-pyridinyl)carbonyl]amino}-1H-benzimidazol-1-yl)-3-phenylpropanoic acid | 437 | 1.87 | B | I |
| L243 | 3-(6-{[(2E)-4-oxo-4-(2,3,4,5,6-pentamethylphenyl)-2-butenoyl]amino}-1H-benzimidazol-1-yl)-3-phenylpropanoic acid | 511 | 2.80 | B | I |
| L244 | 3-(6-{[(6-bromo-2-oxo-2H-chromen-3-yl)carbonyl]amino}-1H-benzimidazol-1-yl)-3-phenylpropanoic acid | 534 | 2.65 | B | I |
| L245 | 3-phenyl-3-(6-{[4-(trifluoroacetyl)benzoyl]amino}-1H-benzimidazol-1-yl)propanoic acid | 482 | 1.93 | B | I |
| L246 | 3-[6-({[(4-chlorobenzoyl)amino]acetyl}amino)-1H-benzimidazol-1-yl]-3-phenylpropanoic acid | 477 | 2.07 | B | I |
| L247 | 3-(6-{[(2,7-dimethylpyrazolo[1,5-a]pyrimidin-6-yl)carbonyl]amino}-1H-benzimidazol-1-yl)-3-phenylpropanoic acid | 455 | 1.82 | B | I |
| L258 | 3-(6-{[2-(4-aminophenoxy)-2-methylpropanoyl]amino}-1H-benzimidazol-1-yl)-3-phenylpropanoic acid | 459 | 2.58 | B | I |
| L249 | 3-(6-{[(4-acetyl-5-methyl-2-oxo-2,3-dihydro-1H-pyrrol-3-yl)acetyl]amino}-1H-benzimidazol-1-yl)-3-phenylpropanoic acid | 462 | 1.81 | B | I |
| L250 | 3-phenyl-3-(6-{[(4-phenyl-1,2,3-thiadiazol-5-yl)carbonyl]amino}-1H-benzimidazol-1-yl)propanoic acid | 470 | 2.26 | B | I |
| L251 | 3-[6-({[1-(4-chlorobenzyl)-5-oxo-3-pyrrolidinyl]carbonyl}amino)-1H-benzimidazol-1-yl]-3-phenylpropanoic acid | 517 | 2.09, 2.14* | B | I |
| L252 | 3-(6-{[({[(Z)-1-(4-chlorophenyl)ethylidene]amino}oxy)acetyl]amino}-1H-benzimidazol-1-yl)-3-phenylpropanoic acid | 491 | 2.61, 2.73* | B | I |
| L253 | 3-phenyl-3-{6-[(1,2,3-thiadiazol-4-ylcarbonyl)amino]-1H-benzimidazol-1-yl}propanoic acid | 394 | 1.71 | B | I |
| L254 | 3-(6-{[(5-chloro-1-benzothien-3-yl)acetyl]amino}-1H-benzimidazol-1-yl)-3-phenylpropanoic acid | 490 | 2.53 | B | I |
| L255 | 3-[6-({[5-chloro-2-(methylsulfanyl)-4-pyrimidinyl]carbonyl}amino)-1H-benzimidazol-1-yl]-3-phenylpropanoic acid | 468 | 2.29 | B | I |
| L256 | 3-(6-({[1-(2-furylmethyl)-5-oxo-3-pyrrolidinyl]carbonyl}amino)-1H-benzimidazol-1-yl]-3-phenylpropanoic acid | 473 | 1.78, 1.81* | B | I |

-continued

| Ex. | IUPAC Name | LCMS MH+/MH- | HPLC RT/min | LCMS Method | Mobile Phase |
|---|---|---|---|---|---|
| L257 | 3-(6-{[(3-tert-butyl-1-methyl-1H-pyrazol-5-yl)carbonyl]amino}-1H-benzimidazol-1-yl)-3-phenylpropanoic acid | 446 | 2.33 | B | I |
| L258 | 3-(6-{[(5-oxo-2-pyrrolidinyl)carbonyl]amino}-1H-benzimidazol-1-yl)-3-phenylpropanoic acid | 393 | 1.31 | B | I |
| L259 | 3-(6-{[(2,5-dimethoxyphenyl)acetyl]amino}-1H-benzimidazol-1-yl)-3-phenylpropanoic acid | 460 | 2.05 | B | I |
| L260 | 3-[6-({[2-(4-methylphenoxy)-3-pyridinyl]carbonyl}amino)-1H-benzimidazol-1-yl]-3-phenylpropanoic acid | 494 | 2.40 | B | I |
| L261 | 3-[6-(2-methyl-6-nitro-4-oxo-3(4H)-quinazolinyl)-1H-benzimidazol-1-yl]-3-phenylpropanoic acid | 470 | 2.32 | B | I |
| L262 | 3-(6-{[(3-methoxyphenyl)acetyl]amino}-1H-benzimidazol-1-yl)-3-phenylpropanoic acid | 430 | 2.01 | B | I |
| L263 | 3-(6-{[(4-methoxyphenyl)acetyl]amino}-1H-benzimidazol-1-yl)-3-phenylpropanoic acid | 430 | 1.98 | B | I |
| L264 | 3-(6-{[(2-methoxyphenyl)acetyl]amino}-1H-benzimidazol-1-yl)-3-phenylpropanoic acid | 430 | 2.04 | B | I |
| L265 | 3-(6-{[(2-phenoxy-3-pyridinyl)carbonyl]amino}-1H-benzimidazol-1-yl)-3-phenylpropanoic acid | 479 | 2.24 | B | I |
| L266 | 3-[6-({2-[4-(aminocarbonyl)phenoxy]-2-methylpropanoyl}amino)-1H-benzimidazol-1-yl]-3-phenylpropanoic acid | 488 | 1.81 | B | I |
| L267 | 3-phenyl-3-{6-[(1,2,3,4-tetrahydro-2-naphthalenylcarbonyl)amino]-1H-benzimidazol-1-yl}propanoic acid | 440 | 2.41, 2.55* | B | I |
| L268 | 3-(6-{[(3,5-dimethyl-4-isoxazolyl)carbonyl]amino}-1H-benzimidazol-1-yl)-3-phenylpropanoic acid | 405 | 1.78 | B | I |
| L269 | 3-phenyl-3-{6-[(1H-pyrrol-2-ylcarbonyl)amino]-1H-benzimidazol-1-yl}propanoic acid | 375 | 1.78 | B | I |
| L270 | 3-[6-({[(2S)-5-oxopyrrolidinyl]carbonyl}amino)-1H-benzimidazol-1-yl]-3-phenylpropanoic acid | 392 | 2.46 | B | I |
| L271 | 3-phenyl-3-[6-({[(3S,4R,5S)-3,4,5-trihydroxy-1-cyclohexen-1-yl]carbonyl}amino)-1H-benzimidazol-1-yl]propanoic acid | 438 | 0.93 | B | I |
| L272 | 3-{6-[(cyclohexylacetyl)amino]-1H-benzimidazol-1-yl}-3-phenylpropanoic acid | 406 | 2.31 | B | I |
| L273 | 3-phenyl-3-(6-{[4-(1H-pyrrol-1-yl)benzoyl]amino}-1H-benzimidazol-1-yl)propanoic acid | 451 | 2.49 | B | I |
| L274 | 3-(6-{[(2,4-dihydroxy-5-pyrimidinyl)carbonyl]amino}-1H-benzimidazol-1-yl)-3-phenylpropanoic acid | 420 | 1.41 | B | I |
| L275 | 3-(6-{[2-(1,3-dioxo-1,3-dihydro-2H-isoindol-2-yl)propanoyl]amino}-1H-benzimidazol-1-yl)-3-phenylpropanoic acid | 483 | 1.97, 2.10* | B | I |
| L276 | 3-(6-{[3-(1,3-dioxo-1,3-dihydro-2H-isoindol-2-yl)propanoyl]amino}-1H-benzimidazol-1-yl)-3-phenylpropanoic acid | 483 | 1.93 | B | I |
| L277 | 3-[6-({[1-(4-chlorophenyl)cyclopentyl]carbonyl}amino)-1H-benzimidazol-1-yl]-3-phenylpropanoic acid | 488 | 2.75 | B | I |
| L278 | 3-(6-{[(4-oxo-2-thioxo-1,3-thiazolidin-3-yl)acetyl]amino}-1H-benzimidazol-1-yl)-3-phenylpropanoic acid | 455 | 1.89 | B | I |
| L279 | 3-[6-({[(4S)-2,6-dioxohexahydro-4-pyrimidinyl]carbonyl}amino)-1H-benzimidazol-1-yl]-3-phenylpropanoic acid | 422 | 1.07 | B | I |
| L280 | 3-{6-[([1,1'-biphenyl]-4-ylacetyl)amino]-1H-benzimidazol-1-yl}-3-phenylpropanoic acid | 476 | 2.55 | B | I |
| L281 | 3-(6-{[(6-methoxy-3-oxo-2,3-dihydro-1H-inden-1-yl)acetyl]amino}-1H-benzimidazol-1-yl)-3-phenylpropanoic acid | 484 | 1.80, 1.92* | B | I |
| L282 | 3-{6-[(9H-fluoren-9-ylacetyl)amino]-1H-benzimidazol-1-yl}-3-phenylpropanoic acid | 488 | 2.59 | B | I |
| L283 | 3-(6-{[(9-oxo-9H-fluoren-1-yl)carbonyl]amino}-1H-benzimidazol-1-yl)-3-phenylpropanoic acid | 488 | 2.58 | B | I |

| Ex. | IUPAC Name | LCMS MH+/MH− | HPLC RT/min | LCMS Method | Mobile Phase |
|---|---|---|---|---|---|
| L284 | 3-(6-{[(2-nitrophenyl)acetyl]amino}-1H-benzimidazol-1-yl)-3-phenylpropanoic acid | 445 | 2.08 | B | I |
| L285 | 3-(6-{[(4-nitrophenyl)acetyl]amino}-1H-benzimidazol-1-yl)-3-phenylpropanoic acid | 446 | 1.99 | B | I |
| L286 | 3-{6-[(9-anthrylcarbonyl)amino]-1H-benzimidazol-1-yl}-3-phenylpropanoic acid | 486 | 2.56 | B | I |
| L287 | 3-(6-{[(2-methylphenyl)acetyl]amino}-1H-benzimidazol-1-yl)-3-phenylpropanoic acid | 414 | 2.19 | B | I |
| L288 | 3-(6-{[(2,6-dioxo-1,2,3,6-tetrahydro-4-pyrimidinyl)carbonyl]amino}-1H-benzimidazol-1-yl)-3-phenylpropanoic acid | 420 | 1.27 | B | I |
| L289 | 3-(6-{[(4-methylphenyl)acetyl]amino}-1H-benzimidazol-1-yl)-3-phenylpropanoic acid | 414 | 2.21 | B | I |
| L290 | 3-{6-[(3-methylbenzoyl)amino]-1H-benzimidazol-1-yl}-3-phenylpropanoic acid | 400 | 2.19 | B | I |
| L291 | 3-phenyl-3-{6-[(4-vinylbenzoyl)amino]-1H-benzimidazol-1-yl}propanoic acid | 412 | 2.35 | B | I |
| L292 | 3-{6-[(4-methylbenzoyl)amino]-1H-benzimidazol-1-yl}-3-phenylpropanoic acid | 400 | 2.17 | B | I |
| L293 | 3-{6-[(2-methylbenzoyl)amino]-1H-benzimidazol-1-yl}-3-phenylpropanoic acid | 400 | 2.07 | B | I |
| L294 | 3-(6-{[(3-methylphenyl)acetyl]amino}-1H-benzimidazol-1-yl)-3-phenylpropanoic acid | 414 | 2.21 | B | I |
| L295 | 3-(6-{[(3-nitrophenyl)acetyl]amino}-1H-benzimidazol-1-yl)-3-phenylpropanoic acid | 445 | 2.05 | B | I |
| L296 | 3-{6-[(4-bromobenzoyl)amino]-1H-benzimidazol-1-yl}-3-phenylpropanoic acid | 464 | 2.40 | B | I |
| L297 | 3-phenyl-3-{6-[(9H-xanthen-9-ylcarbonyl)amino]-1H-benzimidazol-1-yl}propanoic acid | 490 | 2.57 | B | I |
| L298 | 3-{6-[(2-phenoxypropanoyl)amino]-1H-benzimidazol-1-yl}-3-phenylpropanoic acid | 430 | 2.08, 2.20* | B | I |
| L299 | 3-(6-{[(1,3-dioxo-1,3-dihydro-2H-isoindol-2-yl)acetyl]amino}-1H-benzimidazol-1-yl)-3-phenylpropanoic acid | 469 | 1.94 | B | I |
| L300 | 3-{6-[(1,3-benzodioxol-5-ylcarbonyl)amino]-1H-benzimidazol-1-yl}-3-phenylpropanoic acid | 430 | 1.92 | B | I |
| L301 | 3-phenyl-3-{6-[(phenylacetyl)amino]-1H-benzimidazol-1-yl}propanoic acid | 400 | 2.06 | B | I |
| L302 | 3-{6-[(bicyclo[2.2.1]hept-5-en-2-ylcarbonyl)amino]-1H-benzimidazol-1-yl}-3-phenylpropanoic acid | 402 | 2.23 | B | I |
| L303 | 3-(6-{[hydroxy(phenyl)acetyl]amino}-1H-benzimidazol-1-yl)-3-phenylpropanoic acid | 416 | 1.85 | B | I |
| L304 | 3-(6-{[(2-naphthyloxy)acetyl]amino}-1H-benzimidazol-1-yl)-3-phenylpropanoic acid | 466 | 2.53 | B | I |
| L305 | 3-phenyl-3-(6-{[(1-phenylcyclopentyl)carbonyl]amino}-1H-benzimidazol-1-yl)propanoic acid | 454 | 2.53 | B | I |
| L306 | 3-phenyl-3-{6-[(tetrahydro-2-furanylcarbonyl)amino]-1H-benzimidazol-1-yl}propanoic acid | 380 | 1.63 | B | I |
| L307 | 3-(6-{[cyclopentyl(phenyl)acetyl]amino}-1H-benzimidazol-1-yl)-3-phenylpropanoic acid | 468 | 2.66 | B | I |
| L308 | 3-{6-[(4-tert-butylbenzoyl)amino]-1H-benzimidazol-1-yl}-3-phenylpropanoic acid | 442 | 2.65 | B | I |
| L309 | 3-{6-[(1-adamantylcarbonyl)amino]-1H-benzimidazol-1-yl}-3-phenylpropanoic acid | 445 | 2.57 | B | I |
| L310 | 3-{6-[(4-methoxybenzoyl)amino]-1H-benzimidazol-1-yl}-3-phenylpropanoic acid | 416 | 1.98 | B | I |
| L311 | 3-{6[(4-cyclohexylbenzoyl)amino]-1H-benzimidazol-1-yl}-3-phenylpropanoic acid | 468 | 2.93 | B | I |
| L312 | 3-[6-(1-naphthoylamino)-1H-benzimidazol-1-yl]-3-phenylpropanoic acid | 436 | 2.50 | B | I |
| L313 | 3-[6-(benzoylamino)-1H-benzimidazol-1-yl]-3-phenylpropanoic acid | 386 | 2.01 | B | I |
| L314 | 3-{6-[(5-isoxazolylcarbonyl)amino]-1H-benzimidazol-1-yl}-3-phenylpropanoic acid | 377 | 1.65 | B | I |
| L315 | 3-(6-{[(2E)-3-(4-bromophenyl)-2-propenoyl]amino}-1H-benzimidazol-1-yl)-3-phenylpropanoic acid | 492 | 2.57, 2.72* | B | I |
| L316 | 3-{6-[(3-bromo-4-methoxybenzoyl)amino]-1H-benzimidazol-1-yl}-3-phenylpropanoic acid | 494 | 2.33 | B | I |

-continued

| Ex. | IUPAC Name | LCMS MH+/MH− | HPLC RT/min | LCMS Method | Mobile Phase |
|---|---|---|---|---|---|
| L317 | 3-{6-[(4-butylbenzoyl)amino]-1H-benzimidazol-1-yl}-3-phenylpropanoic acid | 442 | 2.73 | B | I |
| L318 | 3-(6-{[4-(dimethylamino)benzoyl]amino}-1H-benzimidazol-1-yl)-3-phenylpropanoic acid | 429 | 2.09 | B | I |
| L319 | 3-(6-{[(4-bromo-1-ethyl-3-methyl-1H-pyrazol-5-yl)carbonyl]amino}-1H-benzimidazol-1-yl)-3-phenylpropanoic acid | 496 | 2.06 | B | I |
| L320 | 3-{6-[(4-nitrobenzoyl)amino]-1H-benzimidazol-1-yl}-3-phenylpropanoic acid | 431 | 2.08 | B | I |
| L321 | 3-(6-{[(2-cyclopropyl-4-quinolinyl)carbonyl]amino}-1H-benzimidazol-1-yl)-3-phenylpropanoic acid | 477 | 1.92 | B | I |
| L322 | 3-phenyl-3-[6-({[2-(2-thienyl)-4-quinolinyl]carbonyl}amino)-1H-benzimidazol-1-yl]propanoic acid | 519 | 2.66 | B | I |
| L323 | 3-{6-[(3,5-dinitrobenzoyl)amino]-1H-benzimidazol-1-yl}-3-phenylpropanoic acid | 476 | 2.36 | B | I |
| L324 | 3-phenyl-3-{6-[(3-phenyl-2-propynoyl)amino]-1H-benzimidazol-1-yl}propanoic acid | 410 | 2.36 | B | I |
| L325 | 3-{6-[(4-fluoro-1-naphthoyl)amino]-1H-benzimidazol-1-yl}-3-phenylpropanoic acid | 454 | 2.41 | B | I |
| L326 | 3-(6-{[(acetylamino)acetyl]amino}-1H-benzimidazol-1-yl)-3-phenylpropanoic acid | 381 | 1.06 | B | I |
| L327 | 3-(6-{[(7-methyl-2-phenyl-4-quinolinyl)carbonyl]amino}-1H-benzimidazol-1-yl)-3-phenylpropanoic acid | 527 | 2.77 | B | I |
| L328 | 3-(6-{[(5-bromo-4-methoxy-3-thienyl)carbonyl]amino}-1H-benzimidazol-1-yl)-3-phenylpropanoic acid | 500 (−ve) | 2.11 | B | I |
| L329 | 3-{6-[(4-[1,1'-biphenyl]-4-yl-4-oxobutanoyl)amino]-1H-benzimidazol-1-yl}-3-phenylpropanoic acid | 518 | 2.62 | B | I |
| L330 | 3-{6-[(1-cyclohexen-1-ylcarbonyl)amino]-1H-benzimidazol-1-yl}-3-phenylpropanoic acid | 390 | 2.10 | B | I |
| L331 | 3-(6-{[(4-bromophenyl)acetyl]amino}-1H-benzimidazol-1-yl)-3-phenylpropanoic acid | 478 | 2.39 | B | I |
| L332 | 3-(6-{[2-(methylsulfanyl)benzoyl]amino}-1H-benzimidazol-1-yl)-3-phenylpropanoic acid | 432 | 2.11 | B | I |
| L333 | 3-(6-{[(2E)-3-(5-bromo-2-ethoxyphenyl)-2-propenoyl]amino}-1H-benzimidazol-1-yl)-3-phenylpropanoic acid | 536 | 2.60, 2.74* | B | I |
| L334 | 3-(6-{[4-(methylsulfonyl)benzoyl]amino}-1H-benzimidazol-1-yl)-3-phenylpropanoic acid | 464 | 1.78 | B | I |
| L335 | 3-(6-{[2-nitro-4-(trifluoromethyl)benzoyl]amino}-1H-benzimidazol-1-yl)-3-phenylpropanoic acid | 499 | 2.42 | B | I |
| L336 | 3-{6-[([1,1'-biphenyl]-4-ylcarbonyl)amino]-1H-benzimidazol-1-yl}-3-phenylpropanoic acid | 462 | 2.61 | B | I |
| L337 | 3-{6-[(4-benzoylbenzoyl)amino]-1H-benzimidazol-1-yl}-3-phenylpropanoic acid | 490 | 2.53 | B | I |
| L338 | 3-phenyl-3-(6-{[4-(trifluoromethyl)benzoyl]amino}-1H-benzimidazol-1-yl)propanoic acid | 454 | 2.45 | B | I |
| L339 | 3-{6-[(4-acetylbenzoyl)amino]-1H-benzimidazol-1-yl}-3-phenylpropanoic acid | 429 | 1.94 | B | I |
| L340 | 3-{6-[(4-cyanobenzoyl)amino]-1H-benzimidazol-1-yl}-3-phenylpropanoic acid | 411 | 2.00 | B | I |
| L341 | 3-(6-{[2,4-bis(trifluoromethyl)benzoyl]amino}-1H-benzimidazol-1-yl)-3-phenylpropanoic acid | 522 | 2.59 | B | I |
| L342 | 3-phenyl-3-(6-{[3-(trifluoromethyl)benzoyl]amino}-1H-benzimidazol-1-yl)propanoic acid | 454 | 2.42 | B | I |
| L343 | 3-{6-[(3-cyanobenzoyl)amino]-1H-benzimidazol-1-yl}-3-phenylpropanoic acid | 411 | 2.02 | B | I |
| L344 | 3-(6-{[4-(3-methyl-5-oxo-4,5-dihydro-1H-pyrazol-1-yl)benzoyl]amino}-1H-benzimidazol-1-yl)-3-phenylpropanoic acid | 482 | 1.79 | B | I |
| L345 | 3-{6-[(1H-benzimidazol-5-ylcarbonyl)amino]-1H-benzimidazol-1-yl}-3-phenylpropanoic acid | 426 | 1.12 | B | I |

-continued

| Ex. | IUPAC Name | LCMS MH+/MH− | HPLC RT/min | LCMS Method | Mobile Phase |
|---|---|---|---|---|---|
| L346 | 3-{6-[(diphenylacetyl)amino]-1H-benzimidazol-1-yl}-3-phenylpropanoic acid | 476 | 2.58 | B | I |
| L347 | 3-{6-[(2-hydroxybenzoyl)amino]-1H-benzimidazol-1-yl}-3-phenylpropanoic acid | 402 | 2.12 | B | I |
| L348 | 3-{6-[(4-ethylbenzoyl)amino]-1H-benzimidazol-1-yl}-3-phenylpropanoic acid | 414 | 2.37 | B | I |
| L349 | 3-(6-{[3-(2,5-dioxo-2,5-dihydro-1H-pyrrol-1-yl)propanoyl]amino}-1H-benzimidazol-1-yl)-3-phenylpropanoic acid | 433 | 1.57 | B | I |
| L350 | 3-{6-[(3-bromo-2,6-dimethoxybenzoyl)amino]-1H-benzimidazol-1-yl}-3-phenylpropanoic acid | 526 | 2.24 | B | I |
| L351 | 3-{6-[(4-bromo-2,3,5,6-tetrafluorobenzoyl)amino]-1H-benzimidazol-1-yl}-3-phenylpropanoic acid | 538 | 2.57 | B | I |
| L352 | 3-{6-[(5-bromo-2-furoyl)amino]-1H-benzimidazol-1-yl}-3-phenylpropanoic acid | 454 | 2.09 | B | I |
| L353 | 3-{6-[(3-iodobenzoyl)amino]-1H-benzimidazol-1-yl}-3-phenylpropanoic acid | 512 | 2.49 | B | I |
| L354 | 3-{6-[(2-formylbenzoyl)amino]-1H-benzimidazol-1-yl}-3-phenylpropanoic acid | 414 | 1.81 | B | I |
| L355 | 3-{6-[(2-bromobenzoyl)amino]-1H-benzimidazol-1-yl}-3-phenylpropanoic acid | 464 | 2.08 | B | I |
| L356 | 3-{6-[(3-bromobenzoyl)amino]-1H-benzimidazol-1-yl}-3-phenylpropanoic acid | 466 | 2.40 | B | I |
| L357 | 3-(6-{[(5-bromo-3-pyridinyl)carbonyl]amino}-1H-benzimidazol-1-yl)-3-phenylpropanoic acid | 467 | 2.00 | B | I |
| L358 | 3-(6-{[(5-bromo-2-thienyl)carbonyl]amino}-1H-benzimidazol-1-yl)-3-phenylpropanoic acid | 472 | 2.37 | B | I |
| L359 | 3-{6-[(2-bromo-5-methoxybenzoyl)amino]-1H-benzimidazol-1-yl}-3-phenylpropanoic acid | 494 | 2.18 | B | I |
| L360 | 3-{6-[(4-bromo-2-methylbenzoyl)amino]-1H-benzimidazol-1-yl}-3-phenylpropanoic acid | 478 | 2.41 | B | I |
| L361 | 3-{6-[(4-bromo-2-chlorobenzoyl)amino]-1H-benzimidazol-1-yl}-3-phenylpropanoic acid | 500 | 2.51 | B | I |
| L362 | 3-(6-{[(2E)-3-(3-bromo-4-fluorophenyl)-2-propenoyl]amino}-1H-benzimidazol-1-yl)-3-phenylpropanoic acid | 510 | 2.55 | B | I |
| L363 | 3-(6-{[(2E)-3-(6-bromo-1,3-benzodioxol-5-yl)-2-propenoyl]amino}-1H-benzimidazol-1-yl)-3-phenylpropanoic acid | 536 | 2.48, 2.60* | B | I |
| L364 | 3-{6-[(2-oxo-3-phenylpropanoyl)amino]-1H-benzimidazol-1-yl}-3-phenylpropanoic acid | 429 | 2.58 | B | I |
| L365 | 3-{6-[(4-oxopentanoyl)amino]-1H-benzimidazol-1-yl}-3-phenylpropanoic acid | 380 | 1.44 | B | I |
| L366 | 3-phenyl-3-[6-({[2-(phenylsulfanyl)-3-pyridinyl]carbonyl}amino)-1H-benzimidazol-1-yl]propanoic acid | 495 | 2.17 | B | I |
| L367 | 3-{6-[(2-hydroxy-5-nitrobenzoyl)amino]-1H-benzimidazol-1-yl}-3-phenylpropanoic acid | 447 | 2.25 | B | I |
| L368 | 3-{6-[(2-hydroxy-3-methoxybenzoyl)amino]-1H-benzimidazol-1-yl}-3-phenylpropanoic acid | 432 | 2.18 | B | I |
| L369 | 3-(6-{[(4-hydroxy-3-methoxyphenyl)acetyl]amino}-1H-benzimidazol-1-yl)-3-phenylpropanoic acid | 446 | 1.70 | B | I |
| L370 | 3-{6-[(2,5-dihydroxybenzoyl)amino]-1H-benzimidazol-1-yl}-3-phenylpropanoic acid | 418 | 1.84 | B | I |
| L371 | 3-{6-[(2-hydroxy-3-methylbenzoyl)amino]-1H-benzimidazol-1-yl}-3-phenylpropanoic acid | 416 | 2.47 | B | I |
| L372 | 3-{6-[(3-hydroxy-4-methylbenzoyl)amino]-1H-benzimidazol-1-yl}-3-phenylpropanoic acid | 416 | 1.89 | B | I |
| L373 | 3-(6-{[(3-hydroxy-4-methoxyphenyl)acetyl]amino}-1H-benzimidazol-1-yl)-3-phenylpropanoic acid | 446 | 1.75 | B | I |
| L374 | 3-(6-{[(4,7-dimethylpyrazolo[5,1-c][1,2,4]triazin-3-yl)carbonyl]amino}-1H-benzimidazol-1-yl)-3-phenylpropanoic acid | 456 | 1.78 | B | I |
| L375 | 3-(6-{[3-(2,4-dihydroxyphenyl)propanoyl]amino}-1H-benzimidazol-1-yl)-3-phenylpropanoic acid | 446 | 1.67 | B | I |

-continued

| Ex. | IUPAC Name | LCMS MH+/MH− | HPLC RT/min | LCMS Method | Mobile Phase |
|---|---|---|---|---|---|
| L376 | 3-(6-{[(3,5-ditert-butyl-4-hydroxyphenyl)acetyl]amino}-1H-benzimidazol-1-yl)-3-phenylpropanoic acid | 528 | 2.81 | B | I |
| L377 | 3-(6-{[(6-hydroxy-2,5,7,8-tetramethyl-3,4-dihydro-2H-chromen-2-yl)carbonyl]amino}-1H-benzimidazol-1-yl)-3-phenylpropanoic acid | 514 | 2.42 | B | I |
| L378 | 3-{6-[(5-formyl-2-hydroxybenzoyl)amino]-1H-benzimidazol-1-yl}-3-phenylpropanoic acid | 430 | 2.03 | B | I |
| L379 | 3-{6-[(3,5-dichloro-2-hydroxybenzoyl)amino]-1H-benzimidazol-1-yl}-3-phenylpropanoic acid | 470 | 2.79 | B | I |
| L380 | 3-phenyl-3-{6-[(2,4,6-trihydroxybenzoyl)amino]-1H-benzimidazol-1-yl}propanoic acid | 434 | 1.88 | B | I |
| L381 | 3-{6-[(2-hydroxybenzoyl)amino]-1H-benzimidazol-1-yl}-3-phenylpropanoic acid | 402 | 2.06 | B | I |
| L382 | 3-phenyl-3-{6-[(2,3,5-trichloro-6-hydroxybenzoyl)amino]-1H-benzimidazol-1-yl}propanoic acid | 506 | 2.35 | B | I |
| L383 | 3-{6-[(5-chloro-2-hydroxybenzoyl)amino]-1H-benzimidazol-1-yl}-3-phenylpropanoic acid | 436 | 2.38 | B | I |
| L384 | 3-{6-[(5-bromo-2-hydroxybenzoyl)amino]-1H-benzimidazol-1-yl}-3-phenylpropanoic acid | 482 | 2.47 | B | I |
| L385 | 3-{6-[(2-hydroxy-4-methylbenzoyl)amino]-1H-benzimidazol-1-yl}-3-phenylpropanoic acid | 416 | 2.3 | B | I |
| L386 | 3-(6-{[(3,4-dihydroxyphenyl)acetyl]amino}-1H-benzimidazol-1-yl)-3-phenylpropanoic acid | 432 | 1.54 | B | I |
| L387 | 3-{6-[(2-fluoro-6-iodobenzoyl)amino]-1H-benzimidazol-1-yl}-3-phenylpropanoic acid | 530 | 2.14 | B | I |

The invention claimed is:
1. A compound of Formula 1

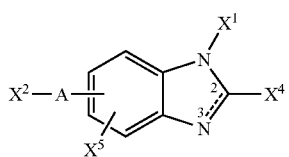

or a pharmaceutically acceptable salt, wherein:
the dashed line designates that a double bond or a single bond connects the nitrogen at the three position with the carbon at the two position;
each A and A' is independently a direct bond, —C(O)N($R^4$)—, —N($R^4$)C(O)—, —N($R^4$)$SO_2$—, —$SO_2$N($R^4$)—, —N($R^4$)C(O)($CR^4R^5$)$_p$NHC(O)—, —N($R^4$)C(O)($CR^4R^5$)$_p$N($R^4$)—, —N($R^4$)C(S)($CR^4R^5$)$_p$N($R^4$)—, —N($R^4$)C(O)($CR^4R^5$)$_p$C(O)—, —N($R^4$)C(O)O—, —N($R^4$)C(O)S—, —C(O)—, —N($R^3$)—, —S— or —O—, wherein p is an integer from 0 to 5 and the left dash of the foregoing groups is attached to the benzimidazole ring of the compound of Formula 1;
$X^1$ is —$CH_2$—CH($AR^1$)—$CO_2H$, —CH($AR^1$)—$CH_2$—$CO_2H$ or —C($AR^1$)=$CHCO_2H$;
$X^2$ is H, $C_1$-$C_{20}$ alkyl, $C_2$-$C_{20}$ alkenyl, $C_2$-$C_{20}$ alkynyl, —($CR^4R^5$)$_t$($C_3$-$C_{20}$ cycloalkyl), —($CR^4R^5$)$_t$($C_6$-$C_{10}$ aryl), or —($CR^4R^5$)$_t$(4 to 12 membered heterocyclic), wherein each $X^2$ group, except H, is substituted by $X^3$, each t is independently an integer from 0 to 5, said alkyl, alkenyl and alkynyl groups optionally contain 1 or 2 hetero moieties selected from O, —S(O)$_j$— wherein j is an integer from 0 to 2, and —N($R^4$)— with the proviso that two O atoms, two S atoms, or an O and S atom are not attached directly to each other, and the proviso that an O atom, a S atom or a N atom are not attached directly to a triple bond or non-aromatic double bond;
said cycloalkyl, aryl and heterocyclic $X^2$ groups are optionally fused to one or two ring systems independently selected from a benzene ring, a $C_5$-$C_8$ cycloalkyl group, and a 4 to 10 membered heterocyclic group;
—($CR^4R^5$)$_t$— optionally includes a carbon-carbon double or triple bond where t is an integer from 2 to 5, or where t is 1 the —($CR^4R^5$)$_t$— moiety of —($CR^4R^5$)$_t$(4 to 12 membered heterocyclic) and —($CR^4R^5$)$_t$($C_3$-$C_{20}$ cycloalkyl) optionally is attached by a carbon-carbon double bond to a carbon of the cycloalkyl group or a non-aromatic carbon of the 4 to 12 membered heterocyclic group;
said cycloalkyl optionally includes one or two carbon-carbon double or triple bonds;
and $X^2$, except when H, optionally is substituted by 1 to 5 $R^2$ groups;
$X^3$ is H, 2-aminoimidazoyl, 2-aminobenzimidazoyl, 2-aminopyridyl, 2-aminopyrimidyl, or 2-aminopyrazinyl, wherein $X^3$, except when H, optionally is substituted by 1 or 2 $R^2$ groups;
$X^4$ is H, $C_1$-$C_{10}$ alkyl, —$NR^3R^4$, —$SR^3$, or —$OR^3$;
each $X^5$ and $R^2$ is independently selected from $C_1$-$C_{10}$ alkyl, $C_2$-$C_{10}$ alkenyl, $C_2$-$C_{10}$ alkynyl, halo, cyano, nitro, trifluoromethyl, difluoromethoxy, trifluoromethoxy, azido, —$OR^3$, —C(O)$R^3$, —C(O)$OR^3$, —NR⁴C(O)OR⁶, —NR⁴C(O)R³, —OC(O)R³, —NR⁴SO₂R⁶, —SO₂NR³R⁴, —NR⁴C(O)R³, —C(O)NR³R⁴, —O—N═CR³R⁴, —NR⁴C(O)NR³R⁴, —NR⁴C(S)NR³R⁴, —NR³R⁴, —S(O)ⱼ(CR⁴R⁵)ₜ(C₆-C₁₀ aryl), —S(O)ⱼ(CR⁴R⁵)ₜ(4 to 12 membered heterocyclic), —S(O)ⱼ(C₁-C₆ alkyl), —(CR⁴R⁵)ₜ(C₆-C₁₀ aryl), —(CR⁴R⁵)ₚC(O)(CR⁴R⁵)ₜ(C₆-C₁₀ aryl), —(CR⁴R⁵)ₚO(CR⁴R⁵)ₜ(C₆-C₁₀ aryl), —NR⁴(CR⁴R⁵)ₜ(C₆-C₁₀ aryl), —(CR⁴R⁵)ₜ(4 to 12 membered heterocyclic), and —(CR⁴R⁵)ₚC(O)(CR⁴R⁵)ₜ(4 to 12 membered heterocyclic), wherein each t is independently an integer from 0 to 5, each p is independently an integer from 0 to 5, and each j is an integer from 0 to 2; said alkyl, alkenyl and alkynyl groups optionally contain 1 or 2 hetero moieties selected from O, —S(O)ⱼ— wherein j is an integer from 0 to 2, and —N(R³)— with the proviso that two O atoms, two S atoms, or an O and S atom are not attached directly to each other, and the proviso that an O atom, a S atom or a N atom are not attached directly to a triple bond or a non-aromatic double bond; said cycloalkyl, aryl and heterocyclic R² groups are optionally fused to a C₆-C₁₀ aryl group, a C₅-C₈ cycloalkyl group, or a 4 to 12 membered heterocyclic group; and said alkyl, alkenyl, alkynyl, aryl and heterocyclic moieties of the foregoing R² groups are optionally substituted by 1 to 5 substituents independently selected from halo, cyano, nitro, trifluoromethyl, difluoromethoxy, trifluoromethoxy, azido, —NR⁴SO₂R⁶, —SO₂NR³R⁴, —C(O)R³, —C(O)OR³, —OC(O)R³, —NR⁴C(O)OR⁶, —NR⁴C(O)R³, —C(O)NR³R⁴, —NR³R⁴, —OR³, C₁-C₁₀ alkyl, —S(O)ⱼ(C₁-C₆ alkyl), —(CR⁴R⁵)ₜ(C₆-C₁₀ aryl), and —(CR⁴R⁵)ₜ(4 to 12 membered heterocyclic), wherein each t is independently an integer from 0 to 5 and each j is independently an integer from 0 to 2;

R¹ is —(CR⁴R⁵)ₜ(C₆-C₁₀ aryl) or —(CR⁴R⁵)ₜ(4 to 12 membered heterocyclic) wherein t is an integer from 0 to 5; and R¹ is optionally substituted with 1 to 5 R² groups;

each R³ is independently selected from H, C₁-C₁₀ alkyl, —(CR⁴R⁵)ₜ(C₆-C₁₀ aryl), and —(CR⁴R⁵)ₜ(4 to 12 membered heterocyclic), wherein each t is independently an integer from 0 to 5; said alkyl group optionally includes 1 or 2 hetero moieties selected from O, —S(O)ⱼ— wherein j is an integer ranging from 0 to 2, and —N(R⁴)— with the proviso that two O atoms, two S atoms, or an O and S atom are not attached directly to each other; said cycloalkyl, aryl and heterocyclic R³ groups are optionally fused to a C₆-C₁₀ aryl group, a C₅-C₈ cycloalkyl group, or a 4 to 12 membered heterocyclic group; and R³, except when H, is optionally substituted by 1 to 5 substituents independently selected from oxo, halo, cyano, nitro, trifluoromethyl, difluoromethoxy, trifluoromethoxy, azido, —C(O)R⁴, —C(O)OR⁴, —OC(O)R⁴, —NR⁴C(O)R⁵, —C(O)NR⁴R⁵, —NR⁴R⁵, hydroxy, C₁-C₆ alkyl, trifluoromethyl, trifluoromethoxy, and C₁-C₆ alkoxy, and with the proviso that R³ must be attached through a carbon atom unless R³ is H;

each R⁴ or R⁵ is independently H or C₁-C₆ alkyl; or where R⁴ and R⁵ are attached to the same carbon atom, R⁴ and R⁵ may be taken together to form a C₃-C₁₀ cycloalkyl group;

each R⁶ is independently selected from C₁-C₁₀ alkyl, —(CR⁴R⁵)ₜ(C₆-C₁₀ aryl), and —(CR⁴R⁵)ₜ(4 to 12 membered heterocyclic), wherein each t is independently an integer from 0 to 5; said alkyl group optionally includes 1 or 2 hetero moieties selected from O, —S(O)ⱼ— wherein j is an integer ranging from 0 to 2, and —N(R⁴)— with the proviso that two O atoms, two S atoms, or an O and S atom are not attached directly to each other; said cycloalkyl, aryl and heterocyclic R⁶ groups are optionally fused to a C₆-C₁₀ aryl group, a C₅-C₈ cycloalkyl group, or a 4 to 12 membered heterocyclic group; and R⁶ is optionally substituted by 1 to 5 substituents independently selected from oxo, halo, cyano, nitro, trifluoromethyl, difluoromethoxy, trifluoromethoxy, azido, —C(O)R⁴, —C(O)OR⁴, —OC(O)R⁴, —NR⁴C(O)R⁵, —C(O)NR⁴R⁵, —NR⁴R⁵, hydroxy, C₁-C₆ alkyl, trifluoromethyl, trifluoromethoxy, and C₁-C₆ alkoxy.

2. The compound according to claim 1 wherein the A moiety in -A-X² is selected from a direct bond, —C(O)NH—, —NHC(O)—, —SO₂NH—, —NHSO₂—, —NHC(O)NH—, and —NHC(S)NH—.

3. The compound according to claim 1 selected from the group consisting of:
3-(1H-Benzimidazol-1-yl)-3-(4-ethylphenyl)propanoic acid;
3-Phenyl-3-[6-(trifluoromethyl)-1H-benzimidazol-1-yl]propanoic acid;
(3R)-3-(1H-Benzimidazol-1-yl)-3-phenylpropanoic acid;
(3S)-3-(1H-Benzimidazol-1-yl)-4-phenylbutanoic acid;
3-(1H-Benzimidazol-1-yl)-3-(4-chlorophenyl)propanoic acid;
3-Phenyl-3-(4-{4-[(1,4,5,6-tetrahydro-2-pyrimidinylamino)carbonyl]-1-piperidinyl}-1H-benzimidazol-1-yl)propanoic acid;
3-{5-[(3-Nitrobenzoyl)amino]-1H-benzimidazol-1-yl}-3-phenylpropanoic acid;
3-{5-[(3-Aminobenzoyl)amino]-1H-benzimidazol-1-yl}-3-phenylpropanoic acid;
3-{5-[(3-{[Amino(imino)methyl]amino}benzoyl)amino]-1H-benzimidazol-1-yl}-3-phenylpropanoic acid;
3-{5-[(4-{[Amino(imino)methyl]amino}benzoyl)amino]-1H-benzimidazol-1-yl}-3-phenylpropanoic acid;
3-{5-[(Anilinocarbonyl)amino]-1H-benzimidazol-1-yl}-3-phenylpropanoic acid;
3-{5-[(2-Phenoxybenzoyl)amino]-1H-benzimidazol-1-yl}-3-phenylpropanoic acid;
3-{5-[(2,6-Dimethoxybenzoyl)amino]-1H-benzimidazol-1-yl}-3-phenylpropanoic acid;
3-Phenyl-3-[5-({[2-(phenylsulfanyl)-3-pyridinyl]carbonyl}amino)-1H-benzimidazol-1-yl]propanoic acid;
3-(5-{[(2-Phenoxy-3-pyridinyl)carbonyl]amino}-1H-benzimidazol-1-yl)-3-phenylpropanoic acid;
3-{5-[(2-Hydroxy-5-nitrobenzoyl)amino]-1H-benzimidazol-1-yl}-3-phenylpropanoic acid;
3-{6-[(2-aminobenzoyl)amino]-1H-benzimidazol-1-yl}-3-phenylpropanoic acid;
3-(6-{[3-(1H-Indol-3-yl)propanoyl]amino}-1H-benzimidazol-1-yl)-3-phenylpropanoic acid;
3-Phenyl-3-[6-({[2-(phenylsulfanyl)-3-pyridinyl]carbonyl}amino)-1H-benzimidazol-1-yl]propanoic acid;
3-{6-[(2-Bromo-5-methoxybenzoyl)amino]-1H-benzimidazol-1-yl}-3-phenylpropanoic acid;
3-Phenyl-3-(6-{[(4-phenyl-1,2,3-thiadiazol-5-yl)carbonyl]amino}-1H-benzimidazol-1-yl)propanoic acid;
3-{6-[(3-Bromo-2,6-dimethoxybenzoyl)amino]-1H-benzimidazol-1-yl}-3-phenylpropanoic acid;

3-Phenyl-3-{6-[(2,3,5-trichloro-6-hydroxybenzoyl)amino]-1H-benzimidazol-1-yl}propanoic acid;
3-(5-Nitro-1H-benzimidazol-1-yl)-3-(3-pyridinyl)propanoic acid;
3-(5-Amino-1H-benzimidazol-1-yl)-3-(3-pyridinyl)propanoic acid;
3-{5-[(Phenylsulfonyl)amino]-1H-benzimidazol-1-yl}-3-(3-pyridinyl)propanoic acid;
3-(2-Naphthyl)-3-(5-nitro-1H-benzimidazol-1-yl)propanoic acid;
3-(5-Amino-1H-benzimidazol-1-yl)-3-(2-naphthyl)propanoic acid;
3-(2-Naphthyl)-3-{5-[(phenylsulfonyl)amino]-1H-benzimidazol-1-yl}propanoic acid;
3-(5-Amino-1H-benzimidazol-1-yl)-3-(4-methoxyphenyl)propanoic acid;
3-(4-Methoxyphenyl)-3-{5-[(phenylsulfonyl)amino]-1H-benzimidazol-1-yl}propanoic acid;
1-(2-Carboxy-1-phenylethyl)-1H-benzimidazole-5-carboxylic acid;
3-[5-(Anilinocarbonyl)-1H-benzimidazol-1-yl]-3-phenylpropanoic acid; and
3-Phenyl-3-(5-{[4-(2-pyrazinyl)-1-piperazinyl]carbonyl}-1H-benzimidazol-1-yl)propanoic acid;

or a pharmaceutically acceptable salt thereof.

4. A compound selected from:

3-phenyl-3-{5-[(2-quinolinylcarbonyl)amino]-1H-benzimidazol-1-yl}propanoic acid
3-{5-[(3-isoquinolinylcarbonyl)amino]-1H-benzimidazol-1-yl}-3-phenylpropanoic acid
3-phenyl-3-{5-[(2-quinoxalinylcarbonyl)amino]-1H-benzimidazol-1-yl}propanoic acid
3-{5-[(1-isoquinolinylcarbonyl)amino]-1H-benzimidazol-1-yl}-3-phenylpropanoic acid
3-{5-[(2,3-dihydro-1H-indol-2-ylcarbonyl)amino]-1H-benzimidazol-1-yl}-3-phenylpropanoic acid
3-phenyl-3-{5-[(2-quinoxalinylcarbonyl)amino]-1H-benzimidazol-1-yl}propanoic acid
3-phenyl-3-{5-[(2-pyrazinylcarbonyl)amino]-1H-benzimidazol-1-yl}propanoic acid
3-phenyl-3-{5-[(3-pyridinylcarbonyl)amino]-1H-benzimidazol-1-yl}propanoic acid
3-[5-(isonicotinoylamino)-1H-benzimidazol-1-yl]-3-phenylpropanoic acid
3-(5-{[(2-hydroxy-3-pyridinyl)carbonyl]amino}-1H-benzimidazol-1-yl)-3-phenylpropanoic acid
3-{5-[(1H-indol-2-ylcarbonyl)amino]-1H-benzimidazol-1-yl}-3-phenylpropanoic acid
3-{5-[(1H-indol-3-ylcarbonyl)amino]-1H-benzimidazol-1-yl}-3-phenylpropanoic acid
3-{5-[(3-nitrobenzoyl)amino]-1H-benzimidazol-1-yl}-3-phenylpropanoic acid
3-phenyl-3-{5-[(3-pyridinylacetyl)amino]-1H-benzimidazol-1-yl}propanoic acid
3-{5-[(1H-imidazol-4-ylacetyl)amino]-1H-benzimidazol-1-yl}-3-phenylpropanoic acid
3-(5-{[(2E)-3-(3-nitrophenyl)-2-propenoyl]amino}-1H-benzimidazol-1-yl)-3-phenylpropanoic acid
3-(5-{[3-(1H-benzimidazol-2-yl)propanoyl]amino}-1H-benzimidazol-1-yl)-3-phenylpropanoic acid
3-phenyl-3-(5-{[3-(3,4,5-trimethoxyphenyl)propanoyl]amino}-1H-benzimidazol-1-yl)propanoic acid
3-{5-[(1H-indol-3-ylacetyl)amino]-1H-benzimidazol-1-yl}-3-phenylpropanoic acid
3-(5-{[3-(1H-indol-3-yl)propanoyl]amino}-1H-benzimidazol-1-yl)-3-phenylpropanoic acid
3-phenyl-3-{5-[(2-pyridinylcarbonyl)amino]-1H-benzimidazol-1-yl}propanoic acid
3-(5-{[4-(1H-indol-3-yl)butanoyl]amino}-1H-benzimidazol-1-yl)-3-phenylpropanoic acid
3-(5-{[(5-methyl-2-pyrazinyl)carbonyl]amino}-1H-benzimidazol-1-yl)-3-phenylpropanoic acid
3-(5-{[(5-methyl-2-phenyl-2H-1,2,3-triazol-4-yl)carbonyl]amino}-1H-benzimidazol-1-yl)-3-phenylpropanoic acid
3-(5-{[(4-oxo-4,5,6,7-tetrahydro-1-benzofuran-3-yl)carbonyl]amino}-1H-benzimidazol-1-yl)-3-phenylpropanoic acid
3-[5-({[2-(methylsulfanyl)-3-pyridinyl]carbonyl}amino)-1H-benzimidazol-1-yl]-3-phenylpropanoic acid
3-[5-({[3-chloro-4-(isopropylsulfonyl)-2-thienyl]carbonyl}amino)-1H-benzimidazol-1-yl]-3-phenylpropanoic acid
3-(5-{[(6-oxo-1,4,5,6-tetrahydro-3-pyridazinyl)carbonyl]amino}-1H-benzimidazol-1-yl)-3-phenylpropanoic acid
3-[5-({[2-(2,3-dihydro-1,4-benzodioxin-2-yl)-1,3-thiazol-4-yl]carbonyl}amino)-1H-benzimidazol-1-yl]-3-phenylpropanoic acid
3-[5-({(2E)-3-[3-nitro-4-(1-pyrrolidinyl)phenyl]-2-propenoyl}amino)-1H-benzimidazol-1-yl]-3-phenylpropanoic acid
3-(5-{[3-(2-oxocyclododecyl)propanoyl]amino}-1H-benzimidazol-1-yl)-3-phenylpropanoic acid
3-(5-{[(1-tert-butyl-3-methyl-1H-pyrazol-5-yl)carbonyl]amino}-1H-benzimidazol-1-yl)-3-phenylpropanoic acid
3-(5-{[(2Z)-2-(3-oxo-2-benzofuran-1(3H)-ylidene)ethanoyl]amino}-1H-benzimidazol-1-yl)-3-phenylpropanoic acid
3-{5-[(1-benzothien-2-ylcarbonyl)amino]-1H-benzimidazol-1-yl}-3-phenylpropanoic acid
3-phenyl-3-(5-{[4-(trifluoromethoxy)benzoyl]amino}-1H-benzimidazol-1-yl)propanoic acid
3-(5-{[(5-chloro-2-hydroxy-3-pyridinyl)carbonyl]amino}-1H-benzimidazol-1-yl)-3-phenylpropanoic acid
3-(5-{[(2E)-4-oxo-4-(2,3,4,5,6-pentamethylphenyl)-2-butenoyl]amino}-1H-benzimidazol-1-yl)-3-phenylpropanoic acid
3-(5-{[(6-bromo-2-oxo-2H-chromen-3-yl)carbonyl]amino}-1H-benzimidazol-1-yl)-3-phenylpropanoic acid
3-phenyl-3-(5-{[4-(trifluoroacetyl)benzoyl]amino}-1H-benzimidazol-1yl)propanoic acid
3-[5-({[(4-chlorobenzoyl)amino]acetyl}amino)-1H-benzimidazol-1-yl]-3-phenylpropanoic acid 3-(5-{[(2,7-dimethylpyrazolo[1,5-a]pyrimidin-6-yl)carbonyl]amino}-1H-benzimidazol-1-yl)-3-phenylpropanoic acid
3-(5-{[(4-acetyl-5-methyl-2-oxo-2,3-dihydro-1H-pyrrol-3-yl)acetyl]amino}-1H-benzimidazol-1-yl)-3-phenylpropanoic acid
3-phenyl-3-(5-{[(4-phenyl-1,2,3-thiadiazol-5-yl)carbonyl]amino}-1H-benzimidazol-1-yl)propanoic acid
3-[5-({[1-(4-chlorobenzyl)-5-oxo-3-pyrrolidinyl]carbonyl}amino)-1H-benzimidazol-1-yl]-3-phenylpropanoic acid
3-(5-{[({[(Z)-1-(4-chlorophenyl)ethylidene]amino}oxy)acetyl]amino}-1H-benzimidazol-1-yl)-3-phenylpropanoic acid
3-phenyl-3-{5-[(1,2,3-thiadiazol-4-ylcarbonyl)amino]-1H-benzimidazol-1-yl}propanoic acid
3-(5-{[(5-chloro-1-benzothien-3-yl)acetyl]amino}-1H-benzimidazol-1-yl)-3-phenylpropanoic acid
3-[5-({[5-chloro-2-(methylsulfanyl)-4-pyrimidinyl]carbonyl}amino)-1H-benzimidazol-1-yl]-3-phenylpropanoic acid
3-[5-({[1-(2-furylmethyl)-5-oxo-3-pyrrolidinyl]carbonyl}amino)-1H-benzimidazol-1-yl]-3-phenylpropanoic acid
3-(5-{[(3-tert-butyl-1-methyl-1H-pyrazol-5-yl)carbonyl]amino}-1H-benzimidazol-1-yl)-3-phenylpropanoic acid
3-(5-{[(5-oxo-2-pyrrolidinyl)carbonyl]amino}-1H-benzimidazol-1-yl)-3-phenylpropanoic acid
3-(5-{[(2,5-dimethoxyphenyl)acetyl]amino}-1H-benzimidazol-1-yl)-3-phenylpropanoic acid
3-[5-({[2-(4-methylphenoxy)-3-pyridinyl]carbonyl}amino)-1H-benzimidazol-1-yl]-3-phenylpropanoic acid
3-[5-(2-methyl-6-nitro-4-oxo-3(4H)-quinazolinyl)-1H-benzimidazol-1-yl]-3-phenylpropanoic acid
3-(5-{[(3-methoxyphenyl)acetyl]amino}-1H-benzimidazol-1-yl)-3-phenylpropanoic acid
3-(5-{[(4-methoxyphenyl)acetyl]amino}-1H-benzimidazol-1-yl)-3-phenylpropanoic acid
3-(5-{[(2-methoxyphenyl)acetyl]amino}-1H-benzimidazol-1-yl)-3-phenylpropanoic acid
3-(5-{[(2-phenoxy-3-pyridinyl)carbonyl]amino}-1H-benzimidazol-1-yl)-3-phenylpropanoic acid
3-[5-({2-[4-(aminocarbonyl)phenoxy]-2-methylpropanoyl}amino)-1H-benzimidazol-1-yl]-3-phenylpropanoic acid
3-phenyl-3-{5-[(1,2,3,4-tetrahydro-2-naphthalenylcarbonyl)amino]-1H-benzimidazol-1-yl}propanoic acid
3-(5-{[(3,5-dimethyl-4-isoxazolyl)carbonyl]amino}-1H-benzimidazol-1-yl)-3-phenylpropanoic acid
3-phenyl-3-{5-[(1H-pyrrol-2-ylcarbonyl)amino]-1H-benzimidazol-1-yl}propanoic acid
3-[5-({[(2S)-5-oxopyrrolidinyl]carbonyl}amino)-1H-benzimidazol-1-yl]-3-phenylpropanoic acid
3-phenyl-3-[5-({[(3S,4R,5S)-3,4,5-trihydroxy-1-cyclohexen-1-yl]carbonyl}amino)-1H-benzimidazol-1-yl]propanoic acid
3-{5-[(cyclohexylacetyl)amino]-1H-benzimidazol-1-yl}-3-phenylpropanoic acid
3-phenyl-3-(5-{[4-(1H-pyrrol-1-yl)benzoyl]amino}-1H-benzimidazol-1-yl)propanoic acid
3-(5-{[(2,4-dihydroxy-5-pyrimidinyl)carbonyl]amino}-1H-benzimidazol-1-yl)-3-phenylpropanoic acid
3-(5-{[2-(1,3-dioxo-1,3-dihydro-2H-isoindol-2-yl)propanoyl]amino}-1H-benzimidazol-1-yl)-3-phenylpropanoic acid
3-(5-{[3-(1,3-dioxo-1,3-dihydro-2H-isoindol-2-yl)propanoyl]amino}-1H-benzimidazol-1-yl)-3-phenylpropanoic acid
3-[5-({[1-(4-chlorophenyl)cyclopentyl]carbonyl}amino)-1H-benzimidazol-1-yl]-3-phenylpropanoic acid
3-(5-{[(4-oxo-2-thioxo-1,3-thiazolidin-3-yl)acetyl]amino}-1H-benzimidazol-1-yl)-3-phenylpropanoic acid
3-{5-[([1,1'-biphenyl]-4-ylacetyl)amino]-1H-benzimidazol-1-yl}-3-phenylpropanoic acid
3-(5-{[(6-methoxy-3-oxo-2,3-dihydro-1H-inden-1-yl)acetyl]amino}-1H-benzimidazol-1-yl)-3-phenylpropanoic acid
3-{5-[(9H-fluoren-9-ylacetyl)amino]-1H-benzimidazol-1-yl}-3-phenylpropanoic acid
3-(5-{[(9-oxo-9H-fluoren-1-yl)carbonyl]amino}-1H-benzimidazol-1-yl)-3-phenylpropanoic acid
3-(5-{[(2-nitrophenyl)acetyl]amino}-1H-benzimidazol-1-yl)-3-phenylpropanoic acid
3-(5-{[(4-nitrophenyl)acetyl]amino}-1H-benzimidazol-1-yl)-3-phenylpropanoic acid
3-{5-[(9-anthrylcarbonyl)amino]-1H-benzimidazol-1-yl}-3-phenylpropanoic acid
3-(5-{[(2-methylphenyl)acetyl]amino}-1H-benzimidazol-1-yl)-3-phenylpropanoic acid
3-(5-{[(2,6-dioxo-1,2,3,6-tetrahydro-4-pyrimidinyl)carbonyl]amino}-1H-benzimidazol-1-yl)-3-phenylpropanoic acid
3-(5-{[(4-methylphenyl)acetyl]amino}-1H-benzimidazol-1-yl)-3-phenylpropanoic acid
3-{5-[(3-methylbenzoyl)amino]-1H-benzimidazol-1-yl}-3-phenylpropanoic acid
3-phenyl-3-{5-[(4-vinylbenzoyl)amino]-1H-benzimidazol-1-yl}propanoic acid
3-{5-[(4-methylbenzoyl)amino]-1H-benzimidazol-1-yl}-3-phenylpropanoic acid
3-{5-[(2-methylbenzoyl)amino]-1H-benzimidazol-1-yl}-3-phenylpropanoic acid
3-(5-{[(3-methylphenyl)acetyl]amino}-1H-benzimidazol-1-yl)-3-phenylpropanoic acid
3-(5-{[(3-nitrophenyl)acetyl]amino}-1H-benzimidazol-1-yl)-3-phenylpropanoic acid
3-{5-[(4-bromobenzoyl)amino]-1H-benzimidazol-1-yl}-3-phenylpropanoic acid
3-phenyl-3-{5-[(9H-xanthen-9-ylcarbonyl)amino]-1H-benzimidazol-1-yl}propanoic acid
3-{5-[(2-phenoxypropanoyl)amino]-1H-benzimidazol-1-yl}-3-phenylpropanoic acid
3-(5-{[(1,3-dioxo-1,3-dihydro-2H-isoindol-2-yl)acetyl]amino}-1H-benzimidazol-1-yl)-3-phenylpropanoic acid -continued 3-{5-[(1,3-benzodioxol-5-ylcarbonyl)amino]-1H-benzimidazol-1-yl}-3-phenylpropanoic acid
3-phenyl-3-{5-[(phenylacetyl)amino]-1H-benzimidazol-1-yl}propanoic acid
3-{5-[(bicyclo[2.2.1]hept-5-en-2-ylcarbonyl)amino]-1H-benzimidazol-1-yl}-3-phenylpropanoic acid
3-(5-{[hydroxy(phenyl)acetyl]amino}-1H-benzimidazol-1-yl)-3-phenylpropanoic acid
3-(5-{[(2-naphthyloxy)acetyl]amino}-1H-benzimidazol-1-yl)-3-phenylpropanoic acid
3-phenyl-3-(5-{[(1-phenylcyclopentyl)carbonyl]amino}-1H-benzimidazol-1-yl)propanoic acid
3-phenyl-3-{5-[(2-sulfanylbenzoyl)amino]-1H-benzimidazol-1-yl}propanoic acid
3-(5-{[cyclopentyl(phenyl)acetyl]amino}-1H-benzimidazol-1-yl)-3-phenylpropanoic acid
3-{5-[(4-tert-butylbenzoyl)amino]-1H-benzimidazol-1-yl}-3-phenylpropanoic acid
3-{5-[(1-adamantylcarbonyl)amino]-1H-benzimidazol-1-yl}-3-phenylpropanoic acid
3-{5-[(4-methoxybenzoyl)amino]-1H-benzimidazol-1-yl}-3-phenylpropanoic acid
3-{5-[(4-cyclohexylbenzoyl)amino]-1H-benzimidazol-1-yl}-3-phenylpropanoic acid
3-[5-(1-naphthoylamino)-1H-benzimidazol-1-yl]-3-phenylpropanoic acid
3-[5-(benzoylamino)-1H-benzimidazol-1-yl]-3-phenylpropanoic acid
3-(5-{[(2E)-3-(4-bromophenyl)-2-propenoyl]amino}-1H-benzimidazol-1-yl)-3-phenylpropanoic acid
3-{5-[(3-bromo-4-methoxybenzoyl)amino]-1H-benzimidazol-1-yl}-3-phenylpropanoic acid
3-{5-[(4-butylbenzoyl)amino]-1H-benzimidazol-1-yl}-3-phenylpropanoic acid
3-(5-{[4-(dimethylamino)benzoyl]amino}-1H-benzimidazol-1-yl)-3-phenylpropanoic acid
3-(5-{[(4-bromo-1-ethyl-3-methyl-1H-pyrazol-5-yl)carbonyl]amino}-1H-benzimidazol-1-yl)-3-phenylpropanoic acid
3-{5-[(4-nitorbenzoyl)amino]-1H-benzimidazol-1-yl}-3-phenylpropanoic acid
3-(5-{[(2-cyclopropyl-4-quinolinyl)carbonyl]amino}-1H-benzimidazol-1-yl)-3-phenylpropanoic acid
3-phenyl-3-[5-({[2-(2-thienyl)-4-quinolinyl]carbonyl}amino)-1H-benzimidazol-1-yl]propanoic acid
3-{5-[(3,5-dinitrobenzyol)amino]-1H-benzimidazol-1-yl}-3-phenylpropanoic acid
3-phenyl-3-{5-[(3-phenyl-2-propynol)amino]-1H-benzimidazol-1-yl}propanoic acid
3-{5-[(4-fluoro-1-naphthoyl)amino]-1H-benzimidazol-1-yl}-3-phenylpropanoic acid
3-(5-{[(7-methyl-2-phenyl-4-quinolinyl)carbonyl]amino}-1H-benzimidazol-1-yl)-3-phenylpropanoic acid
3-(5-{[(5-bromo-4-methoxy-3-thienyl)carbonyl]amino}-1H-benzimidazol-1-yl)-3-phenylpropanoic acid
3-{5-[(4-[1,1'-biphenyl]-4-yl-4-oxobutanoyl)amino]-1H-benzimidazol-1-yl}-3-phenylpropanoic acid
3-{5-[(1-cyclohexen-1-ylcarbonyl)amino]-1H-benzimidazol-1-yl}-3-phenylpropanoic acid
3-(5-{[(4-bromophenyl)acetyl]amino}-1H-benzimidazol-1-yl)-3-phenylpropanoic acid
3-(5-{[2-(methylsulfanyl)benzoyl]amino}-1H-benzimidazol-1-yl)-3-phenylpropanoic acid
3-(5-{[(2E)-3-(5-bromo-2-ethoxyphenyl)-2-propenoyl]amino}-1H-benzimidazol-1-yl)-3-phenylpropanoic acid
3-(5-{[4-(methylsulfonyl)benzoyl]amino}-1H-benzimidazol-1-yl)-3-phenylpropanoic acid
3-(5-{[2-nitro-4-(trifluoromethyl)benzoyl]amino}-1H-benzimidazol-1-yl)-3-phenylpropanoic acid
3-{5-[([1,1'-biphenyl]-4-ylcarbonyl)amino]-1H-benzimidazol-1-yl}-3-phenylpropanoic acid
3-{5-[(4-benzoylbenzoyl)amino]-1H-benzimidazol-1-yl}-3-phenylpropanoic acid
3-phenyl-3-(5-{[4-(trifluoromethyl)benzoyl]amino}-1H-benzimidazol-1-yl)propanoic acid
3-{5-[(4-acetylbenzoyl)amino]-1H-benzimidazol-1-yl}-3-phenylpropanoic acid
3-{5-[(4-cyanobenzoyl)amino]-1H-benzimidazol-1-yl}-3-phenylpropanoic acid
3-(5-{[2,4-bis(trifluoromethyl)benzoyl]amino}-1H-benzimidazol-1-yl)-3-phenylpropanoic acid
3-phenyl-3-(5-{[3-(trifluoromethyl)benzoyl]amino}-1H-benzimidazol-1-yl)propanoic acid
3-{5-[(3-cyanobenzoyl)amino]-1H-benzimidazol-1-yl}-3-phenylpropanoic acid
3-{5-[(1H-benzimidazol-5-ylcarbonyl)amino]-1H-benzimidazol-1-yl}-3-phenylpropanoic acid
3-{5-[(diphenylacetyl)amino]-1H-benzimidazol-1-yl}-3-phenylpropanoic acid
3-{5-[(2-hydroxybenzoyl)amino]-1H-benzimidazol-1-yl}-3-phenylpropanoic acid
3-{5-[(4-ethylbenzoyl)amino]-1H-benzimidazol-1-yl}-3-phenylpropanoic acid
3-{5-[(3-bromo-2,6-dimethoxybenzoyl)amino]-1H-benzimidazol-1-yl}-3-phenylpropanoic acid
3-{5-[(4-bromo-2,3,5,6-tetrafluorobenzoyl)amino]-1H-benzimidazol-1-yl}-3-phenylpropanoic acid
3-{5-[(5-bromo-2-furoyl)amino]-1H-benzimidazol-1-yl}-3-phenylpropanoic acid
3-{5-[(3-iodobenzoyl)amino]-1H-benzimidazol-1-yl}-3-phenylpropanoic acid
3-{5-[(2-formylbenzoyl)amino]-1H-benzimidazol-1-yl}-3-phenylpropanoic acid
3-{5-[(2-bromobenzoyl)amino]-1H-benzimidazol-1-yl-}-3-phenylpropanoic acid
3-{5-[(3-bromobenzoyl)amino]-1H-benzimidazol-1-yl}-3-phenylpropanoic acid
3-(5-{[(5-bromo-3-pyridinyl)carbonyl]amino}-1H-benzimidazol-1-yl)-3-phenylpropanoic acid
3-(5-{[(5-bromo-2-thienyl)carbonyl]amino}-1H-benzimidazol-1-yl)-3-phenylpropanoic acid
3-{5-[(2-bromo-5-methoxybenzoyl)amino]-1H-benzimidazol-1-yl}-3-phenlpropanoic acid
3-{5-[(4-bromo-2-methylbenzoyl)amino]-1H-benzimidazol-1-yl}-3-phenylpropanoic acid
3-{5-[(4-bromo-2-chlorobenzoyl)amino]-1H-benzimidazol-1-yl}-3-phenylpropanoic acid
3-(5-{[(2E)-3-(3-bromo-4-fluorophenyl)-2-propenoyl]amino}-1H-benzimidazol-1-yl)-3-phenylpropanoic acid
3-(5-{[(2E)-3-(6-bromo-1,3-benzodioxol-5-yl)-2-propenoyl]amino}-1H-benzimidazol-1-yl)-3-phenylpropanoic acid -continued 3-phenyl-3-[5-({[2-(phenylsulfanyl)-3-pyridinyl]carbonyl}amino)-1H-benzimidazol-1-yl]propanoic acid
3-{5-[(2-hydroxy-5-nitrobenzoyl)amino]-1H-benzimidazol-1-yl}-3-phenylpropanoic acid
3-{5-[(2-hydroxy-3-methoxybenzoyl)amino]-1H-benzimidazol-1-yl}-3-phenylpropanoic acid
3-(5-{[(4-hydroxy-3-methoxyphenyl)acetyl]amino}-1H-benzimidazol-1-yl)-3-phenylpropanoic acid
3-{5-[(2,5-dihydroxybenzoyl)amino]-1H-benzimidazol-1-yl}-3-phenylpropanoic acid
3-{5-[(2-hydroxy-3-methylbenzoyl)amino]-1H-benzimidazol-1-yl}-3-phenylpropanoic acid
3-{5-[(3-hydroxy-4-methylbenzoyl)amino]-1H-benzimidazol-1-yl}-3-phenylpropanoic acid
3-(5-{[(3-hydroxy-4-methoxyphenyl)acetyl]amino}-1H-benzimidazol-1-yl)-3-phenylpropanoic acid
3-(5-{[(4,7-dimethylpyrazolo[5,1-c][1,2,4]triazin-3-yl)carbonyl]amino}-1H-benzimidazol-1-yl)-3-phenylpropanoic acid
3-(5-{[3-(2,4-dihydroxyphenyl)propanoyl]amino}-1H-benzimidazol-1-yl)-3-phenylpropanoic acid
3-(5-{[(3,5-ditert-butyl-4-hydroxyphenyl)acetyl]amino}-1H-benzimidazol-1-yl)-3-phenylpropanoic acid
3-(5-{[(6-hydroxy-2,5,7,8-tetramethyl-3,4-dihydro-2H-chromen-2-yl)carbonyl]amino}-1H-benzimidazol-1-yl)-3-phenylpropanoic acid
3-{5-[(3,5-dichloro-2-hydroxybenzoyl)amino]-1H-benzimidazol-1-yl}-3-phenylpropanoic acid
3-phenyl-3-{5-[(2,4,6-trihydroxybenzoyl)amino]-1H-benzimidazol-1-yl}propanoic acid
3-{5-[(2-hydroxybenzoyl)amino]-1H-benzimidazol-1-yl}-3-phenylpropanoic acid
3-phenyl-3-{5-[(2,3,5-trichloro-6-hydroxybenzoyl)amino]-1H-benzimidazol-1-yl}propanoic acid
3-{5-[(5-chloro-2-hydroxybenzoyl)amino]-1H-benzimidazol-1-yl}-3-phenylpropanoic acid
3-{5-[(5-bromo-2-hydroxybenzoyl)amino]-1H-benzimidazol-1-yl}-3-phenylpropanoic acid
3-{5-[(2-hydroxy-4-methylbenzoyl)amino]-1H-benzimidazol-1-yl}-3-phenylpropanoic acid
3-(5-{[(3,4-dihydroxyphenyl)acetyl]amino}-1H-benzimidazol-1-yl)-3-phenylpropanoic acid
3-{5-[(2-fluoro-6-iodobenzoyl)amino]-1H-benzimidazol-1-yl}-3-phenylpropanoic acid
3-phenyl-3-{6-[(2-quinolinylcarbonyl)amino]-1H-benzimidazol-1-yl}propanoic acid
3-{6-[(3-isoquinolinylcarbonyl)amino]-1H-benzimidazol-1-yl}-3-phenylpropanoic acid
3-phenyl-3-{6-[(2-quinoxalinylcarbonyl)amino]-1H-benzimidazol-1-yl}propanoic acid
3-{6-[(1-isoquinolinylcarbonyl)amino]-1H-benzimidazol-1-yl}-3-phenylpropanoic acid
3-{6-[(2,3-dihydro-1H-indol-2-ylcarbonyl)amino]-1H-benzimidazol-1-yl}-3-phenylpropanoic acid
3-phenyl-3-{6-[(2-quinoxalinylcarbonyl)amino]-1H-benzimidazol-1-yl}propanoic acid
3-phenyl-3-{6-[(2-pyrazinylcarbonyl)amino]-1H-benzimidazol-1-yl}propanoic acid
3-phenyl-3-{6-[(3-pyridinylcarbonyl)amino]-1H-benzimidazol-1-yl}propanoic acid
3-[6-(isonicotinoylamino)-1H-benzimidazol-1-yl]-3-phenylpropanoic acid
3-(6-{[(2-hydroxy-3-pyridinyl)carbonyl]amino}-1H-benzimidazol-1-yl)-3-phenylpropanoic acid
3-{6-[(1H-indol-2-ylcarbonyl)amino]-1H-benzimidazol-1-yl}-3-phenylpropanoic acid
3-{6-[(1H-indol-3-ylcarbonyl)amino]-1H-benzimidazol-1-yl}-3-phenylpropanoic acid
3-{6-[(3-nitrobenzoyl)amino]-1H-benzimidazol-1-yl}-3-phenylpropanoic acid
3-(6-{[(2E)-3-(1H-indol-3-yl)-2-propenoyl]amino}-1H-benzimidazol-1-yl)-3-phenylpropanoic acid
3-(6-{[(2E)-3-(3-nitrophenyl)-2-propenoyl]amino}-1H-benzimidazol-1-yl)-3-phenylpropanoic acid
3-(6-{[3-(1H-benzimidazol-2-yl)propanoyl]amino}-1H-benzimidazol-1-yl)-3-phenylpropanoic acid
3-phenyl-3-(6-{[3-(3,4,5-trimethoxyphenyl)propanoyl]amino}-1H-benzimidazol-1-yl)propanoic acid
3-{6-[(1H-indol-3-ylacetyl)amino]-1H-benzimidazol-1-yl}-3-phenylpropanoic acid
3-(6-{[3-(1H-indol-3-yl)propanoyl]amino}-1H-benzimidazol-1-yl)-3-phenylpropanoic acid
3-phenyl-3-{6-[(2-pyridinylcarbonyl)amino]-1H-benzimidazol-1-yl}propanoic acid
3-(6-{[(5-methyl-2-pyrazinyl)carbonyl]amino}-1H-benzimidazol-1-yl)-3-phenylpropanoic acid
3-(6-{[(5-methyl-2-phenyl-2H-1,2,3-triazol-4-yl)carbonyl]amino}-1H-benzimidazol-1-yl)-3-phenylpropanoic acid
3-(6-{[(4-oxo-4,5,6,7-tetrahydro-1-benzofuran-3-yl)carbonyl]amino}-1H-benzimidazol-1-yl)-3-phenylpropanoic acid
3-[6-({[2-(methylsulfanyl)-3-pyridinyl]carbonyl}amino)-1H-benzimidazol-1-yl]-3-phenylpropanoic acid
3-[6-({[3-chloro-4-(isopropylsulfonyl)-2-thienyl]carbonyl}amino)-1H-benzimidazol-1-yl]-3-phenylpropanoic acid
3-(6-{[(6-oxo-1,4,5,6-tetrahydro-3-pyridazinyl)carbonyl]amino}-1H-benzimidazol-1-yl)-3-phenylpropanoic acid
3-[6-({[2-(2,3-dihydro-1,4-benzodioxin-2-yl)-1,3-thiazol-4-yl]carbonyl}amino)-1H-benzimidazol-1-yl]-3-phenylpropanoic acid
3-[6-({(2E)-3-[3-nitro-4-(1-pyrrolidinyl)phenyl]-2-propenoyl}amino)-1H-benzimidazol-1-yl]-3-phenylpropanoic acid
3-(6-{[3-(2-oxocyclododecyl)propanoyl]amino}-1H-benzimidazol-1-yl)-3-phenylpropanoic acid
3-(6-{[(1-tert-butyl-3-methyl-1H-pyrazol-5-yl)carbonyl]amino}-1H-benzimidazol-1-yl)-3-phenylpropanoic acid
3-(6-{[(2Z)-2-(3-oxo-2-benzofuran-1(3H)-ylidene)ethanoyl]amino}-1H-benzimidazol-1-yl)-3-phenylpropanoic acid 3-{6-[(1-benzothien-2-ylcarbonyl)amino]-1H-benzimidazol-1-yl}-3-phenylpropanoic acid
3-phenyl-3-(6-{[4-(trifluoromethoxy)benzoyl]amino}-1H-benzimidazol-1-yl)propanoic acid
3-(6-{[(5-chloro-2-hydroxy-3-pyridinyl)carbonyl]amino}-1H-benzimidazol-1-yl)-3-phenylpropanoic acid
3-(6-{[(2E)-4-oxo-4-(2,3,4,5,6-pentamethylphenyl)-2-butenoyl]amino}-1H-benzimidazol-1-yl)-3-phenylpropanoic acid
3-(6-{[(6-bromo-2-oxo-2H-chromen-3-yl)carbonyl]amino}-1H-benzimidazol-1-yl)-3-phenylpropanoic acid
3-phenyl-3-(6-{[4-(trifluoroacetyl)benzoyl]amino}-1H-benzimidazol-1-yl)propanoic acid
3-[6-({[(4-chlorobenzoyl)amino]acetyl}amino)-1H-benzimidazol-1-yl]-3-phenylpropanoic acid
3-(6-{[(2,7-dimethylpyrazolo[1,5-a]pyrimidin-6-yl)carbonyl]amino}-1H-benzimidazol-1-yl)-3-phenylpropanoic acid
3-(6-{[2-(4-aminophenoxy)-2-methylpropanoyl]amino}-1H-benzimidazol-1-yl)-3-phenylpropanoic acid
3-(6-{[(4-acetyl-5-methyl-2-oxo-2,3-dihydro-1H-pyrrol-3-yl)acetyl]amino}-1H-benzimidazol-1-yl)-3-phenylpropanoic acid
3-phenyl-3-(6-{[(4-phenyl-1,2,3-thiadiazol-5-yl)carbonyl]amino}-1H-benzimidazol-1-yl)propanoic acid
3-[6-({[1-(4-chlorobenzyl)-5-oxo-3-pyrrolidinyl]carbonyl}amino)-1H-benzimidazol-1-yl]-3-phenylpropanoic acid
3-(6-{[({[(Z)-1-(4-chlorophenyl)ethylidene]amino}oxy)acetyl]amino}-1H-benzimidazol-1-yl)-3-phenylpropanoic acid
3-phenyl-3-{6-[(1,2,3-thiadiazol-4-ylcarbonyl)amino]-1H-benzimidazol-1-yl}propanoic acid
3-(6-{[(5-chloro-1-benzothien-3-yl)acetyl]amino}-1H-benzimidazol-1-yl)-3-phenylpropanoic acid
3-[6-({[5-chloro-2-(methylsulfanyl)-4-pyrimidinyl]carbonyl}amino)-1H-benzimidazol-1-yl]-3-phenylpropanoic acid
3-[6-({[1-(2-furylmethyl)-5-oxo-3-pyrrolidinyl]carbonyl}amino)-1H-benzimidazol-1-yl]-3-phenylpropanoic acid
3-(6-{[(3-tert-butyl-1-methyl-1H-pyrazol-5-yl)carbonyl]amino}-1H-benzimidazol-1-yl)-3-phenylpropanoic acid
3-(6-{[(5-oxo-2-pyrrolidinyl)carbonyl]amino}-1H-benzimidazol-1-yl)-3-phenylpropanoic acid
3-(6-{[(2,5-dimethoxyphenyl)acetyl]amino}-1H-benzimidazol-1-yl)-3-phenylpropanoic acid
3-[6-({[2-(4-methylphenoxy)-3-pyridinyl]carbonyl}amino)-1H-benzimidazol-1-yl]-3-phenylpropanoic acid
3-[6-(2-methyl-6-nitro-4-oxo-3(4H)-quinazolinyl)-1H-benzimidazol-1-yl]-3-phenylpropanoic acid
3-(6-{[(3-methoxyphenyl)acetyl]amino}-1H-benzimidazol-1-yl)-3-phenylpropanoic acid
3-(6-{[(4-methoxyphenyl)acetyl]amino}-1H-benzimidazol-1-yl)-3-phenylpropanoic acid
3-(6-{[(2-methoxyphenyl)acetyl]amino}-1H-benzimidazol-1-yl)-3-phenylpropanoic acid
3-(6-{[(2-phenoxy-3-pyridinyl)carbonyl]amino}-1H-benzimidazol-1-yl)-3-phenylpropanoic acid
3-[6-({2-[4-(aminocarbonyl)phenoxy]-2-methylpropanoyl}amino)-1H-benzimidazol-1-yl]-3-phenylpropanoic acid
3-phenyl-3-{6-[(1,2,3,4-tetrahydro-2-naphthalenylcarbonyl)amino]-1H-benzimidazol-1-yl}propanoic acid
3-(6-{[(3,5-dimethyl-4-isoxazolyl)carbonyl]amino}-1H-benzimidazol-1-yl)-3-phenylpropanoic acid
3-phenyl-3-{6-[(1H-pyrrol-2-ylcarbonyl)amino]-1H-benzimidazol-1-yl}propanoic acid
3-[6-({[(2S)-5-oxopyrrolidinyl]carbonyl}amino)-1H-benzimidazol-1-yl]-3-phenylpropanoic acid
3-phenyl-3-[6-({[(3S,4R,5S)-3,4,5-trihydroxy-1-cyclohexen-1-yl]carbonyl}amino)-1H-benzimidazol-1-yl]propanoic acid
3-{6-[(cyclohexylacetyl)amino]-1H-benzimidazol-1-yl}-3-phenylpropanoic acid
3-phenyl-3-(6-{[4-(1H-pyrrol-1-yl)benzoyl]amino}-1H-benzimidazol-1-yl)propanoic acid
3-(6-{[(2,4-dihydroxy-5-pyrimidinyl)carbonyl]amino}-1H-benzimidazol-1-yl)-3-phenylpropanoic acid
3-(6-{[2-(1,3-dioxo-1,3-dihydro-2H-isoindol-2-yl)propanoyl]amino}-1H-benzimidazol-1-yl)-3-phenylpropanoic acid
3-(6-{[3-(1,3-dioxo-1,3-dihydro-2H-isoindol-2-yl)propanoyl]amino}-1H-benzimidazol-1-yl)-3-phenylpropanoic acid
3-[6-({[1-(4-chlorophenyl)cyclopentyl]carbonyl}amino)-1H-benzimidazol-1-yl]-3-phenylpropanoic acid
3-(6-{[(4-oxo-2-thioxo-1,3-thiazolidin-3-yl)acetyl]amino}-1H-benzimidazol-1-yl)-3-phenylpropanoic acid
3-[6-({[(4S)-2,6-dioxohexahydro-4-pyrimidinyl]carbonyl}amino)-1H-benzimidazol-1-yl]-3-phenylpropanoic acid
3-{6-[([1,1'-biphenyl]-4-ylacetyl)amino]-1H-benzimidazol-1-yl}-3-phenylpropanoic acid
3-(6-{[(6-methoxy-3-oxo-2,3-dihydro-1H-inden-1-yl)acetyl]amino}-1H-benzimidazol-1-yl)-3-phenylpropanoic acid
3-{6-[(9H-fluoren-9-ylacetyl)amino]-1H-benzimidazol-1-yl}-3-phenylpropanoic acid
3-(6-{[(9-oxo-9H-fluoren-1-yl)carbonyl]amino}-1H-benzimidazol-1-yl)-3-phenylpropanoic acid
3-(6-{[(2-nitrophenyl)acetyl]amino}-1H-benzimidazol-1-yl)-3-phenylpropanoic acid
3-(6-{[(4-nitrophenyl)acetyl]amino}-1H-benzimidazol-1-yl)-3-phenylpropanoic acid 3-{6-[(9-anthrylcarbonyl)amino]-1H-benzimidazol-1-yl}-3-phenylpropanoic acid
3-(6-{[(2-methylphenyl)acetyl]amino}-1H-benzimidazol-1-yl)-3-phenylpropanoic acid
3-(6-{[(2,6-dioxo-1,2,3,6-tetrahydro-4-pyrimidinyl)carbonyl]amino}-1H-benzimidazol-1-yl)-3-phenylpropanoic acid
3-(6-{[(4-methylphenyl)acetyl]amino}-1H-benzimidazol-1-yl)-3-phenylpropanoic acid
3-{6-[(3-methylbenzoyl)amino]-1H-benzimidazol-1-yl}-3-phenylpropanoic acid
3-phenyl-3-{6-[(4-vinylbenzoyl)amino]-1H-benzimidazol-1-yl}propanoic acid
3-{6-[(4-methylbenzoyl)amino]-1H-benzimidazol-1-yl}-3-phenylpropanoic acid
3-{6-[(2-methylbenzoyl)amino]-1H-benzimidazol-1-yl}-3-phenylpropanoic acid
3-(6-{[(3-methylphenyl)acetyl]amino}-1H-benzimidazol-1-yl)-3-phenylpropanoic acid
3-(6-{[(3-nitrophenyl)acetyl]amino}-1H-benzimidazol-1-yl)-3-phenylpropanoic acid
3-{6-[(4-bromobenzoyl)amino]-1H-benzimidazol-1-yl}-3-phenylpropanoic acid
3-phenyl-3-{6-[(9H-xanthen-9-ylcarbonyl)amino]-1H-benzimidazol-1-yl}propanoic acid
3-{6-[(2-phenoxypropanoyl)amino]-1H-benzimidazol-1-yl}-3-phenylpropanoic acid
3-(6-{[(1,3-dioxo-1,3-dihydro-2H-isoindol-2-yl)acetyl]amino}-1H-benzimidazol-1-yl)-3-phenylpropanoic acid
3-{6-[(1,3-benzodioxol-5-ylcarbonyl)amino]-1H-benzimidazol-1-yl}-3-phenylpropanoic acid
3-phenyl-3-{6-[(phenylacetyl)amino]-1H-benzimidazol-1-yl}propanoic acid
3-{6-[(bicyclo[2.2.1]hept-5-en-2-ylcarbonyl)amino]-1H-benzimidazol-1-yl}-3-phenylpropanoic acid
3-(6-{[hydroxy(phenyl)acetyl]amino}-1H-benzimidazol-1-yl)-3-phenylpropanoic acid
3-(6-{[(2-naphthyloxy)acetyl]amino}-1H-benzimidazol-1-yl)-3-phenylpropanoic acid
3-phenyl-3-(6-{[(1-phenylcyclopentyl)carbonyl]amino}-1H-benzimidazol-1-yl)propanoic acid
3-phenyl-3-{6-[(tetrahydro-2-furanylcarbonyl)amino]-1H-benzimidazol-1-yl}propanoic acid
3-(6-{[cyclopentyl(phenyl)acetyl]amino}-1H-benzimidazol-1-yl)-3-phenylpropanoic acid
3-{6-[(4-tert-butylbenzoyl)amino]-1H-benzimidazol-1-yl}-3-phenylpropanoic acid
3-{6-[(1-adamantylcarbonyl)amino]-1H-benzimidazol-1-yl}-3-phenylpropanoic acid
3-{6-[(4-methoxybenzoyl)amino]-1H-benzimidazol-1-yl}-3-phenylpropanoic acid
3-{6-[(4-cyclohexylbenzoyl)amino]-1H-benzimidazol-1-yl}-3-phenylpropanoic acid
3-[6-(1-naphthoylamino)-1H-benzimidazol-1-yl]-3-phenylpropanoic acid
3-[6-(benzoylamino)-1H-benzimidazol-1-yl]-3-phenylpropanoic acid
3-{6-[(5-isoxazolylcarbonyl)amino]-1H-benzimidazol-1-yl}-3-phenylpropanoic acid
3-(6-{[(2E)-3-(4-bromophenyl)-2-propenoyl]amino}-1H-benzimidazol-1-yl)-3-phenylpropanoic acid
3-{6-[(3-bromo-4-methoxybenzoyl)amino]-1H-benzimidazol-1-yl}-3-phenylpropanoic acid
3-{6-[(4-butylbenzoyl)amino]-1H-benzimidazol-1-yl}-3-phenylpropanoic acid
3-(6-{[4-(dimethylamino)benzoyl]amino}-1H-benzimidazol-1-yl)-3-phenylpropanoic acid
3-(6-{[(4-bromo-1-ethyl-3-methyl-1H-pyrazol-5-yl)carbonyl]amino}-1H-benzimidazol-1-yl)-3-phenylpropanoic acid
3-{6-[(4-nitrobenzoyl)amino]-1H-benzimidazol-1-yl}-3-phenylpropanoic acid
3-(6-{[(2-cyclopropyl-4-quinolinyl)carbonyl]amino}-1H-benzimidazol-1-yl)-3-phenylpropanoic acid
3-phenyl-3-[6-({[2-(2-thienyl)-4-quinolinyl]carbonyl}amino)-1H-benzimidazol-1-yl]propanoic acid
3-{6-[(3,5-dinitrobenzoyl)amino]-1H-benzimidazol-1-yl}-3-phenylpropanoic acid
3-phenyl-3-{6-[(3-phenyl-2-propynoyl)amino]-1H-benzimidazol-1-yl}propanoic acid
3-{6-[(4-fluoro-1-naphthoyl)amino]-1H-benzimidazol-1-yl}-3-phenylpropanoic acid
3-(6-{[(acetylamino)acetyl]amino}-1H-benzimidazol-1-yl)-3-phenylpropanoic acid
3-(6-{[(7-methyl-2-phenyl-4-quinolinyl)carbonyl]amino}-1H-benzimidazol-1-yl)-3-phenylpropanoic acid
3-(6-{[(5-bromo-4-methoxy-3-thienyl)carbonyl]amino}-1H-benzimidazol-1-yl)-3-phenylpropanoic acid
3-{6-[(4-[1,1'-biphenyl]-4-yl-4-oxobutanoyl)amino]-1H-benzimidazol-1-yl}-3-phenylpropanoic acid
3-{6-[(1-cyclohexen-1-ylcarbonyl)amino]-1H-benzimidazol-1-yl}-3-phenylpropanoic acid
3-(6-{[(4-bromophenyl)acetyl]amino}-1H-benzimidazol-1-yl)-3-phenylpropanoic acid
3-(6-{[2-(methylsulfanyl)benzoyl]amino}-1H-benzimidazol-1-yl)-3-phenylpropanoic acid
3-(6-{[(2E)-3-(5-bromo-2-ethoxyphenyl)-2-propenoyl]amino}-1H-benzimidazol-1-yl)-3-phenylpropanoic acid
3-(6-{[4-(methylsulfonyl)benzoyl]amino}-1H-benzimidazol-1-yl)-3-phenylpropanoic acid
3-(6-{[2-nitro-4-(trifluoromethyl)benzoyl]amino}-1H-benzimidazol-1-yl)-3-phenylpropanoic acid
3-{6-[([1,1'-biphenyl]-4-ylcarbonyl)amino]-1H-benzimidazol-1-yl}-3-phenylpropanoic acid
3-{6-[(4-benzoylbenzoyl)amino]-1H-benzimidazol-1-yl}-3-phenylpropanoic acid
3-phenyl-3-(6-{[4-(trifluoromethyl)benzoyl]amino}-1H-benzimidazol-1-yl)propanoic acid
3-{6-[(4-acetylbenzoyl)amino]-1H-benzimidazol-1-yl}-3-phenylpropanoic acid
3-{6-[(4-cyanobenzoyl)amino]-1H-benzimidazol-1-yl}-3-phenylpropanoic acid
3-(6-{[2,4-bis(trifluoromethyl)benzoyl]amino}-1H-benzimidazol-1-yl)-3-phenylpropanoic acid
3-phenyl-3-(6-{[3-(trifluoromethyl)benzoyl]amino}-1H-benzimidazol-1-yl)propanoic acid
3-{6-[(3-cyanobenzoyl)amino]-1H-benzimidazol-1-yl}-3-phenylpropanoic acid
3-(6-{[4-(3-methyl-5-oxo-4,5-dihydro-1H-pyrazol-1-yl)benzoyl]amino}-1H-benzimidazol-1-yl)-3-phenylpropanoic acid
3-{6-[(1H-benzimidazol-5-ylcarbonyl)amino]-1H-benzimidazol-1-yl}-3-phenylpropanoic acid
3-{6-[(diphenylacetyl)amino]-1H-benzimidazol-1-yl}-3-phenylpropanoic acid
3-{6-[(2-hydroxybenzoyl)amino]-1H-benzimidazol-1-yl}-3-phenylpropanoic acid -continued 3-{6-[(4-ethylbenzoyl)amino]-1H-benzimidazol-1-yl}-3-phenylpropanoic acid
3-(6-{[3-(2,5-dioxo-2,5-dihydro-1H-pyrrol-1-yl)propanoyl]amino}-1H-benzimidazol-1-yl)-3-phenylpropanoic acid
3-{6-[(3-bromo-2,6-dimethoxybenzoyl)amino]-1H-benzimidazol-1-yl}-3-phenylpropanoic acid
3-{6-[(4-bromo-2,3,5,6-tetrafluorobenzoyl)amino]-1H-benzimidazol-1-yl}-3-phenylpropanoic acid
3-{6-[(5-bromo-2-furoyl)amino]-1H-benzimidazol-1-yl}-3-phenylpropanoic acid
3-{6-[(3-iodobenzoyl)amino]-1H-benzimidazol-1-yl}-3-phenylpropanoic acid
3-{6-[(2-formylbenzoyl)amino]-1H-benzimidazol-1-yl}-3-phenylpropanoic acid
3-{6-[(2-bromobenzoyl)amino]-1H-benzimidazol-1-yl}-3-phenylpropanoic acid
3-{6-[(3-bromobenzoyl)amino]-1H-benzimidazol-1-yl}-3-phenylpropanoic acid
3-(6-{[(5-bromo-3-pyridinyl)carbonyl]amino}-1H-benzimidazol-1-yl)-3-phenylpropanoic acid
3-(6-{[(5-bromo-2-thienyl)carbonyl]amino}-1H-benzimidazol-1-yl)-3-phenylpropanoic acid
3-{6-[(2-bromo-5-methoxybenzoyl)amino]-1H-benzimidazol-1-yl}-3-phenylpropanoic acid
3-{6-[(4-bromo-2-methylbenzoyl)amino]-1H-benzimidazol-1-yl}-3-phenylpropanoic acid
3-{6-[(4-bromo-2-chlorobenzoyl)amino]-1H-benzimidazol-1-yl}-3-phenylpropanoic acid
3-(6-{[(2E)-3-(3-bromo-4-fluorophenyl)-2-propenoyl]amino}-1H-benzimidazol-1-yl)-3-phenylpropanoic acid
3-(6-{[(2E)-3-(6-bromo-1,3-benzodioxol-5-yl)-2-propenoyl]amino}-1H-benzimidazol-1-yl)-3-phenylpropanoic acid
3-{6-[(2-oxo-3-phenylpropanoyl)amino]-1H-benzimidazol-1-yl}-3-phenylpropanoic acid
3-{6-[(4-oxopentanoyl)amino]-1H-benzimidazol-1-yl}-3-phenylpropanoic acid
3-phenyl-3-[6-({[2-(phenylsulfanyl)-3-pyridinyl]carbonyl}amino)-1H-benzimidazol-1-yl]propanoic acid
3-{6-[(2-hydroxy-5-nitrobenzoyl)amino]-1H-benzimidazol-1-yl}-3-phenylpropanoic acid
3-{6-[(2-hydroxy-3-methoxybenzoyl)amino]-1H-benzimidazol-1-yl}-3-phenylpropanoic acid
3-(6-{[(4-hydroxy-3-methoxyphenyl)acetyl]amino}-1H-benzimidazol-1-yl)-3-phenylpropanoic acid
3-{6-[(2,5-dihydroxybenzoyl)amino]-1H-benzimidazol-1-yl}-3-phenylpropanoic acid
3-{6-[(2-hydroxy-3-methylbenzoyl)amino]-1H-benzimidazol-1-yl}-3-phenylpropanoic acid
3-{6-[(3-hydroxy-4-methylbenzoyl)amino]-1H-benzimidazol-1-yl}-3-phenylpropanoic acid
3-(6-{[(3-hydroxy-4-methoxyphenyl)acetyl]amino}-1H-benzimidazol-1-yl)-3-phenylpropanoic acid
3-(6-{[(4,7-dimethylpyrazolo[5,1-c][1,2,4]triazin-3-yl)carbonyl]amino}-1H-benzimidazol-1-yl)-3-phenylpropanoic acid
3-(6-{[3-(2,4-dihydroxyphenyl)propanoyl]amino}-1H-benzimidazol-1-yl)-3-phenylpropanoic acid
3-(6-{[(3,5-ditert-butyl-4-hydroxyphenyl)acetyl]amino}-1H-benzimidazol-1-yl)-3-phenylpropanoic acid
3-(6-{[(6-hydroxy-2,5,7,8-tetramethyl-3,4-dihydro-2H-chromen-2-yl)carbonyl]amino}-1H-benzimidazol-1-yl)-3-phenylpropanoic acid
3-{6-[(5-formyl-2-hydroxybenzoyl)amino]-1H-benzimidazol-1-yl}-3-phenylpropanoic acid
3-{6-[(3,5-dichloro-2-hydroxybenzoyl)amino]-1H-benzimidazol-1-yl}-3-phenylpropanoic acid
3-phenyl-3-{6-[(2,4,6-trihydroxybenzoyl)amino]-1H-benzimidazol-1-yl}propanoic acid
3-{6-[(2-hydroxybenzoyl)amino]-1H-benzimidazol-1-yl}-3-phenylpropanoic acid
3-phenyl-3-{6-[(2,3,5-trichloro-6-hydroxybenzoyl)amino]-1H-benzimidazol-1-yl}propanoic acid
3-{6-[(5-chloro-2-hydroxybenzoyl)amino]-1H-benzimidazol-1-yl}-3-phenylpropanoic acid
3-{6-[(5-bromo-2-hydroxybenzoyl)amino]-1H-benzimidazol-1-yl}-3-phenylpropanoic acid, and
3-{6-[(2-hydroxy-4-methylbenzoyl)amino]-1H-benzimidazol-1-yl}-3-phenylpropanoic acid
3-(6-{[(3,4-dihydroxyphenyl)acetyl]amino}-1H-benzimidazol-1-yl)-3-phenylpropanoic acid; and
3-{6-[(2-fluoro-6-iodobenzoyl)amino]-1H-benzimidazol-1-yl}-3-phenylpropanoic acid or a pharmaceutically acceptable salt thereof.

5. A composition comprising a compound according to claim 1, or a pharmaceutically acceptable salt thereof; and a pharmaceutically acceptable carrier.

6. A composition comprising a compound according to claim 1, or a pharmaceutically acceptable salt thereof; and an anti-neoplastic, anti-tumor, anti-angiogenic, or chemotherapeutic agent.

7. A composition comprising a compound according to claim 1, or a pharmaceutically acceptable salt thereof; and a cytotoxic cancer therapeutic agent.

8. A composition comprising a compound according to claim 1, or a pharmaceutically acceptable salt thereof; and an angiogenesis inhibiting cancer therapeutic agent.

* * * * *